(12) United States Patent
Manabe et al.

(10) Patent No.: US 6,489,487 B1
(45) Date of Patent: Dec. 3, 2002

(54) TRIAZOLONE DERIVATIVES, USE THEREOF, AND INTERMEDIATES THEREFOR

(75) Inventors: Akio Manabe, Sanda; Yoshiharu Kinoshita, Minoo; Hiroshi Sakaguchi; Tomohiro Araki, both of Toyonaka, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/762,242

(22) PCT Filed: Aug. 3, 1999

(86) PCT No.: PCT/JP99/04161

§ 371 (c)(1),
(2), (4) Date: Feb. 5, 2001

(87) PCT Pub. No.: WO00/07999

PCT Pub. Date: Feb. 17, 2000

(30) Foreign Application Priority Data

| Aug. 3, 1998 | (JP) | 10-218973 |
| Oct. 30, 1998 | (JP) | 10-310672 |
| Dec. 25, 1998 | (JP) | 10-370829 |

(51) Int. Cl.[7] .............. C07D 249/12; C07D 401/10; C07D 403/10; A01N 43/653; A01N 43/78

(52) U.S. Cl. .............. 548/263.6; 548/263.8; 548/264.6; 546/272.4; 544/333; 504/239; 504/253; 504/273; 514/256; 514/339; 514/384

(58) Field of Search .............. 548/263.6, 263.8, 548/264.6; 546/272.4; 544/333; 504/239, 253, 273; 514/256, 339, 384

(56) References Cited

U.S. PATENT DOCUMENTS

| 4,966,909 A | * 10/1990 | Kane et al. .............. 514/359 |
| 5,552,369 A | 9/1996 | Findeisen et al. .............. 504/273 |
| 5,654,438 A | 8/1997 | Findeisen et al. .............. 548/263.8 |

FOREIGN PATENT DOCUMENTS

| DE | 19834557 | 2/2000 |
| EP | 475898 | 3/1992 |
| JP | 58-116475 | 7/1983 |
| JP | 07-507544 | 8/1995 |
| JP | 08-325244 | 12/1996 |
| JP | 09-048767 | 2/1997 |
| JP | 09-095486 | 4/1997 |
| JP | 09-104676 | 4/1997 |
| WO | WO 95/14009 | 5/1995 |
| WO | WO 96/26191 | 8/1996 |
| WO | WO 96/36229 | 11/1996 |
| WO | WO 96/36615 | 11/1996 |
| WO | WO 96/36616 | 11/1996 |
| WO | WO 96/36633 | 11/1996 |
| WO | WO 96/38425 | 12/1996 |
| WO | WO 97/00612 | 1/1997 |
| WO | WO 97/02255 | 1/1997 |
| WO | WO 98/05652 | 2/1998 |
| WO | WO 98/15512 | 4/1998 |
| WO | WO 98/20003 | 5/1998 |
| WO | WO 98/23155 | 6/1998 |
| WO | WO 98/23156 | 6/1998 |
| WO | WO 98/33382 | 8/1998 |
| WO | WO 98/56774 | 12/1998 |
| WO | WO 99/05139 | 2/1999 |
| WO | WO 99/07687 | 2/1999 |
| WO | 99/07687 | 2/1999 |
| WO | WO 99/11129 | 3/1999 |
| WO | WO 99/18102 | 4/1999 |

OTHER PUBLICATIONS

Horng–Chin Huang et al., "Synthesis and Structure–Activity Relationships of Nonpeptide, Triazorone–Based Angiotensin II Receptor Antagonists"; Journal of Medicinal Chemistry vol. 36 (No. 15) pp. 2172–2181 (1993).

* cited by examiner

Primary Examiner—Richard L. Raymond
Assistant Examiner—Rao Uppu

(57) ABSTRACT

Triazolone derivatives represented by the formula

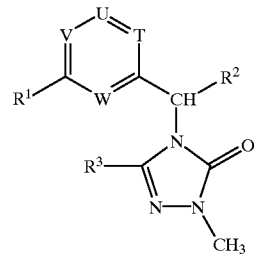

wherein $R^1$ represents optionally substituted $C_{1-10}$ alkyl, $A^1$—$L^1$—, $A^1$—ON=$CA^2$, etc.; $R^2$ represents hydrogen, $C_{1-6}$ alkyl, etc.; $R^3$ represents $C_{1-6}$ alkoxy, etc.; one of T, U, and V represents $CR^4$, another represents CH or nitrogen, and the remaining one represents $CR^5$ or nitrogen; and W represents $CR^6$ or nitrogen.

27 Claims, No Drawings

TRIAZOLONE DERIVATIVES, USE THEREOF, AND INTERMEDIATES THEREFOR

ART FIELD RELATED

The present invention relates to triazolone derivatives, use thereof, and intermediates therefor.

OBJECTS OF THE INVENTION

An object of the present invention is to provide compounds having excellent plant disease control activity.

SUMMARY OF THE INVENTION

As a result of the present inventors' intensive study, it has been found that triazolone derivatives represented by the following formula [I] have excellent plant disease control activity. Thus, the present invention has been completed.

That is, the present invention provides a triazolone derivative represented by the formula [I]

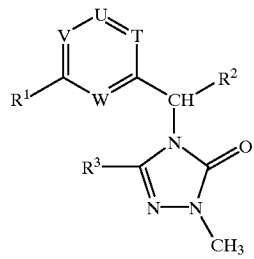

wherein $R^1$ represents optionally substituted $C_{1-10}$ alkyl, optionally substituted $C_{2-10}$ alkenyl, optionally substituted $C_{2-10}$ alkynyl, halogen (chlorine, bromine, iodine or fluorine), nitro, cyano, optionally substituted $C_{3-10}$ cycloalkyl, optionally substituted $C_{4-20}$ cycloalkylalkyl, optionally substituted $C_{5-10}$ cycloalkenyl, optionally substituted $C_{6-20}$ cycloalkenylalkyl, optionally substituted $C_{6-10}$ aryl, optionally substituted $C_{7-20}$ arylalkyl, optionally substituted $C_{1-9}$ heteroaryl, optionally substituted $C_{2-19}$ heteroarylalkyl, $A^1$—$L^1$—, $A^1$—ON=$CA^2$—, $A^1$—ON=C(Me)$CH_2$ON=$CA^2$—, $A^1C(A^2)$=NOCH$_2$—, $A^1SC(A^2)$=N—, $A^1C$(=S)NH—, $A^1SC$(=S)NH—, $A^1SC(SA^2)$=N—, $A^1$—ON=C(CN)—, $A^1$—ON=C(Me)$CH_2$ON=C(CN)—, or $A^1C$(CN)=NOCH$_2$— (wherein $L^1$ represents oxygen, sulfur, carbonyl, —OCH$_2$—, —SCH$_2$—, —C(=O)O—, —OC(=O)—, —C(=O)OCH$_2$—, —NH—, or $C_{1-6}$ alkylimino; $A^1$ and $A^2$ are the same or different, and each represents optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted $C_{4-20}$ cycloalkylalkyl, optionally substituted $C_{5-10}$ cycloalkenyl, optionally substituted $C_{6-20}$ cycloalkenylalkyl, optionally substituted $C_{6-10}$ aryl, optionally substituted $C_{7-20}$ arylalkyl, hydrogen, optionally substituted $C_{1-9}$ heteroaryl, or optionally substituted $C_{2-19}$ heteroarylalkyl);

$R^2$ represents hydrogen, or $C_{1-6}$ alkyl;

$R^3$ represents $C_{1-6}$ alkoxy, $C_{1-6}$ alkylthio, cyano, halogen, vinyl, ethynyl, cyclopropyl, or $C_{1-6}$ alkyl;

one of T, U and V represents $CR^4$, another one represents CH or nitrogen, and the remaining one represents $CR^5$ or nitrogen; and W represents $CR^6$ or nitrogen;

(wherein $R^4$, $R^5$ and $R^6$ are the same or different, and each represents hydrogen, halogen, $C_{1-6}$ alkyl, $C_{1-6}$ alkoxy, $C_{1-6}$ haloalkyl, $C_{1-6}$ haloalkoxy, cyano, nitro, $C_{2-6}$ alkoxycarbonyl, $C_{1-6}$ alkylthio, or $C_{1-6}$ haloalkylthio) (hereinafter referred to as the compound of the present invention). Further, the present invention provides an agricultural or horticultural fungicide composition comprising as an active ingredient the compound of the present invention.

The present invention also provides intermediates useful for producing (a part of) the compound of the present invention, that is, an alkoxytriazolone compound represented by the formula [II-1]

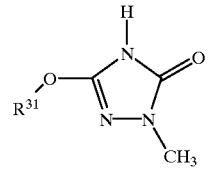

wherein $R^{31}$ represents $C_{1-6}$ alkyl (e.g., methyl, ethyl, etc.);

a boron compound represented by the formula [III-1]

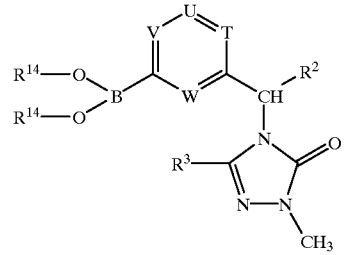

wherein both $R^{14}$ bind to each other at the terminal ends thereof to represent ethylene or trimethylene (they may be substituted with one or more methyl or phenyl, respectively) (e.g., —C(CH$_3$)$_2$—C(CH$_3$)$_2$—, —CH$_2$CH$_2$—, —CH$_2$CH$_2$CH$_2$—, —CH$_2$—C(CH$_3$)$_2$—CH$_2$—, —CH(Ph)—CH$_2$—CH(Ph)—, etc.), or it represents $C_{1-6}$ alkyl (e.g., methyl, ethyl, isopropyl, etc.) or hydrogen; and $R^2$, $R^3$, V, U, T and W are as defined above; and a triazolone compound represented by the formula [IV]

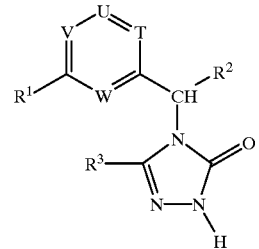

wherein $R^1$, $R^2$, $R^3$, V, U, T and W are as defined above.

DETAILED DESCRIPTION OF THE INVENTION

In the present invention, as the $C_{1-10}$ alkyl of the optionally substituted $C_{1-10}$ alkyl represented by $R^1$, $A^1$ and $A^2$, for example, there are methyl, ethyl, propyl, isopropyl, butyl, isobutyl, 1-methylpropyl, pentyl, 1-methylbutyl, 1-ethylbutyl, 2-methylbutyl, 3-methylbutyl, 2,2-dimethylpropyl, 1,2-dimethylpropyl, 1,1-dimethylpropyl, hexyl, 1-methylpentyl, 1-ethylpentyl, 3,3-dimethylbutyl, heptyl, 3,7-dimethyloctyl, and the like.

As the $C_{2-10}$ alkenyl of the optionally substituted $C_{2-10}$ alkenyl represented by $R^1$, $A^1$ and $A^2$, for example, there are vinyl, allyl, 1-methyl-2-propenyl, 2-methyl-2-propenyl, 2-butenyl, 2-pentenyl, 3-methyl-2-butenyl, and the like.

As the $C_{2-10}$ alkynyl of the optionally substituted $C_{2-10}$ alkynyl represented by $R^1$, $A^1$ and $A^2$, for example, there are ethynyl, propargyl, 1-methyl-2-propynyl, 2-butynyl, and the like.

As the halogen represented by $R^1$, there is chlorine, bromine, iodine or fluorine.

As the $C_{3-10}$ cycloalkyl of the optionally substituted $C_{3-10}$ cycloalkyl represented by $R^1$, $A^1$ and $A^2$, for example, there are cyclopropyl, cyclopentyl, cyclohexyl, and the like.

As the $C_{4-20}$ cycloalkylalkyl of the optionally substituted $C_{4-20}$ cycloalkylalkyl represented by $R^1$, $A^1$ and $A^2$, for example, there are cyclopropylmethyl, cyclopentylmethyl, 2-cyclopentylethyl, cyclohexylmethyl, and the like.

As the $C_{5-10}$ cycloalkenyl of the optionally substituted $C_{5-10}$ cycloalkenyl represented by $R^1$, $A^1$ and $A^2$, for example, there are cyclopentenyl, cyclohexenyl, and the like.

As the $C_{6-20}$ cycloalkenylalkyl of the optionally substituted $C_{6-20}$ cycloalkenylalkyl represented by $R^1$, $A^1$ and $A^2$, for example, there are cyclopentene-1-ylmethyl, cyclohexene-1-ylmethyl, and the like.

As the $C_{6-10}$ aryl of the optionally substituted $C_{6-10}$ aryl represented by $R^1$, $A^1$ and $A^2$, for example, there are phenyl, α-naphthyl, β-naphthyl, and the like.

As the $C_{7-20}$ arylalkyl of the optionally substituted $C_{7-20}$ arylalkyl represented by $R^1$, $A^1$ and $A^2$, for example, there are phenylmethyl, 2-phenylethyl, 3-phenylpropyl, 4-phenylbutyl, α-naphthylmethyl, β-naphthylmethyl, and the like.

As the $C_{1-9}$ heteroaryl of the optionally substituted $C_{1-9}$ heteroaryl represented by $R^1$, $A^1$ and $A^2$, for example, there are 2-pyridyl, 3-pyridyl, 4-pyridyl, 2-pyrimidinyl, 4-pyrimidinyl, 5-pyrimidinyl, 2-pyrazinyl, 3-pyridazinyl, 4-pyridazinyl, 2-thienyl, 3-thienyl, 2-furyl, 3-furyl, pyrrol-1-yl, pyrrol-2-yl, pyrrol-3-yl, 1-pyrazolyl, 3-pyrazolyl, 4-pyrazolyl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isoxazolyl, 4-isoxazolyl, 5-isoxazolyl, 1-imidazolyl, 2-imidazolyl, 4-imidazolyl, 5-imidazolyl, 1-(1,2,4-triazolyl), 3-(1,2,4-triazolyl), 4-(1,2,4-triazolyl), 2-benzothienyl, 3-benzothienyl, benzothiazol-2-yl, 2-quinolinyl, and the like.

As the $C_{2-19}$ heteroarylalkyl of the optionally substituted $C_{2-19}$ heteroarylalkyl represented by $R^1$, $A^1$ and $A^2$, for example, there are 2-pyridylmethyl, 4-pyridylmethyl, 2-pyrimidinylmethyl, 4-pyrimidinylmethyl, 3-pyrazolylmethyl, 2-thiazolymenthyl, 2-imidazolylmethyl, 3-(1,2,4-triazolyl)methyl, 2-quinolinylmethyl, and the like.

As the substituents of the optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted $C_{4-20}$ cycloalkylalkyl, optionally substituted $C_{5-10}$ cycloalkenyl, optionally substituted $C_{6-20}$ cycloalkenylalkyl, optionally substituted $C_{6-10}$ aryl, optionally substituted $C_{7-20}$ arylalkyl, optionally substituted $C_{1-9}$ heteroaryl, or optionally substituted $C_{2-19}$ heteroarylalkyl represented by $R^1$, $A^1$ and $A^2$, for example, there are:

halogen (chlorine, bromine, fluorine, etc.);

$C_{1-10}$ alkyl (e.g., methyl, ethyl, propyl, isopropyl, butyl, isobutyl, 1-methylpropyl, pentyl, 1-methylbutyl, 1-ethylbutyl, 2-methylbutyl, 3-methylbutyl, 2,2-dimethylpropyl, 1,2-dimethylpropyl, 1,1-dimethylpropyl, hexyl, 1-methylpentyl, 1-ethylpent yl, 3,3-dimethylbutyl, heptyl, 3,7-dimethyloctyl, etc.);

$C_{3-20}$ trialkylsilyl (e.g. , trimethylsilyl, is triethylsilyl, etc.);

$C_{1-10}$ haloalkyl (e.g., trifluoromethyl, 2,2,2-trifluoroethyl, b,1,2,2-tetrafluoroethyl, etc.);

$C_{3-10}$ cycloalkyl (e.g., cyclopropyl, cyclopentyl, cyclohexyl, etc.);

$C_{1-10}$ alkoxy (e.g., methoxy, ethoxy, n-propoxy, isopropoxy, n-butoxy, sec-butoxy, isobutoxy, n-pentyloxy, etc.);

$C_{1-10}$ haloalkoxy (e.g., trifluoromethoxy, difluoromethoxy, bromodifluoromethoxy, chlorodifluoromethoxy, fluoromethoxy, 2,2,2-trifluoroethoxy, 1,1,2,2-tetrafluoroethoxy, etc.);

$C_{1-10}$ alkylthio (e.g., methylthio, ethylthio, n-propylthio, n-butylthio, isobutylthio, sec-butylthio, n-pentylthio, n-hexylthio, etc.);

$C_{1-10}$ haloalkylthio (e.g., trifluoromethylthio, difluoromethylthio, bromodifluoromethylthio, chlorodifluoromethylthio, fluoromethylthio, 2,2,2-trifluoroethylthio, 1,1,2,2-tetrafluoroethylthio, etc.);

$C_{2-10}$ alkoxycarbonyl (e.g., methoxycarbonyl, ethoxycarbonyl, n-propoxycarbonyl, isopropoxycarbonayl, n-butoxycarbonyl, isobutoxycarbonyl, sec-butoxycarbonyl, n-pentyloxycarbonyl, n-hexyloxycarbonyl, etc.);

phenyl; phenoxy; benzyloxy; phenoxymethyl; $C_{1-9}$ heteroaryl; ($C_{1-9}$ heteroaryl)methyloxy; ($C_{1-9}$ heteroaryl)oxymethyl; $C_{1-9}$ heteroaryloxy [wherein each of the phenyl, phenoxy, benzyloxy, phenoxymethyl, $C_{1-9}$ heteroaryl, ($C_{1-9}$ heteroaryl)methyloxy, ($C_{1-9}$ heteroaryl)oxymethyl, and $C_{1-9}$ heteroaryloxy may be substituted with one or more substituents selected from the group consisting of halogen (e.g., chlorine, etc.), $C_{1-6}$ alkyl (e.g., methyl, ethyl, etc.), $C_{1-6}$ alkoxy (e.g., methoxy, ethoxy, etc.), trifluoromethyl, and cyano; and examples of the $C_{1-9}$ heteroaryl of the $C_{1-9}$ heteroaryl, ($C_{1-9}$ heteroaryl)methyloxy, ($C_{1-9}$ heteroaryl) oxymethyl and $C_{1-9}$ heteroaryloxy include 2-pyridyl, 3-pyridyl, 4-pyridyl, 2-pyrimidinyl, 4-pyrimidinyl, 5-pyrimidinyl, 2-pyrazinyl, 3-pyridazinyl, 4-pyridazinyl, 2-thienyl, 3-thienyl, 2-furyl, 3-furyl, pyrrol-1-yl, pyrrol-2-yl, pyrrol-3-yl, 1-pyrazolyl, 3-pyrazolyl, 4-pyrazolyl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isoxazolyl, 4-isoxazolyl, 5-isoxazolyl, 1-imidazolyl, 2-imidazolyl, 4-imidazolyl, 5-imidazolyl, 1-(1,2,4-triazolyl), 3-(1,2,4-triazolyl), 4-(1,2,4-triazolyl), 2-benzothienyl, 3-benzothienyl, benzothiazol-2-yl, 2-quinolinyl, and the like];

methylenedioxy and difluoromethylenedioxy (each of the methylenedioxy and difluoromethylenedioxy is attached to the two adjacent carbon atoms of the aryl moiety);

hydroxyl; cyano; and nitro.

As the $C_{1-6}$ alkyl represented by $R^2$ and $R^{31}$, for example, there are methyl, ethyl, and the like.

As the $C_{1-6}$ alkoxy represented by $R^3$, for example, there are methoxy, ethoxy, and the like.

As the $C_{1-6}$ alkylthio represented by $R^3$, for example, there are methylthio, ethylthio, and the like.

As the halogen represented by $R^3$, for example, there are chlorine, bromine, iodine, fluorine, and the like.

As the $C_{1-6}$ alkyl represented by $R^3$, for example, there are methyl, ethyl, and the like.

As the halogen represented by $R^4$, $R^5$ and $R^6$, for example, there are chlorine, bromine, fluorine, and the like.

As the $C_{1-6}$ alkyl represented by $R^4$, $R^5$ and $R^6$, for example, there are methyl, ethyl, and the like.

As the $C_{1-6}$ alkoxy represented by $R^4$, $R^5$ and $R^6$, for example, there are methoxy, ethoxy, and the like.

As the $C_{1-6}$ haloalkyl represented by $R^4$, $R^5$ and $R^6$, for example, there are trifluoromethyl, and the like.

As the $C_{1-6}$ haloalkoxy represented by $R^4$, $R^5$ and $R^6$, for example, there are trifluoromethoxy, difluoromethoxy, bromodifluoromethoxy, chlorodifluoromethoxy, fluoromethoxy, 2,2,2-trifluoroethoxy, 1,1,2,2-tetrafluoroethoxy, and the like.

P As the $C_{2-6}$ alkoxycarbonyl represented by $R^4$, $R^5$ and $R^6$, for example, there are methoxycarbonyl, ethoxycarbonyl, and the like.

As the $C_{1-6}$ alkylthio represented by $R^4$, $R^5$ and $R^6$, for example, there are methylthio, ethylthio, and the like.

As the $C_{1-6}$ haloalkylthio represented by $R^4$, $R^5$ and $R^6$, for example, there are trifluoromethylthio, difluoromethylthio, bromodifluoromethylthio, chlorodifluoromethylthio, fluoromethylthio, 2,2,2-trifluoroethylthio, 1,1,2,2-tetrafluoroethylthio, and the like.

Specific examples of 6 membered aromatic ring containing T, U, V and W include benzene ring, pyridine ring and pyrimidine ring.

The compound of the present invention may be present in the form of its (E) isomer and (Z) isomer with respect to its C=N bond and/or C=C bond. The present invention includes both respective isomers and a mixture thereof. (The terms (E) and (Z) used herein are those used for broadly defining geometrical isomers according to Cahn-Ingold-Prelog convention.) In the compounds of the present invention, from the viewpoint of plant disease control activity, the preferred substituents are optionally substituted phenyl as $R^1$, hydrogen as $R^2$, and methoxy as $R^3$.

In the compounds of the present invention, from the viewpoint of plant disease control activity, the preferred 6-membered aromatic ring moiety containing T, U, V and W is that wherein T is CMe, U is CH, V is CH and W is CH.

Among the compounds of the present invention, from the viewpoint of plant disease control activity, examples of the preferred compounds include 5-methoxy-2-methyl-4-(2-methyl-5-phenylbenzyl)-2,4-dihydro-3H-1,2,4-triazol-3-one (the compound of the present invention No. 6), and 4-{5-(3,3-dimethyl-1-butynyl)-2-methylbenzyl}-5-methoxy-2-methyl-2,4-dihydro-3H-1,2,4-triazol-3-one (the compound of the present invention No. 526).

The compounds of the present invention can be produced according to, for example, the following Process A—Process E, and Process G. Further, the desired $R^1$ can be introduced or constructed in the final step depending upon a particular $R^1$ (e.g., Process F). In these processes, a protective group can be used for protecting a functional group from a reaction, if necessary.

As seen from the following Processes and Production Examples, among the compounds of the present invention, a part thereof, i.e., the chlorotriazoline compound represented by the formula [I-1] (Process A), the compounds represented by the formulas [I-2-1], [I-2], [I-5], [I-6], [I-5-1], [I-8], and [I-9] {Process F (Schemes 6, 7, 9, 10, and 11}, and the compound represented by the formula [I-18] {Process G (Scheme 14)} are also useful as intermediates for producing the other compounds of the present invention.

Process A: the production of the compound of the present invention wherein $R^3$ is $C_{1-6}$ alkoxy, $C_{1-6}$ alkylthio, cyano, fluorine, bromine, or iodine In this process, a chlorotriazolone compound represented by the formula [I-1]

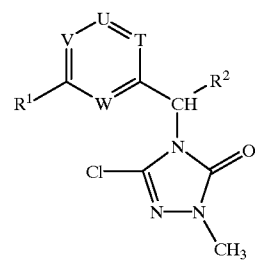

wherein $R^1$, $R^2$, T, U, V and W are as defined above, is reacted with a compound of the formula [V]

$R^{34}$-M wherein $R^{34}$ is $C_{1-6}$ alkoxy, $C_{1-6}$ alkylthio, cyano, fluorine, bromine, or iodine; and M represents an alkali metal (e.g., sodium, potassium, lithium, cesium, etc.).

Specific examples of the compound represented by the formula [V] include sodium methoxide, sodium ethoxide, sodium thiomethoxide, sodium thioethoxide, sodium cyanate, potassium cyanate, potassium fluoride, sodium bromide, etc.

Normally, the reaction temperature of this reaction is in the range of −20 to 200° C. and the reaction time is in the range of 1 to 100 hours.

Normally, in this reaction, the compound represented by the formula [V] is used at the ratio of 1 to 100 mole per 1 mole of the chlorotriazolone compound represented by the formula [I-1].

Normally, this reaction is carried out by using a solvent. Examples of the solvent include ethers such as 1,4-dioxane, tetrahydrofuran, ethylene glycol dimethyl ether, diethylene glycol dimethyl ether, diethyl ether, tert-butyl methyl ether, etc.; aliphatic hydrocarbons such as n-hexane, heptane, ligroin, petroleum ether, etc.; aromatic hydrocarbons such as toluene, xylene, etc.; alcohol such as methanol, ethanol, etc.; N,N-dimethylformamide; N,N-dimethylacetamide; dimethylsulfoxide; water, etc.; or a mixture thereof.

After completion of the reaction, the reaction U mixture can be subjected to a work-up procedure such as extraction with an organic solvent, concentration, etc. to isolate the desired compound. The compound can also be purified by recrystallization, chromatography, etc.

The chlorotriazolone compound represented by the formula [I-1] can be produced, for example, as follows (Process B).

Process B: the production of the compound of the present invention wherein $R^3$ is chlorine.

In this process, the semicarbazide compound represented by the formula [VI]

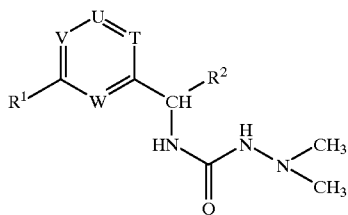

wherein $R^1$, $R^2$, T, U, V and W are as defined above, is reacted with triphosgene [bis(trichloromethyl)carbonate], diphosgene (trichloromethyl chloroformate) or phosgene.

Normally, the reaction temperature of this reaction is in the range of −20 to 150° C. and the reaction time is in the range of 1 to 100 hours.

Normally, in this reaction, triphosgene, diphosgene or phosgene is used at the ratio of 1 to 100 mole per 1 mole of the semicarbazide compound represented by the formula [VI].

If necessary, this reaction is carried out by using a solvent. Examples of the solvent include ethers such as 1,4-dioxane, tetrahydrofuran, ethylene glycol dimethyl ether, diethylene glycol dimethyl ether, tert-butyl methyl ether, etc.; aliphatic hydrocarbons such as n-hexane, heptane, ligroin, petroleum ether, etc.; aromatic hydrocarbons such as toluene, xylene, etc.; halogenated hydrocarbons such as methylene chloride, chloroform, dichloroethane, carbon tetrachloride, monochlorobenzene, etc.; or a mixture thereof.

After completion of the reaction, the reaction mixture can be subjected to a work-up procedure such as extraction with an organic solvent, concentration, etc., to isolate the desired compound. The compound can be purified by recrystallization, chromatography, etc.

The seimicarbazide compound represented by the formula [VI] can be produced by, for example, according to the following Scheme 1.

Scheme 1

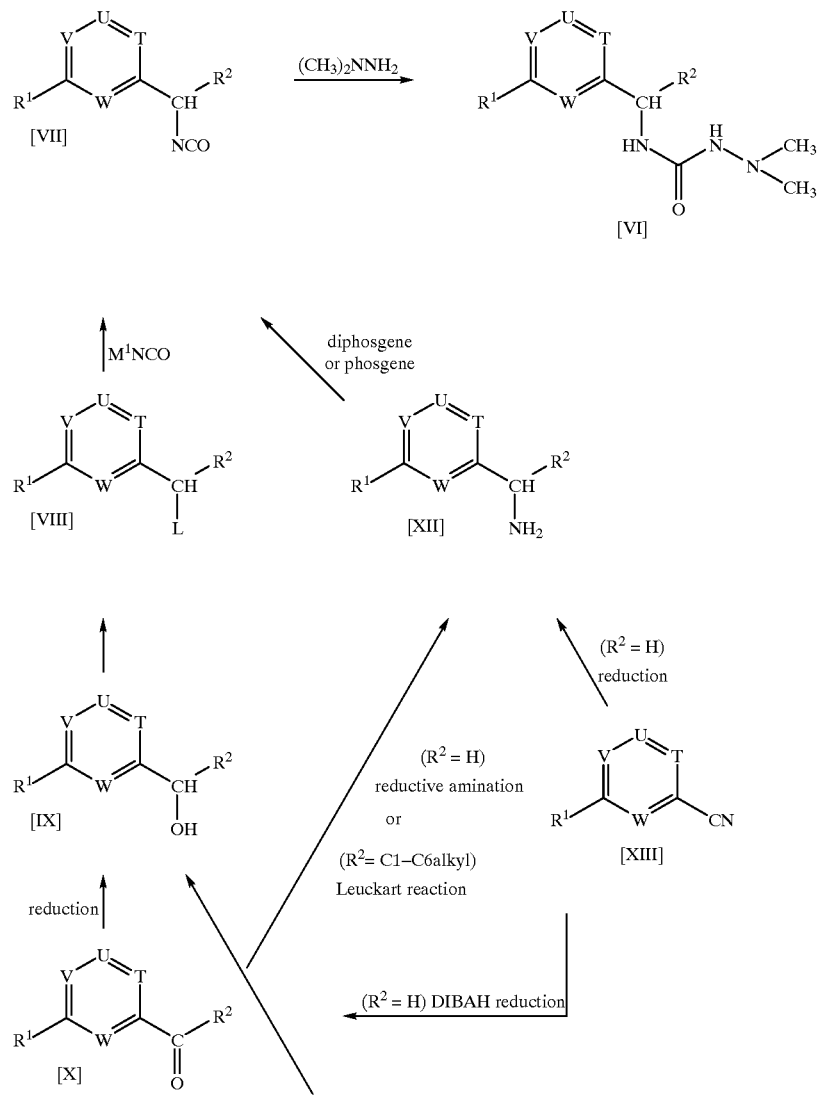

-continued

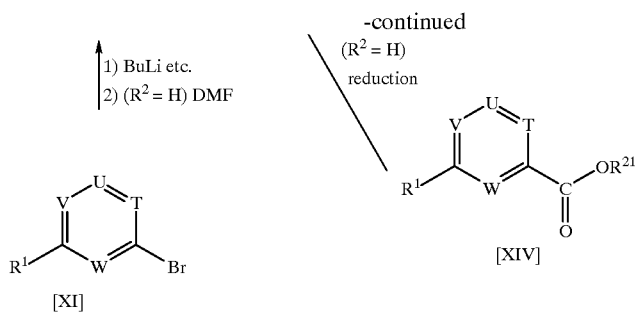

wherein $R^1$, $R^2$, T, U, V and W are as defined above; $R^{21}$ represents $C_{1-4}$ alkyl (e.g., methyl, ethyl, etc.); $M^1$ represents silver or sodium; L represents a leaving group such as chlorine, bromine, iodine, p-toluenesulfonyloxy, methanesulfonyloxy, trifluoromethanesulfonyloxy, etc.; DIBAH represents diisobutylaluminum hydride; BuLi represents butyllithium; and DMF represents N,N-dimethylformamide.

The reaction for producing the compound represented by the formula [VII] by reacting the compound represented by the formula [XII] with diphosgene or phosgene can be carried out according to, for example, the process described in J. Org. Chem., 61, 3883–3884 (1996).

Process C

In this process, a triazolone compound represented by the formula [IV]

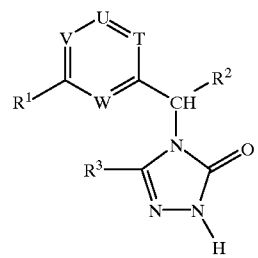

wherein $R^1$, $R^2$, $R^3$, T, U, V and W are as defined above, is reacted with a methylating agent represented by the formula [XV]

$CH_3—L^2$ wherein $L^2$ represents a leaving group such as chlorine, bromine, iodine, p-toluenesulfonyloxy, methanesulfonyloxy, trifluoromethanesulfonyloxy, $OSO_2OCH_3$, etc.

Normally, this reaction is carried out in the presence of a base. Examples of the base to be used include inorganic bases such as sodium hydride, sodium hydroxide, potassium hydroxide, sodium carbonate, potassium carbonate, etc.

Normally, the reaction temperature of this reaction is in the range of −20 to 150° C. and the reaction time is in the range of 1 to 100 hours.

Normally, in this reaction, the methylating agent represented by the formula [XV] and the base are used at the ratios of 1 to 5 mole, and 1 to 10 mole per 1 mole of the triazolone compound represented by the formula [IV], respectively.

If necessary, this reaction can be carried out by using a solvent. Examples of the solvent include ethers such as 1,4-dioxane, tetrahydrofuran, ethylene glycol dimethyl ether, diethylene glycol dimethyl ether, tert-butyl methyl ether, etc.; aliphatic hydrocarbons such as n-hexane, heptane, ligroin, petroleum ether, etc.; aromatic hydrocarbons toluene, xylene, etc.; organic bases such as pyridine, triethylamine, N-methylaniline, N,N-dimethylaniline, N,N-diethylaniline, etc.; nitrites such as acetonitrile, isobutyronitrile, etc.; N,N-dimethylformadmide; dimethylsulfoxide; water; etc., or a mixture thereof.

After completion of the reaction, the reaction mixture can be subjected to a work-up procedure such as extraction with an organic solvent, concentration, etc. to isolate the desired compound. This compound can also be purified by recrystallization, chromatography, etc.

The triazolone compound of the formula [IV] can be produced, for example, by the process according to the following Scheme 2.

Scheme 2

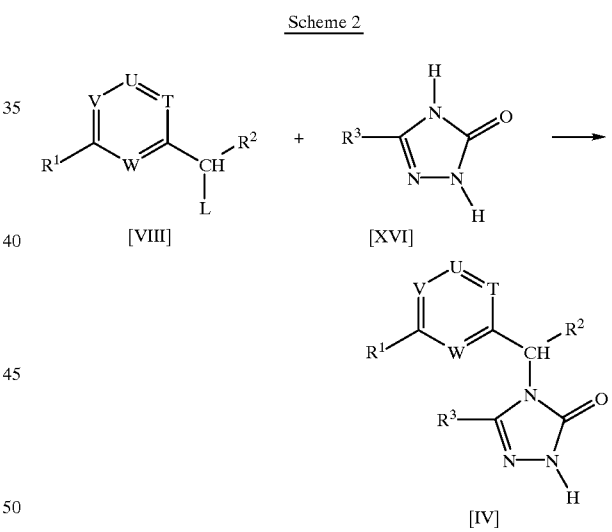

wherein $R^1$, $R^2$, $R^3$, T, U, V, W and L are as defined above.

Normally, this reaction is carried out in the presence of a base (e.g., sodium hydride, sodium hydroxide, potassium hydroxide, sodium carbonate, potassium carbonate, etc.).

The compound represented by the formula [XVI] is a known compound described in, for example, JP 8-325244 A; J. Chem. Soc. Perkin I, 2644–2646 (1973); Chem. Ber. 102, 755–766 (1969); Chem. Ber. 98, 3025–3033 (1965), etc., or it can be produced according to the process described therein, or it can be produced from the compound described therein.

Among the triazolone compounds represented by the formula [IV], those wherein $R^3$ is $C_{1-6}$ alkyl or cyclopropyl can be produced according to the process of the following Scheme 3.

Scheme 3

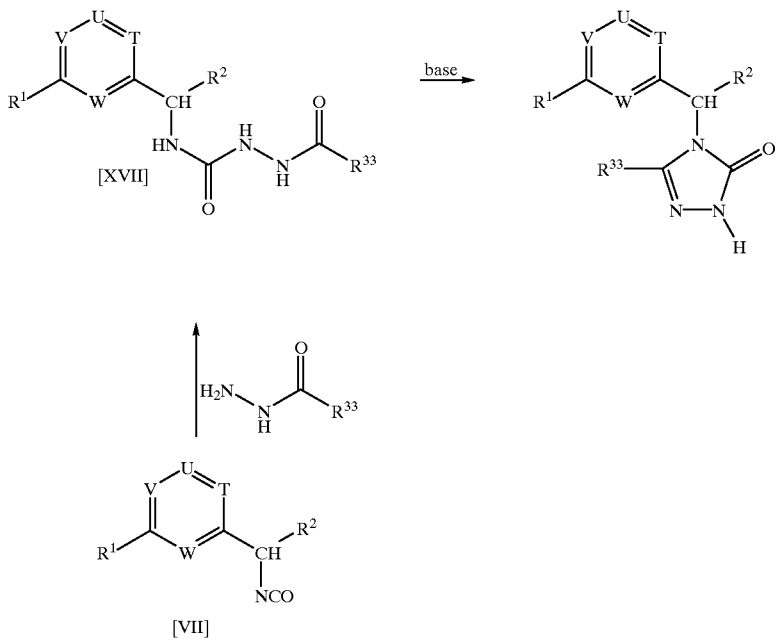

wherein R³³ represents $C_{1-6}$ alkyl (e.g., methyl, ethyl, etc.) or cyclopropyl; and $R^1$, $R^2$, T, U, V and W are as defined above. Examples of the base include an aqueous solution of potassium hydroxide, etc.

Process D

In this process, a compound represented by the formula [II]

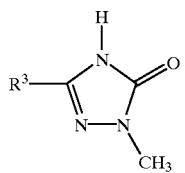

wherein $R^3$ is as defined above (including the alkoxytriazolone compound represented by the formula [II-1]), is reacted with the compound represented by the formula [VIII] in Scheme 1.

Normally, this reaction is carried out in the presence of a base. Examples of the base include inorganic bases such as sodium hydroxide, potassium hydroxide, sodium carbonate, potassium carbonate, sodium hydride, etc.; organic bases such as pyridine, 2-picoline, 4-picoline, 4-dimethylaminopyridine, quinoline, triethylamine, ethyldiisopropylamine, N, N-dimethylaniline, N, N-diethylaniline, etc.; or a mixture thereof.

Normally, the reaction temperature of this reaction is in the range of –20 to 150° C. and the reaction time is in the range of 1 to 100 hours.

Normally, in this reaction, the compound represented by the formula [VIII] and the base are used at the ratios of 0.5 to 2 mole, and 0.5 to 4 mole per 1 mole of the triazolone represented by the formula [II], respectively.

If necessary, this reaction can be carried out by using a solvent. The solvent is selected according to the base used and examples of the solvent include ethers such as 1,4-dioxane, tetrahydrofuran, ethylene glycol dimethyl ether, diethylene glycol dimethyl ether, tert-butyl methyl ether, etc.; aliphatic hydrocarbons such as n-hexane, heptane, ligroin, petroleum ether, etc.; aromatic hydrocarbons such as toluene, xylene, etc.; organic bases such as pyridine, triethylamine, N-methylaniline, N,N-dimethylaniline, N,N-diethylaniline, etc.; nitrites such as acetonitrile, isobutyronitlie, etc.; N,N-dimethylformamide; dimethylsulfoxide; water; etc., or a mixture thereof.

After completion of the reaction, the reaction mixture can be subjected to a work-up procedure such as extraction with an organic solvent, concentration, etc. to isolate the desired compound. This compound can also be purified by recrystallization, chromatography, etc.

The triazolone represented by the formula [II] is a known compound described in, for example, Chem. Ber. 102, 755–766 (1969); Chem. Ber. 98, 3025–3033 (1965); etc., or it can be produced by the process described therein or the method described in JP 8-325244 A, or it can be produced from the compound described therein.

The alkoxytriazolone compound represented by the formula [II-1] can be produced, for example, according to the following Scheme 4.

Scheme 4

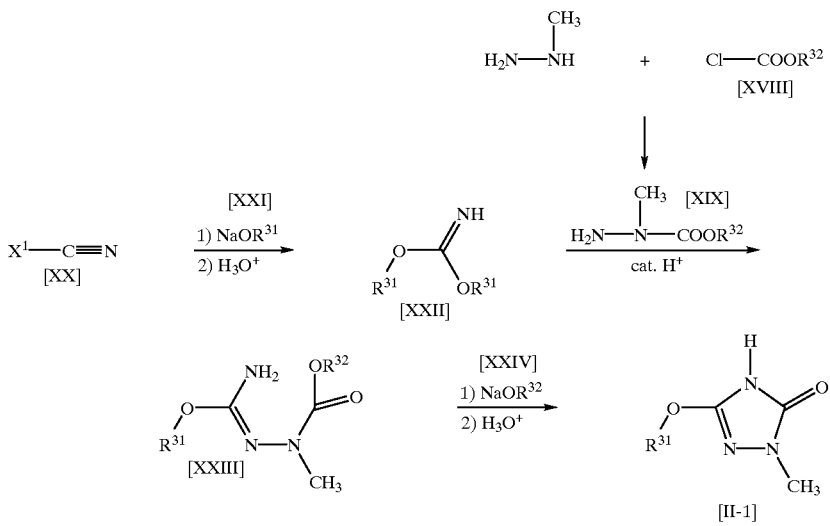

wherein $X^1$ represents bromine or chlorine; $R^{31}$ is as defined above, $R^{32}$ represents $C_{1-6}$ alkyl (e.g., methyl, ethyl, etc.).

That is, the alkoxytriazolone compound represented by the formula [II-1] can be produced by cyclizing the isosemicarbazide compound represented by the formula [XXIII] or a tautomer compound thereof normally at 20 to 150° C. normally in the presence of sodium alkoxide represented by the formula [XXIV] (e.g., sodium methoxide, sodium ethoxide, etc.), followed by treatment with an acid (e.g., hydrochloric acid, etc.).

The isosemicarbazide compound represented by the formula [XXIII] can be produced by reacting the dialkyl iminocarbonate represented by the formula [XXII] with carbazate derivative represented by the formula [XIX] normally at −20 to 120° C. normally in the presence of a catalyst (e.g., protonic acid such as hydrochloric acid, sulfuric acid, phosphoric acid, carbonic acid, acetic acid, propionic acid, pivalic acid, methanesulfonic acid, etc.).

For example, the dialkyl iminocarbonate represented by the formula [XXII] can be produced by reacting a cyanogen halide represented by the formula [XX] (cyanogen bromide or cyanogen chloride) with sodium alkoxide represented by the formula [XXIV] (e.g., sodium methoxide, sodium ethoxide, etc.) normally at −20 to 50° C., followed by treatment with an acid (e.g., hydrochloric acid, etc.).

The carbazate derivative represented by the formula [XIX] can be produced by reacting alkyl chlorocarbonate represented by the formula [XVIII] with methyl hydrazine normally at −20 to 50° C., if necessary, in the presence of acid trapping agent.

Process E: the production of the compound of the present invention wherein $R^3$ is $C_{1-6}$ alkyl or cyclopropyl In this process, the compound represented by the formula [XXV]

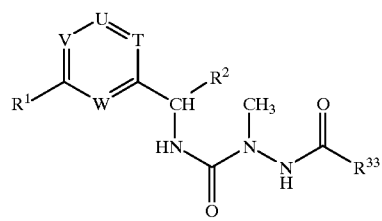

wherein $R^1$, $R^2$, $R^{33}$, T, U, V and W are as defined above is cyclized and dehydrated.

Normally, this reaction is carried out in the presence of a base and examples of the base include inorganic bases such as potassium hydroxide, sodium hydroxide, etc.

Normally, the reaction temperature of this reaction is in the range of −20 to 150° C. and the reaction time is in the range of 1 to 100 hours.

Normally, in this reaction, the base is used at the ratio of 1 to 10 mole per 1 mole of the compound represented by the formula [XXV].

If necessary, this reaction can be carried out by using a solvent. Examples of the solvent include water; ethers such as 1,4-dioxane, tetrahydrofuran, ethylene glycol dimethyl ether, diethylene glycol dimethyl ether, tert-butyl methyl ether, etc.; aliphatic hydrocarbons such as n-hexane, heptane, ligroin, petroleum ether, etc.; aromatic hydrocarbons such as toluene, xylene, etc.; or a mixture thereof.

After completion of the reaction, if necessary, the reaction mixture can be acidified and then subjected to a work-up procedure such as extraction with an organic solvent, concentration, etc. to isolate the desired compound. The compound can also be purified by recrystallization, chromatography, etc.

The compound represented by the formula [XXV] can be produced, for example, according to the following process of Scheme 5.

Scheme 5

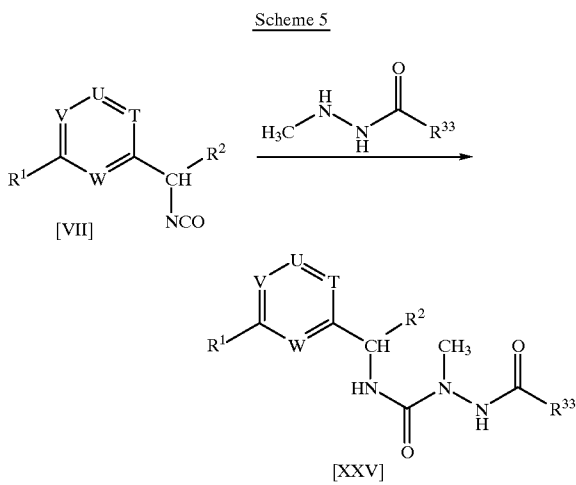

wherein $R^1$, $R^2$, $R^{31}$, T, U, V and W are as defined above.

Process F

For example, there are the following F-1 to F-6.

F-1

This is the process according to Scheme 6.

Scheme 6

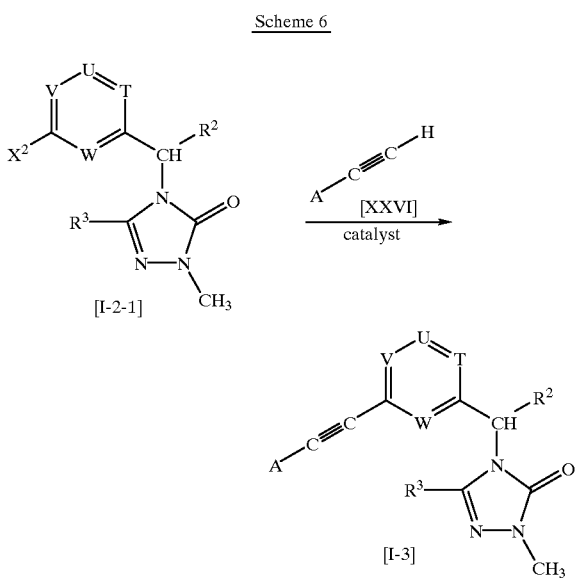

wherein $X^2$ represents bromine or iodine; $R^2$, $R^3$, T, U, V and W are as defined above; and the group represented by the formula A—C≡C—H represents optionally substituted $C_{2-10}$ alkynyl having the triple bond at its terminal, and A represents the residue thereof; the substituent of the $C_{2-10}$ alkynyl includes that of the above optionally substituted $C_{2-10}$ alkynyl represented by $R^1$.

This reaction can be carried out in the presence of a base [for example, a tertiary amine (e.g., triethylamine, diisopropylethylamine, etc.), a secondary amine (diethylamine, etc.), a primary amine (e.g., butylamine, etc.) or the like] and a catalyst [for example, a palladium catalyst (e.g. palladium (II) acetate, tetrakis(triphenylphosphine) palladium (0), bis(triphenylphosphine)palladium (II) dichloride ($PdCl_2(PPh_3)_2$, etc.) and, if necessary, copper (I) iodide and triphenylphosphine, etc.] in an aprotic polar solvent (e.g., acetonitrile, N,N-dimethylformamide, etc.) [more specifically, according to the method described in Example 1 of WO98/03464, that described in Tetrahedron Lett., 1975, 4467, that described in Synthesis, 1980, 627, or the like].

F-2

This is the process according to Scheme 7.

Scheme 7

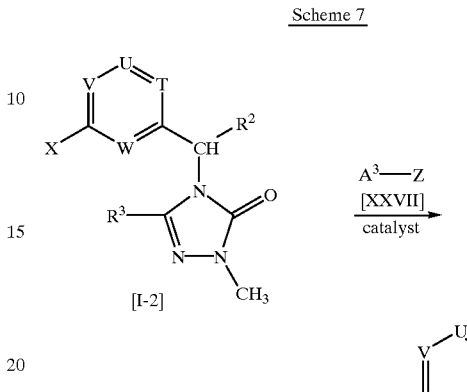

wherein X represents bromine, iodine, chlorine or trifluoromethanesulfonyl; Z represents $B(OR^{14})$ or $SnR^{15}{}_3$; $R^{15}$ represents $C_{1-4}$ alkyl (e.g., methyl, ethyl, butyl, etc.); $A^3$ represents optionally substituted $C_{6-10}$ aryl or optionally substituted $C_{1-9}$ heteroaryl; and $R^2$, $R^3$, $R^{14}$, T, U, V and W are as defined above.

Normally, the reaction temperature is in the range of 20 to 120° C., the reaction time is in the range of 1 to 24 hours and the compound represented by the formula [XXVI] is used at the ratio of 0.8 to 5 mole per 1 mole of the compound represented by the formula [I-2].

Normally, this reaction is carried out by using 0.001 to 0.1 mole of the catalyst per 1 mole of the compound represented by the formula [I-2]. Examples of the catalyst include palladium catalysts such as palladium (II) acetate, tetrakis(triphenylphosphine) palladium (0), {1,1'-bis(diphenylphosphino)ferrocene}dichloropalladium (II) methylene chloride complex, tris(dibenzylidene acetone)-(chloroform)-di-palladium (0) [$Pd_2(dba)_3CHCl_3$], bis(triphenylphosphine)palladium (II) dichloride, etc.

If necessary, this reaction can also be carried out in the presence of a base (e.g., inorganic bases such as sodium acetate, potassium acetate, potassium carbonate, cesium carbonate, tripotassium phosphate, sodium bicarbonate, etc.), a phase-transfer catalyst (e.g., quaternary ammonium salts such as tetrabutylammonium bromide, benzyltriethylammonium bromide, etc.), a ligand (e.g., tri-tert-butylphosphine, etc.). Further, in case the compound represented by the formula [XXVII] wherein Z is $SnR^{15}{}_3$, copper (II) oxide, silver (I) oxide, etc. can be used as a co-catalyst.

Normally, the reaction is carried out in a solvent. Examples of the solvent include alcohol solvents such as methanol, ethanol, propanol, butanol, isopropanol, etc.; ether solvents such as 1,4-dioxane, tetrahydrofuran, ethylene glycol dimethyl ether, t-butyl methyl ether, etc.; aliphatic hydrocarbon solvents such as n-hexane, n-heptane, etc.; aromatic hydrocarbon solvents such as toluene, etc.; nitrile solvents such as acetonitrile, etc.; N,N-dimethylformamide; dimethylsulfoxide; water; etc., or a mixture thereof.

More specifically, this reaction can be carried out according to the process described in J. Org. Chem., 1997, 62, 7170–7173 [carried out in water in the presence of tetrabutylammonium bromide, a base (e.g., inorganic base such as potassium carbonate, etc.) and a catalyst (e.g., palladium (II) acetate, etc.)]; the process described in Beispiel 2 of WO96/35669 [carried out in a mixture of water and dimethoxyethane in the presence of a base (e.g., inorganic base such as sodium bicarbonate, etc.) and a catalyst (e.g., Pb(PPh$_3$)$_4$, etc.)]; the process described in J. Org. Chem., 1995, 60, 7508–7510; the process described in Angew. Chem. Int. Ed., 1998, 37 (24), 3387–3388; the process described in Angew. Chem. Int. Ed. Engl., 1986, 25, 508–524: or the like.

After completion of the reaction, the reaction mixture can be subjected to a conventional work-up procedure such as extraction with an organic solvent, concentration, etc. to obtain the desired compound. If necessary, the desired compound can be purified by recrystallization, chromatography, etc.

The compound represented by the formula [XXVII] is commercially available, or it can be produced by, for example, the process of the following Scheme 8.

Scheme 8

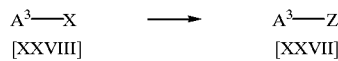

wherein A$^3$, X and Z are as defined above.

specifically, carried out according to, for example, the process described in Organometallics, 1983, 2, 1316; Liebigs Ann., 1996, 1037; Jikken Kagaku Koza, 4th Ed., Vol. 24, Organic Synthesis VI, p 80, Maruzen;, J. Am. Chem., Soc., 1958, 80, 4291–4293); a process wherein the compound represented by the formula [XXVIII] is reacted with bis (pinacolate)diborone in a solvent (e.g., dimethylsulfoxide, N,N-dimethylformamide, etc.) in the presence of a base (e.g., inorganic base such as potassium acetate, etc.) and a catalyst (e.g., {1,1'-bis(diphenyphosphono) ferrocene}dichloropalladium (II) methylene chloride complex, etc.), if necessary, followed by hydrolysis (more specifically, carried out according to, for example, the process described in J. Org. Chem., 1995, 60, 7508–7510); a process wherein the compound represented by the formula [XXVIII] is reacted with R$^{15}$$_3$SnSnR$^{15}$ (e.g., Bu$_3$SnSnBu$_3$, etc.) in a solvent (e.g., toluene, etc.) in the presence of a catalyst (e.g., tetrakis(triphenylphosphine)-palladium (0), etc.) (more specifically, carried out according to, for example, the process described in Chem. Letters, 1981, 829–830); or the like.

After completion of the reaction, the reaction mixture can be subjected to a conventional work-up procedure such as extraction with an organic solvent, concentration, etc. to obtain the desired compound. If necessary, the desired compound can be purified and isolated by recrystallization, distillation, chromatography, etc.

F-3

This is the process according to the following Scheme 9.

Scheme 9

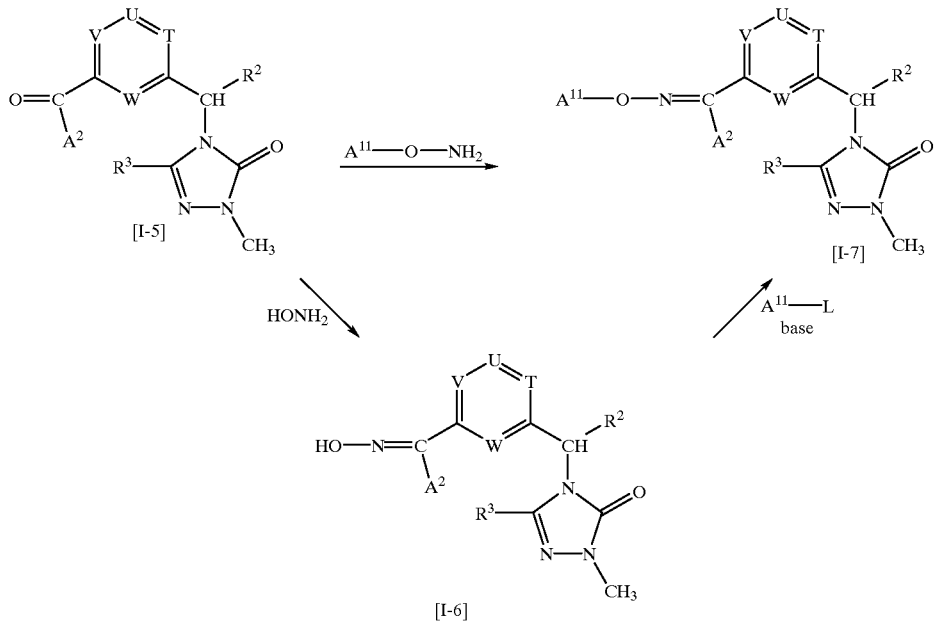

For example, the reaction can be carried out by a process wherein a Grignard reagent or organic lithium compound obtained by reacting the compound represented by the formula [XXVIII] with a metal (e.g., magnesium, lithium, etc.) or an organic lithium reagent (e.g., tert-butyllithium, n-butyllithium, lithium diisopropylamide, etc.) in a solvent (e.g., diethyl ether, tetrahydrofuran etc.) is reacted with a borate (e.g., trimethyl borate, triethyl borate, triisopropyl borate, etc.), if necessary, followed by hydrolysis (more wherein A$^{11}$ represents A$^1$ other than hydrogen, and A$^1$, A$^2$, R$^2$, R$^3$, L, T, U, V and W are as defined above.

Among the compounds represented by the formula [I-5], that wherein A$^2$ is methyl can be produced according to, for example, the process described in J. Org. Chem., 1992, 57, 1481–1486 by reacting the compound represented by the formula [I-2] with butyl vinyl ether in the presence of a palladium catalyst, a phosphine ligand and a base, followed by acid hydrolysis.

F-4
This is the process according to the following Scheme 10.
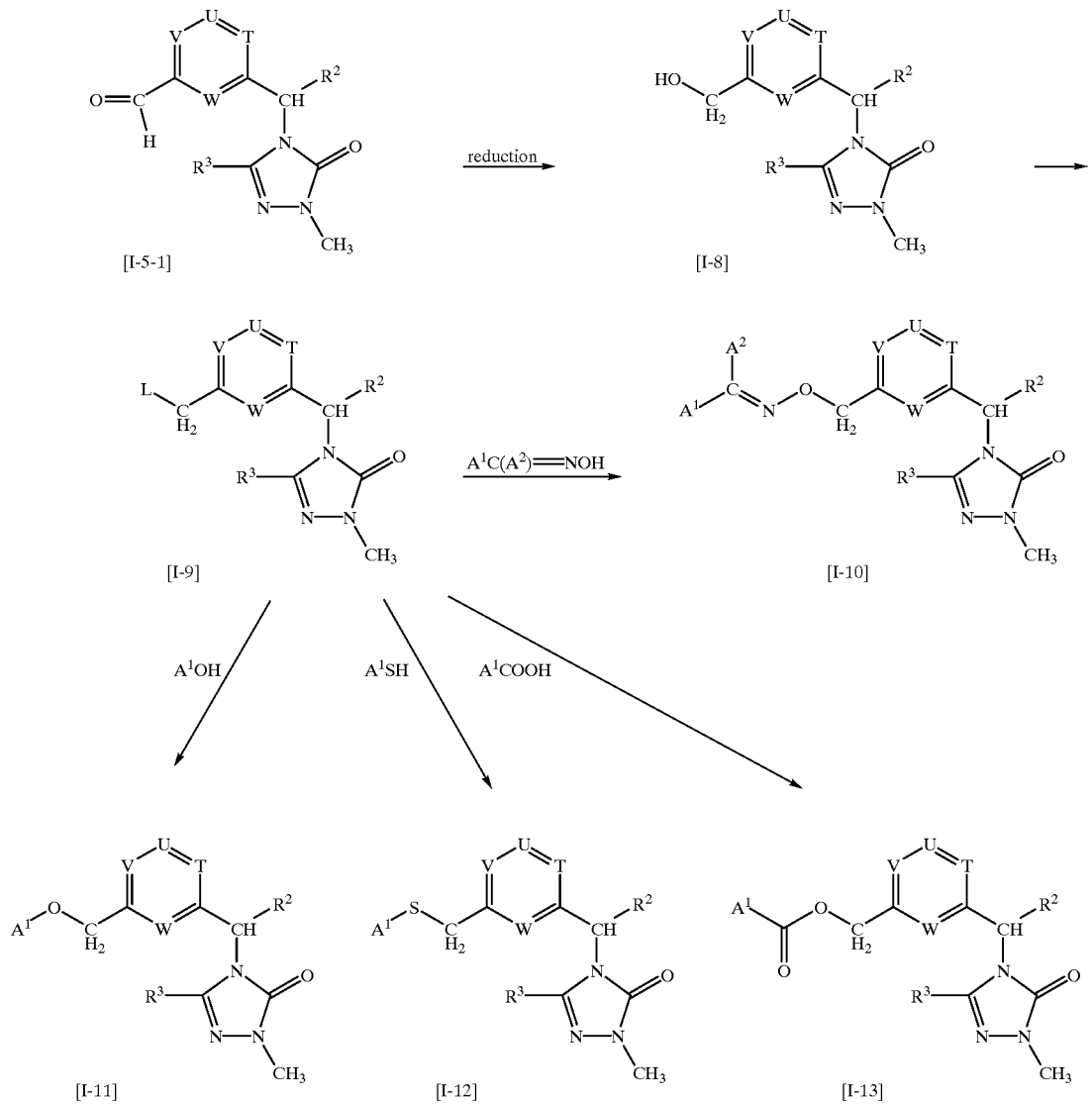
wherein $A^1$, $A^2$, $R^2$, $R^3$, L, T, U, V and W are as defined above.
F-5
This is the process according to the following Scheme 11.
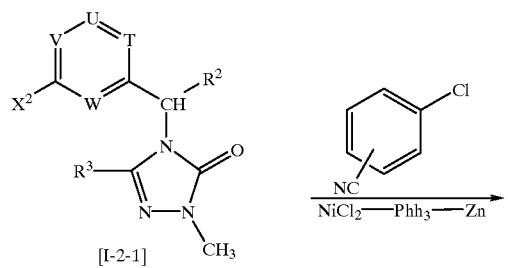
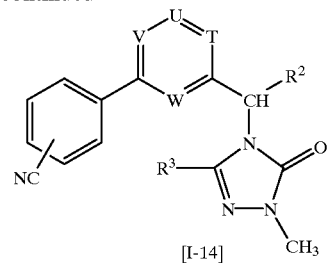
wherein $X^2$, $R^2$, $R^3$, T, U, V and W are defined above.
This reaction can be carried out according to, for example, the process described in Synlett, 1994, 371–372.

F-6
This is the process according to the following Scheme 12.

Scheme 12

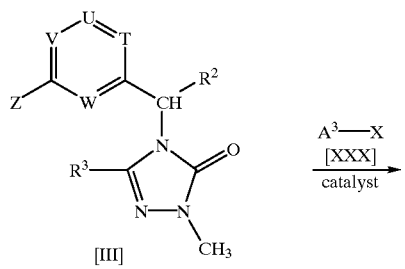

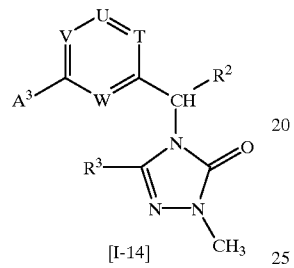

wherein $A^3$, X, Z, $R^2$, $R^3$, T, U, V and W are as defined above.

Normally, the reaction temperature is in the range of 20 to 120° C., the reaction time is in the range of 1 to 24 hours, and the compound represented by the formula [XXX] is used at the ratio of 1 to 5 mole per 1 mole of the compound represented by the formula [III].

Normally, in this reaction, the catalyst is used at the ratio of 0.001 to 0.1 mole per 1 mole of the compound represented by the formula [III]. Examples of the catalyst include palladium (II) acetate, tetrakis(triphenylphosphine) palladium (0), {1,1'-bis(diphenylphosphino) ferrocene}dichloro-palladium (II) methylene chloride complex, tris(dibenzylideneacetone)-(chloroform)-di-palladium (0) [$Pd_2(dba)_3CHCl_3$], bis(triphenylphosphine) palladium (II) dichloride, etc.

If necessary, this reaction can also be carried out in the presence of a base (e.g., inorganic bases such as sodium acetate, potassium acetate, potassium carbonate, cesium carbonate, tripotassium phosphate, sodium bicarbonate, etc.), a phase-transfer catalyst (e.g., quaternary ammonium salts such as tetrabutylammonium bromide, benzyltriethylammonium bromide, etc.), a ligand (e.g., tri-tert-butylphosphine, etc.). Further, in case the compound represented by the formula [XXX] wherein $A^3$ is $SnR^{15}_3$, copper (II) oxide, silver (I) oxide, etc. can be used as a co-catalyst.

Normally, the reaction is carried out in a solvent. Examples of the solvent include alcohol solvents such as methanol, ethanol, propanol, butanol, isopropanol, etc..; ether solvents such as 1,4-dioxane, tetrahydrofuran, ethylene glycol dimethyl ether, t-butyl methyl ether, etc.; aliphatic hydrocarbon solvents such as n-hexane, n-heptane, etc.; aromatic hydrocarbon solvents such as toluene, etc.; nitrile solvents such as acetonitrile, etc.; N,N-dimethylformamide; dimethylsulfoxide; water; etc., or a mixture thereof.

More specifically, this reaction can be carried out according to the process described in J. Org. Chem., 1997, 62, 7170–7173 [carried out in water in the presence of tetrabutylammonium bromide, a base (e.g., inorganic base such as potassium carbonate, etc.) and a catalyst (e.g., palladium (II) acetate, etc.)]; the process described in Beispiel 2 of WO96/35669 [carried out in a mixture of water and dimethoxyethane in the presence of a base (e.g., inorganic base such as sodium bicarbonate, etc.) and a catalyst (e.g., $Pb(PPh_3)_4$, etc.)]; the process described in J. Org. Chem., 1995, 60, 7508–7510; the process described in Angew. Chem. Int. Ed., 1998, 37 (24), 3387–3388; the process described in Angew. Chem. Int. Ed. Engl., 1986, 25, 508–524: or the like.

After completion of the reaction, the reaction mixture can be subjected to a conventional work-up procedure such as extraction with an organic solvent, concentration, etc. to obtain the desired compound. If necessary, the desired compound can be purified and isolated by recrystallization, distillation, chromatography, etc.

The compound represented by the formula [III] can be produced by the process represented by the following Scheme 13.

Scheme 13

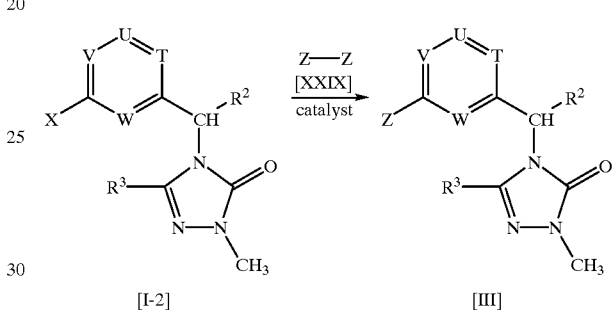

wherein X, Z, $R^2$, $R^3$, T, U, V and W are as defined above.

In the reaction of Scheme 3, normally, the reaction temperature is in the range of 20 to 100° C., the reaction time is in the range of 1 to 24 hours and the compound represented by the formula [XXIX] is used at the ratio of 1 to 5 mole pre 1 mole of the compound represented by the formula [I-2].

For example, this reaction can be carried out by a process wherein the compound represented by the formula [I-2] is reacted with bis(pinacolate)diborone, etc. in a solvent (e.g., dimethylsulfoxide, N,N-dimethylformamide, etc.) in the presence of a base (e.g., inorganic base such as potassium acetate, etc.) and a catalyst (e.g., {1,1'-bis (diphenyphosphono)ferrocene}dichloropalladium (II) methylene chloride complex, etc.) (more specifically, carried out according to, for example, the process described in J. Org. Chem., 1995, 60, 7508–7510); a process wherein the compound represented by the formula [I-2] is reacted with $R^{15}_3SnSnR^{15}$ (e.g., $Bu_3SnSnBu_3$, etc.) in a solvent (e.g., toluene, etc.) in the presence of a catalyst (e.g., tetrakis (triphenylphosphine)-palladium (0), etc.) (more specifically, carried out according to, for example, the process described in Chem. Letters, 1981, 829–830); or the like. Further, in case of the compound represented by the formula [III] wherein Z is $B(OR^{14})_2$ and $R^{14}$ is $C_{1-6}$ alkyl, for example, the reaction can be carried out by a process wherein a Grignard reagent or organic lithium compound obtained by reacting the compound represented by the formula [I-2] with a metal (e.g., magnesium, lithium, etc.) or an organic lithium reagent (e.g., tert-butyllithium, n-butyllithium, lithium diisopropylamide, etc.) in a solvent (e.g., diethyl ether, tetrahydrofuran etc.) is reacted with a tri-$C_{1-6}$ aklyl borate (e.g., trimethyl borate, triethyl borate, triisopropyl borate, etc.), if necessary, followed by hydrolysis (more. specifically, carried out according to, for example, the process described in Organometallics, 1983, 2, 1316; Liebigs Ann., 1996, 1037; Jikken Kagaku Koza, 4th Ed., Vol. 24, Organic Synthesis VI, p 80, Maruzen; J. Am. Chem., Soc., 1958, 80, 4291–4293).

After completion of the reaction, the reaction mixture can be subjected to a conventional work-up procedure such as extraction with an organic solvent, concentration, etc. to obtain the desired compound. If necessary, the desired compound can be purified by recrystallization, chromatography, etc.

Process G

This process is carried out according to the following Scheme 14.

wherein TMS represents trimethylsilyl; and X, $R^1$, $R^2$, T, U, V and W are as defined above. Examples of the dehydrating agent include acetic anhydride, etc. Examples of the reducing agent include Lindlar catalyst, etc. Examples of the strong base include butyllithium, etc. Examples of the catalyst include palladium catalysts such as palladium (II) acetate, tetrakis(triphenylphosphine)palladium (0), bis(triphenylphosphine)palladium (II) dichloride ($PdCl_2(PPh_3)_2$), etc. and, if necessary, copper (I) iodide and triphenylphosphine, etc.

The compound represented by the formula [XXXI] in Scheme 14, can be produced according to, for example, the following Scheme 15.

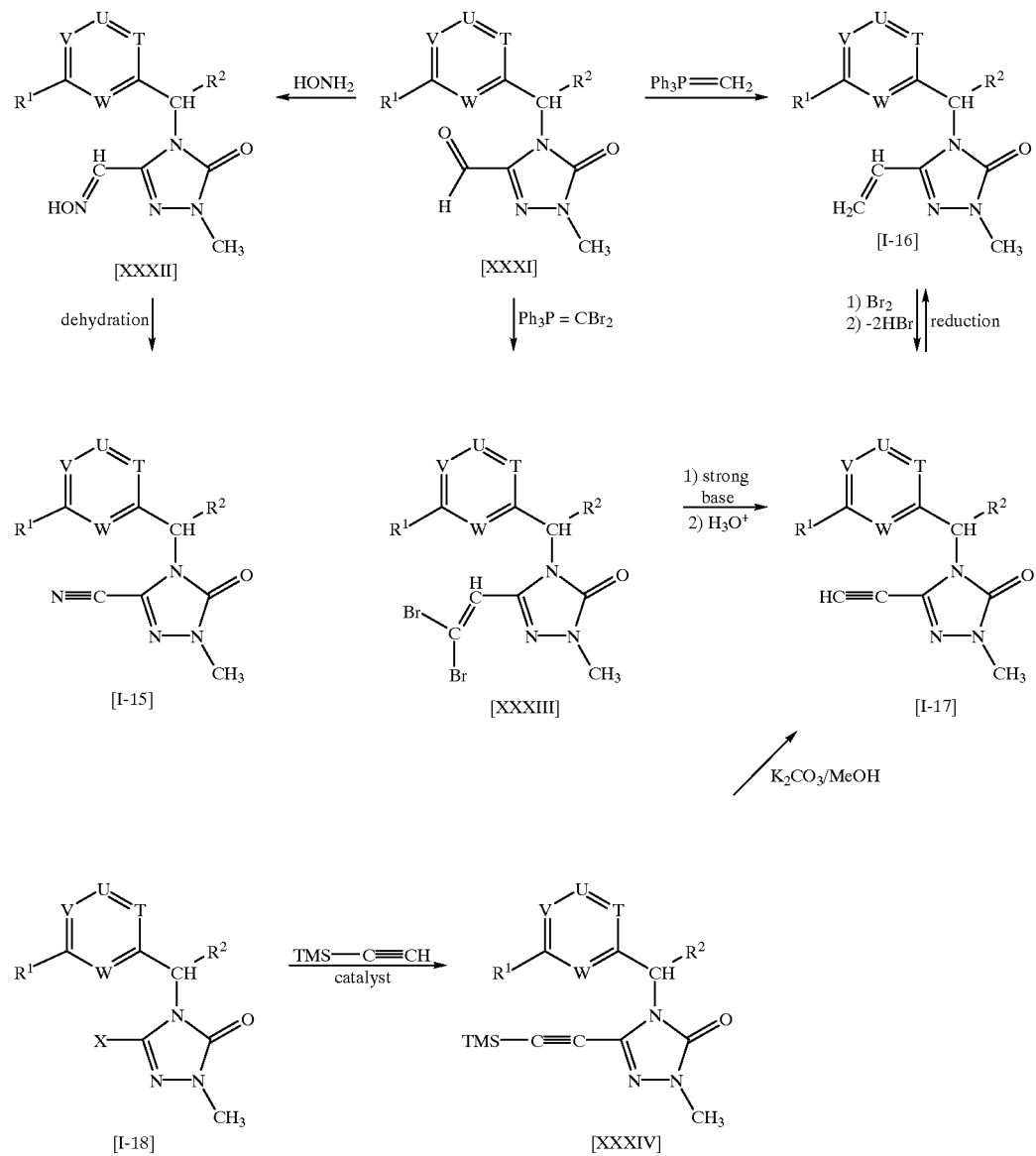

Scheme 14

Scheme 15

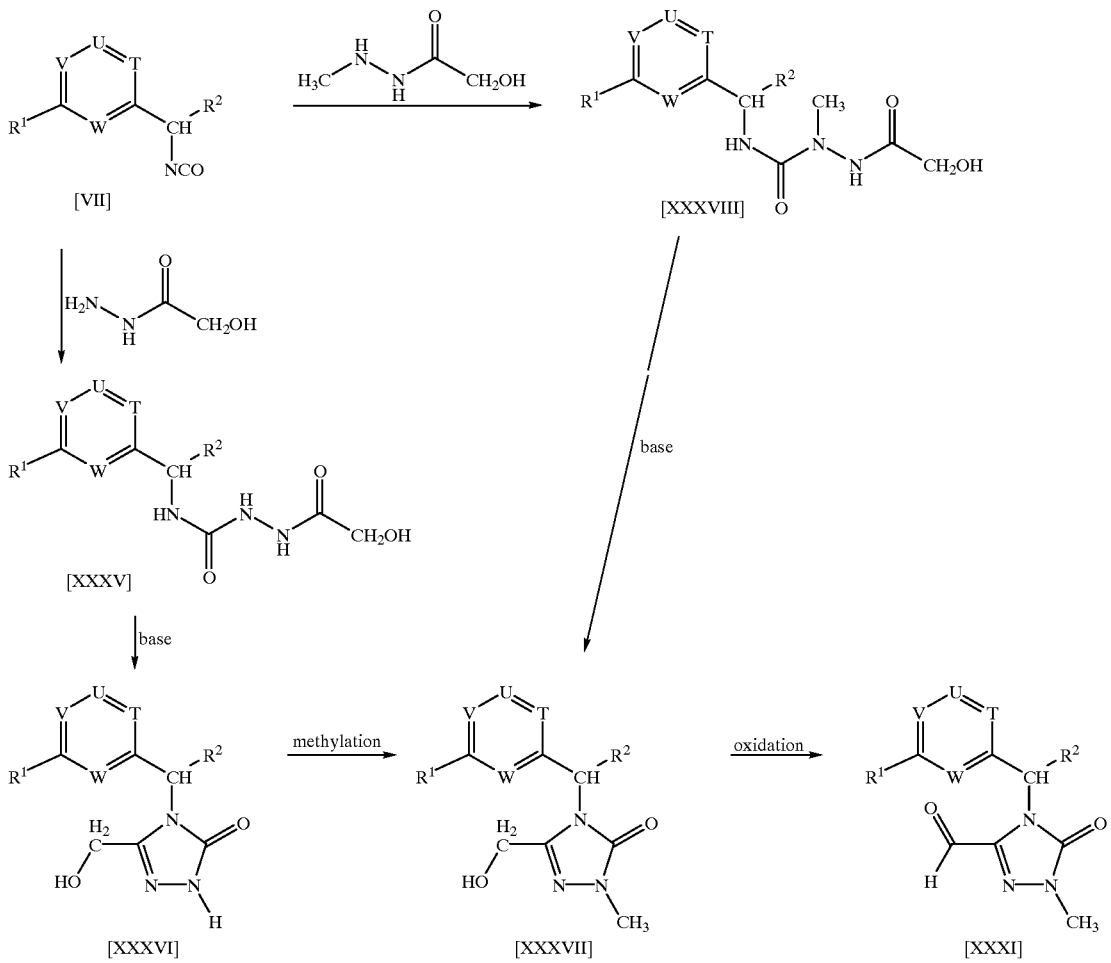

wherein $A^3$, $L^1$, X, Y, $R^6$, $R^7$ and $R^8$ are as defined above. Examples of the base include an aqueous solution of potassium hydroxide, etc. Examples of the methylating agent include methyl iodide-potassium carbonate, etc. Examples of the oxidizing agent include maganese dioxide, etc.

When the compound of the present invention is used as an active ingredient of an agricultural or horticultural fungicide composition, it can be used as it is without addition of any other ingredient. However, normally, it is used in admixture with solid or liquid carriers, surfactants and other supplemental agents into conventional formulations such as emulsifiable concentrates, wettable powders, suspensions, water-dispersible granules, emulsions, dusts, granules, powders, granules, and the like. These formulations normally contain as an active ingredient 0.1 to 90% by weight of the compound of the present invention based on the total weight of the formulations.

Examples of the solid carrier to be used for such formulations include finely divided powder or granules of kaolin clay, attapulgite clay, bentonite, terra alba, pyrophyllite, talc, diatomaceous earth, calcite, corn rachis powder, walnut shell powder, urea, ammonium sulfate, synthesized hydrous silicon hydroxide, etc. Examples of the liquid carrier include aromatic hydrocarbons such as xylene, methylnaphthalene, etc.; alcohol such as isopropanol, ethylene glycol, Cellosolve™, etc.; ketones such as acetone, cyclohexanone, isophorone, etc.; vegetable oils such as soybean oil, cottonseed oil, etc.; dimethylsulfoxide; acetonitrile; water; etc.

Examples of the surfactant include anion surfactants such as alkylsulfate salts, aklylarylsulfonate salts, dialkylsulfosuccinate salts, salts of phosphates of polyoxyethylene alkylaryl ethers, naphthlenesulfonate formalin condensate, etc.; nonionic surfactants such as polyoxyethylene alkyl ethers, polyoxyethylene alkyl polyoxypropylene block copolymers, sorbitan fatty acid esters. etc.; and the like.

Examples of the supplemental agent include ligninsulfonates, alginates, polyvinyl alcohol, gum arabic, carboxymethyl cellulose (CMC), isopropyl acid phosphate (PAP), etc.

The compound of the present invention can be applied by foliar application, soil treatment, seed disinfection, etc. as well as any other commonly utilized application method.

When the compound of the present invention is used as an active ingredient of an agricultural or horticultural fungicide composition, the dosage thereof is varied depending upon a particular kind of subject plant (crop, etc.), kind of objective plant disease, degree of disease, formulation type, application timing, weather conditions, etc. However, normally, the dosage is 0.01 to 50 g, preferably, 0.05 to 10 g per 1 are.

In case of applying emulsifiable concentrates, wettable powders, suspensions, emulsions, or the like by diluting it with water, the dosage concentration thereof is 0.0001 to 3%, preferably 0.0005 to 1%. The dusts, granules, etc. are applied as they are without dilution.

The compound of the present invention can be used as an agricultural or horticultural fungicide for fields, paddy fields, orchards, tea gardens, meadows, lawns and the like, and it is expected to enhance its fungicidal activity by using in admixture with other agricultural or horticultural fungicides. Examples of the other agricultural or horticultural fungicides which can be admixed with the compound of the present invention include azole fungicide compounds such as propiconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, flutoriafol, etc.; cyclic amine fungicide compounds such as fenpropimorph, tridemorph, fenpropidin, etc.; benzimidazole fungicide compounds such as carbendazim, benomyl, thiabendazole, thiophanate-methyl, etc.; procymidone; cyprodinil; pyrimethanil; diethofencarb; thiram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; N-methyl-α-methoxyimino-2-[(2,5-dimethylphenoxy)methyl] phenylacetamide, spiroxamine; quinoxyfen; fenhexamid; fenamidone (RP-407213); iprovalicarb; and the like.

The compound of the present invention can also be used in admixture with or together with other agricultural or horticultural insecticides, acaricides, nematocides, herbicides, plant growth regulators, and fertilizers.

Examples of such insecticides and/or acaricides and/or nematocides include organic phosphorous compounds such as fenitrothion [O,O-dimethyl O-(3-methyl-4-nitrophenyl) phosphorothioate], fenthion [O,O-dimethyl O-(3-methyl-4-(methylthio)phenyl)phosphorothioate], diazinon [O,O-diethyl O-2-isopropyl-6-methylpyridin-4-ylphosphorothioate], chlorpyrifos [O,O-diethyl O-3,5,6-trichloro-2-pyridylphosphorothioate], acephate [O,S-dimethylacetyl-phosphoramidothioate], methidathion [S-2,3-dihydro-5-methoxy-2-oxo-1,3,4-thiadiazol-3-ylmethyl O,O-dimethylphosphorothioate], disulfoton [O,O-diethyl S-2-ethylthioethylphosphorothioate], DDVP [2,2-dichlorovinyl-dimethylphosphate], sulprofos [O-ethyl O-4-(methylthio) phenyl S-propylphosphorodithioate], cyanophos [O-4-cyanophenyl O,O-dimethylphosphorothioate], dioxabenzofos [2-methoxy-4H-1,3,2-benzodioxaphosphinyn-2-sulfide], dimethoate [O,O-dimethyl S-(N-methylcarbamoylmethyl)-dithiophosphate], phenthoate [ethyl 2-dimethoxyphosphino-thioylthio (phenyl)acetate], malathion [diethyl (dimethoxyphosphinothioylthio)succinate], trichlorphon [dimethyl 2,2,2-trichloro-1-hydroxyehtylphosphpnate], azinphos-methyl [S-3,4-dihydro-4-oxo-1,2,3-benzotriazin-3-ylmethyl O,O-dimethylphosphorodithioate], monocrotophos [dimethyl(E)-1-methyl-2-(methylcarbamoyl) vinylphosphate], ethion [O,O,O',O'-tetraethyl S,S'-methylenebis-(phosphorodithioate)], fosthiazate [N-(O-methyl-S-sec-butyl)phosphorylthiazolidin-2-one], etc.; carbamate compounds such as BPMC [2-sec-butylphenylmethylcarbamate], benfuracarb [ethyl N-(2,3-dihydro-2,2-dimethylbenzofuran-7-yloxycarbonyl(methyl) aminothio]-N-isopropyl-β-alaninate], propoxur [2-isopropoxyphenyl N-methylcarbamate], carbosulfan [2,3-dihydro-2,2-dimethyl-7-benzo[b]furanyl N-dibutylaminothio-N-methylcarbamate], carbaryl [1-naphthyl N-methylcarbamate], methomyl [S-methyl-N-[(methylcarbamoyl)oxy]thioacetoimidate], ethiofencarb [2-(ethylthiomethyl)phenylmethylcarbamate], aldicarb [2-methyl-2-(methylthio)propionaldehyde O-methylcarbamoyloxime], oxamyl [N,N-dimethyl-2-methylcarbamoyloxyimino-2-(methylthio)acetamide], fenothiocarb [S-4-phenoxybutyl-N,N-dimethylthiocarbamate], etc.; pyrethroid compounds such as ethofenprox [2-(4-ethoxyphenyl)-2-methylpropyl-3-phenoxybenzylether], fenvalerate [(RS)-α-cyano-3-phenoxybenzyl (RS)-2-(4-chlorophenyl)-3-methylbutyrate], esfenvalerate [(S)-α-cyano-3-phenoxybenzyl (S)-2-(4-chlorophenyl)-3-methylbutyrate], fenpropathrin [(RS)-α-cyano-3-phenoxybenzyl 2,2,3,3-tetramethylcyclopropanecarboxylate], cypermethrin [(RS)-α-cyano-3-phenoxybenzyl (1RS,3RS)-3-(2,2-dichlorovinyl)-2,2-dimethylcyclopropanecarboxylate], permethrin [3-phenoxybenzyl (1RS, 3RS)-3-(2,2-dichlorovinyl)-2,2-dimethylcyclopropanecarboxylate], cyhalothrin {(RS)-α-cyano-3-phenoxybenzyl (Z)-(1RS, 3RS)-3-(2-chloro-3,3,3-trifluoropropenyl)-2,2-dimethylcyclopropanecarboxylate], deltamethrin [(S)-α-cyano-m-phenoxybenzyl (1R,3R)-3-(2,2-dibromovinyl)-2,2-dimethylcyclopropanecarboxylate], cycloprothrin [(RS)-α-cyano-3-phenoxybenzyl (RS)-2,2-dichloro-1-(4-ethoxyphenyl)cyclopropanecarboxylate], fluvalinate [α-cyano-3-phenoxybenzyl N-(2-chloro-α,α,α-trifluoro-p-tolyl)-D-valinate], bifenthrin [2-methylbiphenyl-3-ylmethyl (Z)-(1RS)-cis-3-(2-chloro-3,3,3-trifluoroprop-1-enyl)-2,2-dimethylpropanecarboxylate], acrinathrin [(1R-{1α(S*),3α (Z)}]-2,2-dimethyl-3-[3-oxo-3-(2,2,2-trifluoro-1-(trifluoromethyl)ethoxy-1-propenyl]cyclopropanecarboxlic acid cyano(3-phenoxyphenyl)methyl ester)], 2-methyl-2-(4-bromodifluoromethoxyphenyl)propyl(3-phenoxybenzyl) ether, tralomethrin [(S)-α-cyano-3-phenoxybenzyl (1R)-cis-3-(1,2,2,2-tetrabromoethyl)-2,2-dimethylcyclopropanecarobxylate], silafluofen [[4-ethoxyphenyl(3-(4-fluoro-3-phenoxyphenyl)propyl)-dimethylsilane]], etc.; thiadiazine derivatives such as buprofezin [(2-tert-butylimino-3-isopropyl-5-phenyl-1,3,5-triadiazinan-4-one)], etc.; nitroimidazolidine derivatives; cartap [(S,S'-(2-dimethylaminotrimethylene)-bis (thiocarbamate)], nereistoxin derivatives such as thiocyclam {N,N-dimethyl-1,2,3-trithian-5-ylamine], bensultap [S,S'-2-dimethylaminotrimethylene di(benzenethiosulfonate)], etc.; N-cyanoamidine derivatives such as N-cyano-N'-methyl-N'-(6-chloro-3-pyridylmethyl)acetamidine, etc.; chlorinated hydrocarbon compounds such as endosulfan [6,7,8,9,10,10-hexachloro-1,5,5a,6,9,9a-hexahydro-6,9-methano-2,4,3-benzodioxathepinoxide], gamma-BHC [1,2,3,4,5,6-hexachlorocyclohexane], 1,1-bis(chlorophenyl)-2,2,2-trichloroethanol], etc.; benzoylphenylurea compounds such as chlorflazuron [1-(3,5-dichloro-4-(3-chloro-5-trifluoromethylpyridin-2-yloxy)phenyl)-3-(2,6-difluorobenzoyl)urea], teflubenzuron [1-(3,5-dichloro-2,4-difluorophenyl)-3-(2,6-difluorobenzoyl)urea], flufenoxuron [1-(4-(2-chloro-4-trifluoromethylphenoxy)-2-fluorophenyl)-3-(2,6-difluorobenzoyl)urea], etc.; formamidine derivatives such as amitraz [N,N'-[(methylimino) dimethylidine] di-2,4-xylidine], chlordimeform [N'-(4-chloro-2-methylphenyl)-N,N-dimethylmethanimidamide], etc.; thiourea derivatives such as diafenthiuron [N-(2,6-diisopropyl-4-phenoxyphenyl)-N'-tert-butylcarbodiimide], etc.; phenylpyrazole compounds; tebufenozide [N-tert-butyl-N'-(4-ethylbenzoly)-3,5-dimethylbenzohydrazide]; 4-bromo-2-(4-chlorophenyl)-1-ethoxymethyl-5-trifluoromethylpyrrol-3-carbonitrile; bromopropylate [isopropyl 4,4'-dibromobenzylate]; tetradifon

[4-chlorophenyl 2,4,5-trichlorophenyl sulfone]; quinomethionate [S,S-6-methylquinoxalin-2,3-diyldithiocarbonate]; propargite [2-(4-tert-butylphenoxy)cyclohexylprop-2-yl sulfite]; fenbutatin oxide [bis[tris(2-methyl-2-phenylpropyl)tin]oxide]; hexythiazox [(4RS,5RS)-5-(4-chlorophenyl)-N-chlorohexyl-4-methyl-2-oxo-1,3-thiazolidin-3-carboxamide]; clofentezine [3,6-bis(2-chlorophenyl)-1,2,4,5-tetrazine]; pyridaben [2-tert-butyl-5-(4-tert-butylbenzylthio)-4-chloropyridazin-3(2H)-one]; fenpyroximate [tert-butyl (E)-4-[(1,3-dimethyl-5-phenoxypyrazol-4-yl)methyleneaminoxymethyl]benzoate], tebufenpyrad [N-(4-tert-butylbenzyl)-4-chloro-3-ethyl-1-methyl-5-pyrrazolcarboxamide]; polynactin complex [tetranactin, dinactin, trinactin]; milbemectin; avermectin; ivermectin, azadirachtin [AZAD]; pyrimidifen [5-chloro-N-[2-{4-(2-ethoxyethyl)-2,3-dimethylphenoxy}-ethyl]-6-ethylpyrimidin-4-amine]; pymetrozine [2,3,4,5-tetrahydro-3-oxo-4-[(pyridin-3-yl)-methyleneamino]-6-methyl-1,2,4-triazine; and the like.

Examples of the plant diseases against which the compounds of the present invention exhibit controlling effects are as shown below.

rice plant: blast (*Pyricularia oryzae*), brown spot of rice plant (*Cochliobolus miyabeanus*), sheath blight (*Rhizoctonia solani*);

wheat, barley, etc.: powdery mildew (*Erysiphe graminis*), scab (*Gibberella zeae*), rust (*Puccinia struiformis, P. graminis, P. recondita, P. hordei*), snow blight (Typhula sp., *Micronectriella nivalis*), loose smut (*Ustilago tritici, U. nuda*), bunt (*Tilletia caries*), eye spot (*Pseudocercosporella herpotrichoides*), scald (*Rhynchosporium secalis*), specked leaf blotch (*Septoria tritici*), glume blotch (*Leptosphaeria nodorum*);

citrus: melanose (*Diaporthe citri*), scab (*Elsinoe fawcetti*), fruit rot (*Penicillium digitatum, P. italicum*);

apple: blossom blight (*Sclerotinia mali*), canker (*Valsa mali*), powdery mildew (*Podosphaera leucotricha*), Alernaria blotch (*Alternaria mali*), scab (*Venturia inaequalis*);

pear: scab (*Venturia nashicola, V. pirina*), black spot (*Alernaria kikuchiana*), rust (*Gymnosporangium haraeanum*);

peach: brown rot (*Sclerotina cinerea*), (*Cladosporium carpophilum*), Phomopsis rot (Phomopsis sp.);

grape: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), downy mildew (*Plasmopare viticola*);

persimmon: anthracnoce (*Gloeosporium kaki*), leaf spot (*Cercospora kaki, Mycosphaerella newae*);

cucumber, melon, etc.: anthracnose (*Colletotrichum lagenarium*), powdery mildew (*Sphaerotheca fuliginea*), gummy stem blight (*Mycosphaerella melonis*), Fusarium wilt (*Fusarium oxysporum*), downy mildew (*Pseudoperonospora cubensis*), late blight (Phytophthora sp.), damping-off (Pythium sp.);

tomato: early blight (*Alternaria solani*), leaf mold (*Cladosporium fulvum*), late blight (*Phytophthora infestans*);

eggplant: brown spot (*Phomopsis vexans*), powdery mildew (*Erysiphe cichoracearum*);

Cruciferae vegetable: Alternaria leaf spot (*Alternaria japonica*), white spot (*Cercosporella brassicae*);

Welsh onion: rust (*Puccinia allii*);

soybean: purple stain (*Cercospora kikuchii*), Sphaceloma scab (*Elsinoe glycines*), pod and stem blight (*Diaporthe phaseolorum* var. sojae);

kidney bean: anthracnose (*Colletotrichum lindemthianum*);

peanut: leaf spot (*Cercospora personata*), brown leaf spot (*Cercospora arachidicola*);

pea: powdery mildew (*Erysiphe pisi*);

potato: early blight (*Alernaria solani*), late blight (*Phytophthora infestans*);

strawberry: powdery mildew (*Sphaerotheca humuli*);

tea: net blister blight (*Exobasidium reticulatum*), white scab (*Elsinoe leucospila*);

tobacco: brown spot (*Alternaria longipes*), powdery mildew (*Erysiphe cichoracearum*), anthracnose (*Colletotrichum tabacum*), downy mildew (*Peronospora tabacina*), late blight (*Phytophthora nicotianae*);

beet: Cercisoira leaf spot (*Cercospora beticola*);

rose: black spot (*Diplocarpon rosae*), powdery mildew (*Sphaerotheca pannosa*);

chrysanthemum: leaf blight (*Septoria chrysanthemi-indici*), rust (*Puccinia horiana*);

various crops: gray mold (*Botrytis cinerea*), stem rot (*Sclerotinia sclerotiorum*); and the like.

The following Production Examples, Formulation Examples and Test Examples further illustrate the present invention in detail but are not construed to limit the scope of the present invention.

First, Production Examples (including Production Examples of the triazolone compounds, the intermediate compounds represented by the formula [IV]: Reference Production Examples 4, 5, 6, 10, 11, 12, 13, 16, 17 and 18) will be set forth. Compound Nos. of the present invention are those shown in Tables 1 to 23 hereinafter.

PRODUCTION EXAMPLE 1

To a solution of 300 mg (1.0 mmol) of 5-chloro-2-methyl-4-(3-phenylbenzyl)-2,4-dihydro-3H-1,2,4-triazol-3-one (the compound 2 of the present invention, produced in the following Production Example 2) in 10 ml of dry methanol was added 0.85 g (4.4 mmol) of sodium methoxide (28% methanol solution) and the resultant mixture was heated under reflux for 3.5 hours. After allowing to cool to room temperature, water was added to the reaction mixture, followed by extraction with ethyl acetate. The organic layer was washed with water, dried and concentrated. The residue was subjected to silica gel preparative thin layer chromatography (developed with n-hexane:ethyl acetate=1:1) to obtain 0.24 g (0.81 mmol) of 5-methoxy-2-methyl-4-(3-phenylbenzyl)-2,4-dihydro-3H-1,2,4-triazol-3-one (the compound 1 of the present invention).

$^1$H-NHR (CDCl$_3$, TMS)

δ (ppm): 7.3–7.6 (9H, m), 4.76 (2H, s), 3.95 (3H, s), 3.38 (3H, s)

PRODUCTION EXAMPLE 2

To a solution of 2.75 g (9.28 mmol) of triphosgene in 15 ml of methylene chloride was added dropwise a solution of 1.25 g (4.64 mmol) of 1,1-dimethyl-4-(3-phenylbenzyl) semicarbazide (produced in the following Reference Production Example 1) in 10 ml of methylene chloride with ice-cooling. The mixture was removed from an ice bath, allowed to warm to room temperature, and heated under reflux for 4 hours. After allowing to cool to room temperature, the reaction mixture was poured into an about 5% aqueous solution of sodium bicarbonate, and the mixture was stirred for 1 hour. The organic layer was washed with water, dried and concentrated. The residue was subjected to silica gel column chromatography (eluted with n-hexane:ethyl acetate=5:1 and then 3:1) to obtain 0.59 g (2.0 mmol) of 5-chloro-2-methyl-4-(3-phenylbenzyl)-2,4-dihydro-3H-1,2,4-triazol-3-one (the compound 2 of the present invention).

$^1$H-NHR(CDCl$_3$, TMS)

δ (ppm): 7.3–7.6 (9H, m), 4.91 (2H, s), 3.47 (3H, s)

Reference Production Example 1

(1) To a solution of 22.84 g (95.0 mmol) of 3-bromobiphenyl in 280 ml of dry tetrahydrofuran was added 61 ml (99.8 mmol) of n-butyllithium (1.64 mol/liter, n-hexane solution) at −70 ° C. under an atmosphere of nitrogen. The mixture was stirred at the same temperature for 1 hour, and to this was added dropwise 36.55 g (0.50 mol) of N,N-dimethylformamide. The resultant mixture was stirred overnight, while being slowly warmed to room temperature. To the reaction solution was added 400 ml of about 5% aqueous hydrochloric acid, and the mixture was stirred for 2 hours at room temperature. The mixture was extracted with tert-butyl methyl ether, and the organic layer was washed with an about 5% aqueous solution of sodium bicarbonate and water, then dried and concentrated. The residue was subjected to silica gel column chromatography (eluted with n-hexane, then n-hexane:ethyl acetate=15:1) to obtain 13.95 g (76.56 mmol) of 3-phenylbenzaldehyde.

$^1$H-NMR(CDCl$_3$, TMS)

δ (ppm): 10.09(1H, s), 7.3–8.1(9H, m)

(2) To a solution of 5.47 g (30 mmol) of 3-phenylbenzaldehyde in 50 ml of dry methanol and 50 ml of dry tetrahydrofuran was added 1.34 g (32 mmol) of sodium borohydride portionwise with ice-cooling, and further the mixture was stirred for 1 hour with ice-cooling. The reaction mixture was added to 400 ml of an about 5% aqueous solution of ammonium chloride, and the mixture was extracted with tert-butyl methyl ether. The organic layer was dried and concentrated to obtain 5.57 g (30 mmol) of 3-phenylbenzylalcohol.

$^1$H-NMR(CDCl$_3$, TMS)

δ (ppm): 7.3–7.7(9H, m), 4.75(2H, br d), 1.75(1H, br t)

(3) To a solution of 5.57 g (30 mmol) of 3-phenylbenzylalcohol in n-hexane was added dropwise 4.06 g (13.5 mmol) of phosphorous tribromide with ice-cooling. The mixture was removed from an ice bath and stirred at room temperature for 3.5 hours. To the reaction mixture were added ice water and tert-butyl methyl ether and the mixture was stirred for 30 minutes and separated. The organic layer was washed twice with water, dried and concentrated to obtain 6.62 g (26.8 mmol) of 3-phenylbenzylbromide.

$^1$H-NMR(CDCl$_3$, TMS)

δ (ppm): 7.3–7.65 (9H, m), 4.56 (2H, s)

(4) To a solution of 2.47 g (10 mmol) of 3-phenylbenzylbromide in 30 ml of dry tetrahydrofuran was added 1.99 g (13 mmol) of silver cyanate. The reaction mixture was heated under reflux for 2 hours and filtered. The filtrate was concentrated to obtain 2.56 g of crude 3-phenylbenzylisocyanate.

$^1$H-NMR(CDCL$_3$, TMS)

δ (ppm): 7.25–7.65 (9H, m), 4.56 (2H, s)

To a solution of 2.56 g of this crude 3-phenylbenzylisocyanate in 8 ml of toluene was added dropwise 0.78 g (13 mmol) of N,N-dimethylhydrazine with ice-cooling. The mixture was removed from an ice bath and stirred for 1.5 hours. The reaction mixture was concentrated and the residue was subjected to silica gel column chromatography (eluted with n-hexane:ethyl acetate=1:1 and then 1:2) to obtain 1.40 g (5.20 mmol) of 1,1-dimethyl-4-(3-phenylbenzyl)semicarbazide.

$^1$H-NMR(CDCl$_3$, TMS)

δ (ppm): 7.25–7.65 (9H, m), 6.45 (1H, br), 5.10 (1H, br), 4.53 (2H, d), 2.51 (6H, s)

PRODUCTION EXAMPLE 3

To a solution 193 mg (0.52 mmol) of 5-chrolo-2-methyl-4-{3-(1-(benzyloxyimino)ethyl)benzyl}-2,4-dihydro-3H-1,2,4-triazol-3-one (the compound 249 of the present invention, produced in the following Production Example 4) was added 0.20 g (1.0 mmol) of sodium methoxide (28% methanol solution). The resultant mixture was heated under reflux for 3 hours. To this was added 0.20 g (1.0 mmol) of sodium methoxide (28% methanol solution) and the mixture was heated under reflux for 3 hours. After allowing to cool to room temperature, water was added to the reaction mixture and it was extracted with ethyl acetate. The organic layer was washed with water, dried and concentrated. The residue was subjected to silica gel preparative thin layer chromatography (developed with n-hexane:ethyl acetate=1:1) to obtain 141 mg (0.385 mmol) of 5-methoxy-2-methyl-4-{3-(1-(benzyloxyimino)ethyl)benzyl}-2,4-dihydro-3H-1,2,4-triazol-3-one (the compound 239 of the present invention).

$^1$H-NMR(CDCl$_3$, TMS)

δ (ppm): 7.25–7.65 (9H, m), 5.24 (2H, s), 4.71 (2H, s), 3.92 (3H, s), 3.37 (3H, s), 2.25 (3H, s)

PRODUCTION EXAMPLE 4

To a solution of 0.96 g (3.24 mmol) of triphosgene in 10 ml of dry methylene chloride was added dropwise a solution of 0.55 g (1.62 mmol) of 1,1-dimethyl-4-{3-(1-(benzyloxyimino)ethyl)benzyl}semicarbazide (produced in the following Reference Production Example 2) in 15 ml of dry methylene dhloride with ice-cooling. The mixture was removed from an ice bath, then allowed to warm to room temperature and heated under reflux for 4 hours. After allowing to cool to room temperature, the reaction mixture was poured into 40 ml of an about 5% aqueous solution of sodium bicarbonate, and the mixture was stirred for 0.5 hours. The organic layer was washed with water, dried and concentrated. The residue was subjected to silica gel preparative thin layer chromatography (developed with n-hexane:ethyl acetate=3:2) to obtain 0.27 g (0.74 mmol) of 5-chloro-2-methyl-4-{3-(1-(benzyloxyimino)ethyl)-benzyl}-2,4-dihydro-3H-1,2,4-triazol-3-one (the compound 249 of the present invention).

$^1$H-NMR(CDCl$_3$, TMS)

δ (ppm): 7.25–7.65 (9H, m), 5.24 (2H, s), 4.86 (2H, s), 3.46 (3H, s), 2.25 (3H, s)

Reference Production Example 2

(1) To a suspension of 14.52 g (0.10 mol) of 3-acetylbenzonitrile in 100 ml of methanol was added 17.56 g (0.11 mol) of O-benzylhydroxyamine hydrochloride and further added dropwise 9.49 g (0.12 mol) of pyridine. The mixture was stirred at room temperature for 2.5 hours, and most of the methanol was distilled off. To the residue was added ethyl acetate and resultant mixture was washed successively with about 5% aqueous hydrochloric acid twice, an about 5% aqueous solution of sodium bicarbonate once, and water once, then dried and concentrated to obtain 24.15 g (95.0 mmol) of crude 3-(1-(benzyloxyimino)ethyl)benzonitrile.

¹H-NMR(CDCl₃, TMS)

δ (ppm): 7.25–8.0 (9H, m), 5.25 (2H, s), 2.26 (3H, s)

To a solution of 24.15 g (95.0 mmol) of crude 3-(1-(benzyloxyimino)ethyl)benzonitrile in 1 liter of dry toluene was added 77.3 ml (116 mmol) of diisobutylaluminum hydride (1.5 mol/toluene solution) at −70° C. or below under an atmosphere of nitrogen, and the mixture was stirred overnight with gradually warming to room temperature. To the reaction mixture was added 200 ml of an about 20% aqueous solution of ammonium chloride, and the mixture was stirred at room temperature for 0.5 hours. Then, 400 ml of an about 5% aqueous solution of sulfuric acid was add thereto with ice-cooling. The mixture was stirred at the same temperature for 0.5 hours and then stirred at room temperature for 6 hours. The reaction mixture was separated and the aqueous layer was extracted with tert-butyl methyl ether. The organic layers were combined and washed twice with water, then dried and concentrated. The residue was subjected to silica gel column chromatography (eluted with n-hexane:toluene=1:1 and then 1:2) to obtain 18.26 g (72.1 mmol) of 3-(1-(benzyloxyimino)ethyl)benzoaldehyde.

¹H-NMR(CDCl₃, TMS)

δ (ppm): 10.04 (1H, s), 7.25–8.15 (9H, m), 5.27 (2H, s), 2.31 (3H, s)

(2) To a solution of 9.92 g (39.17 mmol) of 3-(1-(benzyloxyimino)ethyl)benzaldehyde in 70 ml of dry methanol and 70 ml of dry tetrahydrofuran was added 1.81 g (43 mmol) of sodium borohydride portionwise with ice-cooling, and the mixture was stirred for 2 hours with ice-cooling. Further, 0.30 g of sodium borohydride portionwise was added thereto with ice-cooling, and the mixture was stirred for 2 hours with ice-cooling. The reaction mixture was poured into 500 ml of an about 5% aqueous solution of ammonium chloride, and the mixture was extracted with tert-butyl methyl ether. The organic layer was dried and concentrated to obtain 9.64 g (37.8 mmol) of 3-(1-(benzyloxyimino)ethyl)benzylalcohol.

¹H-NMR(CDCl₃, TMS)

δ (ppm): 7.25–7.7 (9H, m), 5.25 (2H, s), 4.73 (2H, br d), 2.28 (3H, s), 1.72 (1H, br t)

(3) To a solution of 2.55 g (10 mmol) of 3-(1-(benzyloxyimino)ethyl)benzylalcohol in 20 ml of dry diethyl ether was added dropwise 1.35 g (4.5 mmol) of phosphorous tribromide with ice-cooling. The mixture was removed from an ice bath and stirred at room temperature for 6 hours. To the reaction mixture were added ice water and diethyl ether. The mixture was stirred for 30 minutes and separated. The organic layer was washed successively with an about 5% aqueous solution of sodium bicarbonate and water, then dried and concentrated to obtain 2.78 g (8.74 mmol) of 3-(1-(benzyloxyimino)ethyl)benzylbromide.

¹H-NMR(CDCl₃, TMS)

δ (ppm): 7.25–7.70 (9H, m), 5.25 (2H, s), 4.51 (2H, s), 2.27 (3H, s)

(4) To a solution of 2.78 g (8.74 mmol) of 3-(1-(benzyloxyimino)ethyl)benzylbromide in 30 ml of dry tetrahydrofuran was added 1.74 g (11.4 mmol) of silver cyanate and the mixture was heated under reflux for 3 hours. Further, 1.74 g (11.4 mmol) of silver cyanate was added thereto, and the mixture was heated under reflux for 2 hours. Furthermore, 1.74 g (11.4 mmol) of silver cyanate was added thereto, and the mixture was heated under reflux for 2 hours. The reaction mixture was filtered, and the filtrate was concentrated to obtain 2.75 g of crude 3-(1-(benzyloxyimino)ethyl)benzylisocyanate.

¹H-NMR(CDCl₃, TMS)

δ (ppm): 7.25–7.65 (9H, m), 5.23 (2H, s), 4.51 (2H, s), 2.27 (2H, s)

To a solution of 2.75 g of crude 3-(1-(benzyloxyimino) ethyl)benzylisocyanate in 13 ml of dry toluene was added dropwise a solution of 0.53 g (8.74 mmol) of N,N-dimethylhydrazine in 5 ml of dry toluene with ice-cooling. The mixture was removed from an ice bath and stirred for 1 hour. The reaction solution was concentrated, and the residue was subjected to silica gel column chromatography (eluted with n-hexane:ethyl acetate=1:1 and then 1:2) to obtain 0.55 g (1.62 mmol) of 1,1-dimethyl-4-{3-(1-(benzyloxyimino)ethyl)benzyl}-semicarbazide.

¹H-NMR(CDCl₃, TMS)

δ (ppm): 7.25–7.6 (9H, m), 6.4 (1H, br), 5.24 (2H, s), 5.05 (1H, br), 4.45 (2H, d), 2.49 (6H, s), 2.26 (3H, s)

PRODUCTION EXAMPLE 5

According to the same manner as described in Production Example 3, except that 5-chloro-2-methyl-4-{3-(1-(benzyloxyimino)ethyl)-6-methylbenzyl}-2,4-dihydro-3H-1,2,4-triazol-3-one (the compound 349 of the present invention, produced in the following Production Example 6) is used in place of 5-chloro-2-methyl-4-{3-(1-(benzyloxyimino)ethyl)benzyl}-2,4-dihydro-3H-1,2,4-triazol-3-one, 5-methoxy-2-methyl-4-{3-(1-(benzyloxyimino)ethyl)-6-methylbenzyl}-2,4-dihydro-3H-1,2,4-triazol-3-one (the compound 314 of the present invention) is obtained.

PRODUCTION EXAMPLE 6

According to the same manner as described in Production Example 4, except that 1,1-dimethyl-4-{3-(1-(benzyloxyimino)ethyl-6-methyl)benzyl}semicarbazide (produced in the following Reference Production Example 3) is used in place of 1,1-dimethyl-4-{3-(1-(benzyloxyimino)ethyl)benzyl}semicarbazide, 5-chloro-2-methyl-4-{3-(1-(benzyloxyimino)ethyl-6-methyl)benzyl}-2,4-dihydro-3H-1,2,4-triazol-3-one (the compound 349 of the present invention) is obtained.

Reference Production Example 3

(1) According to the same manner as described in Reference Production Example 2-(1), except that 3-acetyl-6-methylbenzonitrile is used in place of 3-acetylbenzonitrile, 3-(1(benzyloxyimino)ethyl)-6-methylbenzaldehyde is obtained through crude 3-(1-(benzyloxyimino)ethyl)-6-methylbenzonitrile.

(2) According to the same manner as described in Reference Production Example 2-(2), except that 3-(1-(benzyloxyimino)ethyl)-6-methylbenzaldehyde is used in place of 3-(1-(benzyloxyimino)ethyl)benzaldehyde, 3-(1-(benzyloxyimino)ethyl)-6-methylbenzylalcohol is obtained.

(3) According to the same manner as described in Reference Production Example 2-(3), except that 3-(1-(benzyloxyimino)ethyl)-6-methylbenzylalcohol is used in place of 3-(1-(benzyloxyimino)ethyl)benzylalcohol, 3-(1-(benzyloxyimino)ethyl)-6-methylbenzylbromide is obtained.

(4) According to the same manner as in Reference Production Example 2-(4), except that 3-(1-(benzyloxyimino)ethyl)-6-methylbenzylbromide is used in place of 3-(1-(benzyloxyimino)ethyl)benzylbromide, 1,1-dimethyl-4-{3-(1-(benzyloxyimino)ethyl)-6-methylbenzyl}-semicarbazide is obtained through crude 3-(1-(benzyloxyimino)ethyl)-6-methylbenzylisocyanate.

PRODUCTION EXAMPLE 7

A solution of 443 mg (1.5 mmol) of 5-methoxy-4-(2-methyl-5-phenylbenzyl)-2,4-dihydro-3H-1,2,4-triazol-3-one (produced in the following Reference Production Example 4) and 234 mg (1.65 mmol) of methyl iodide in 5 ml of dry N,N-dimethylformamide was added 66 mg (1.65 mmol) of sodium hydride (60% oil dispersion) with ice-cooling. After vigorous bubbling ceased, the mixture was removed from an ice bath and stirred at room temperature for 2 hours. Water was added to the reaction mixture and the resultant mixture was extracted with a mixed solvent of tert-butyl methyl ether and ethyl acetate. The organic layer was washed twice with water, dried and concentrated. To the residue were added acetonitrile and n-hexane and the mixture was separated. The acetonitrile layer was concentrated to obtain 0.45 g of 5-methoxy-2-methyl-4-(2-methyl-5-phenylbenzyl)-2,4-dihydro-3H-1,2,4-triazol-3-one (the compound 6 of the present invention) as viscous oil (crystallized upon standing at room temperature).

$^1$H-NMR(CDCl$_3$, TMS)

δ (ppm): 7.2–7.6 (8H, m), 4.78 (2H, s), 3.93 (3H, s), 3.39 (3H, s), 2.44 (3H, s)

Reference Production Example 4

(1) To 50 g of Na-X type zeolite dry powder (Zeolum type F-9; 100 meshes or finer, produced by Tosoh Corporation) was added dropwise 7.51 g (50.0 mmol) of methyl 2-methylbenzoate with stirring. Further, 3.9 ml (75 mmol) of bromine was added dropwise thereto at 45~50° C., and the mixture was stirred at 80° C. for 1 hour. To the reaction mixture was added a solution of potassium carbonate (5.5 g) in water (50 ml) and methanol (250 ml). The mixture was stirred at room temperature for 10 minutes and filtered. The residual zeolite powder was washed with warmed hydrous methanol (10%, 250 ml). The filtrate and the washing were combined and concentrated. The residue was diluted with ethyl acetate, washed twice with water, dried and concentrated. The residue (2.98 g) was subjected to silica gel column chromatography (eluted with n-hexane:toluene=10:1 and then 5:1 and then 3:1) to obtain 1.97 g (8.60 mmol) of methyl 5-bromo-2-methylbenzoate as crystals.

$^1$H-NMR(CDCl$_3$, TMS)

δ (ppm): 8.04 (1H, d), 7.52 (1H, dd), 7.12 (1H, d), 3.90 (3H, s), 2.54 (3H, s)

(2) A suspension of 1.19 g (9.46 mmol) of phenylboronic acid, 1.97 g (8.60 mmol) of methyl 5-bromo-2-methylbenzoate, 4 mg (0.017 mmol) of palladium (II) acetate, 2.97 g (21.5 mmol) of potassium carbonate, and 2.77 g (8.6 mmol) of tetrabutylammonium bromide in 20 ml of water was vigorously stirred under a stream of nitrogen, and stirred at 70° C. under an atmosphere of nitrogen for 1 hour. Water was added to the reaction mixture and it was extracted with tert-butyl methyl ether. The organic layer was dried and concentrated. The residue (1.9 g) was subjected to silica gel column chromatography (eluted with n-hexane:ethyl acetate=30:1) to obtain 1.65 g (7.29 mmol) of methyl 5-phenyl-2-methylbenzoate as an oil.

$^1$H-NMR(CDCl$_3$, TMS)

δ (ppm): 8.16 (1H, d), 7.3–7.7 (7H, m), 3.92 (3H, s), 2.64 (3H, s)

(3) To a suspension of 0.20 g (5.27 mmol) of lithium aluminum hydride in 50 ml of dry diethyl ether was added dropwise a solution of 1.65 g (7.29 mmol) of methyl 5-phenyl-2-methylbonzoate in 20 ml of dry diethyl ether under an atmosphere of nitrogen with ice-cooling. The mixture was warmed slowly to room temperature and stirred at room temperature for 1 hour. Then, 0.20 g (5.27 mmol) of lithium aluminum hydride was added thereto, and the mixture was stirred for 1 hour. Further, 0.20 g (5.27 mmol) of lithium aluminum hydride was added thereto, and the mixture was stirred for additional 1 hour. Hydrous sodium sulfate (prepared from 20 g of anhydrous sodium sulfate and 1.5 ml of water) was added thereto. The mixture was filtered, and the filtrate was concentrated. The residue (1.43 g) was subjected to silica gel column chromatography (eluted with n-hexane:ethyl acetate=10:1 and then 3:1) to obtain 1.33 g (6.71 mmol) of 5-phenyl-2-methylbenzylalcohol as an viscous oil.

$^1$H-NMR(CDCl$_3$, TMS)

δ (ppm): 7.25–7.65 (8H, m), 4.78 (2H, d), 2.40 (3H, s), 1.62 (1H, t)

(4) To a solution of 1.33 g (6.71 mmol) of 5-phenyl-2-methylbenzylalcohol in 30 ml of dry diethyl ether was added dropwise 0.91 g (3.02 mmol) of phosphorous tribromide with ice-cooling. After the mixture was stirred for 3 hours with ice-cooling, to the reaction solution were added ice water and tert-butyl methyl ether with ice-cooling. The mixture was stirred for 30 minutes and separated. The organic layer was washed successively with an about 5% aqueous solution of sodium hydrogencarbonate and water, then dried and concentrated to obtain 1.42 g (5.44 mmol) of 5-phenyl-2-methylbenzylbromide as an oil.

$^1$H-NMR(CDCl$_3$, TMS)

δ (ppm): 7.25–7.65 (8H, m), 4.58 (2H, s), 2.46 (2H, s)

(5) To a solution of 626 mg (5.44 mmol) of 5-methoxy-2,4-dihydro-3H-1,2,4-triazol-3-one (said compound is a known compound described in J. Chem. Soc. Perkin I, 2645 (1973) and this was produced according to the method described in this literature. In this literature, said compound is named as 3-methoxy-1,2,4-triazol-5(4H)-one) in 7 ml of dry acetonitrile was added 0.79 g (5.71 mmol) of potassium carbonate. To the mixture was added dropwise a solution of 1.42 g (5.44 mmol) of 5-phenyl-2-methylbenzylbromide in 20 ml of dry acetonitrile at 55° C. After the mixture was stirred at the same temperature for additional 5 hours, water was added to the reaction mixture and it was extracted with ethyl acetate. The organic layer was washed with water, dried, and concentrated. To the resultant solid residue (1.51 g) was added tert-butyl methyl ether and the solid was washed and ice-cooled. The solid was collected by filtration and dried to obtain 0.72 g (2.44 mmol) of 5-methoxy-4-(2-methyl-5-phenylbenzyl)-2,4-dihydro-3H-1,2,4-triazol-3-one as white powder.

$^1$H-NMR(CDCl$_3$, TMS)

δ (ppm): 8.22 (1H, br s), 7.2–7.6 (8H, m), 4.80 (2H, s), 3.94 (3H, s), 2.44 (3H, s)

PRODUCTION EXAMPLE 8

A suspension of 0.19 g (1.18 mmol) of 4-chlorophenylboronic acid, 0.32 g (1.07 mmol) of 4-(3-bromobenzyl)-5-methoxy-2-methyl-2,4-dihydro-3H-1,2,4-triazol-3-one (the compound 296 of the present invention, produced in the following Production Example 9), 1 mg (0.004 mmol) of palladium (II) acetate, 0.37 g (2.68 mmol) of potassium carbonate and 0.34 g (1.07 mmol) of tetrabutylammonium bromide in 2 ml of water was vigorously stirred under a stream of nitrogen, and stirred at 75° C. under an atmosphere of nitrogen for 1 hour. Water was added to the reaction mixture and the mixture was extracted with ethyl acetate. The organic layer was dried and concentrated. The residue (0.39 g) was subjected to silica gel thin layer chromatography (developed with toluene: ethyl acetate=1:1) to obtain 0.32 g of 4-{3-(4-chlorophenyl)benzyl}-5-methoxy-2-methyl-2,4-dihyro-3H-1,2,4-triazol-3-one (the compound 21 of the present invention) as a viscous oil.

$^1$H-NMR(CDCl$_3$, TMS)

δ (ppm): 7.3–7.6 (7H, m), 4.76 (2H, s), 3.95 (3H, s), 3.37 (3H, s)

PRODUCTION EXAMPLE 9

A solution of 1.70 g (5.98 mmol) of 4-(3-bromobenzyl)-5-methoxy-2,4-dihydro-3H-1,2,4-triazol-3-one (produced in the following Reference Production Example 5) and 1.02 g (7.18 mmol) of methyl iodide in 20 ml of dry N,N-dimethylformamide was added 287 mg (7.18 mmol) of sodium hydride (60% oil dispersion) with ice-cooling. After vigorous bubbling ceased, the mixture was removed from an ice bath and stirred at room temperature for 3 hours. Water was added to the reaction solution and the mixture was extracted with a mixed solvent of tert-butyl methyl ether and ethyl acetate. The organic layer was washed twice with water, dried and concentrated. To the residue were added acetonitrile and n-hexane. The mixture was separated and the acetonitrile layer was concentrated to obtain 1.64 g (5.50 mmol) of 4-(3-bromobenzyl)-5-methoxy-2-methyl-2,4-dihydro-3H-1,2,4-triazol-3-one (the compound 296 of the present invention) as a viscous oil.

$^1$H-NMR(CDCl$_3$, TMS)

δ (ppm): 7.15–7.5 (4H, m), 4.66 (2H, s), 3.95 (3H, s), 3.38 (3H, s)

Reference Production Example 5

To a solution of 2.30 g (20 mmol) of 5-methoxy-2,4-dihydro-3H-1,2,4-triazol-3-one in 20 ml acetonitrile was added 2.90 g (21 mmol) of potassium carbonate. A solution of 5.00 g (20 mmol) of 3-bromobenzylbromide in 20 ml of dry acetonitrile was added dropwise thereto at 55° C. After the mixture was stirred at the same temperature for additional 6 hours, water was added to the reaction mixture and the mixture was extracted with ethyl acetate. The organic layer was washed with water, dried and concentrated. To the resultant solid residue (5.2 g) was added a mixture of equal amounts of tert-butyl methyl ether and n-hexane and the solid was washed, ice-cooled, collected by filtration and concentrated. Further, to the resultant solid residue was added tert-butyl methyl ether and the solid was washed, cooled, collected by filtration and dried to obtain 1.70 g (5.98 mmol) of 4-(3-bromobenzyl)-5-methoxy-2,4-dihydro-3H-1,2,4-triazol-3-one as white powder.

$^1$H-NMR(CDCl$_3$, TMS)

δ (ppm): 8.52 (1H, br s), 7.15–7.5 (4H, m), 4.67 (2H, s), 3.96 (3H, s)

PRODUCTION EXAMPLE 10

To a solution of 0.27 g (0.91 mmol) of 5-methoxy-4-(3-phenoxybenzyl)-2,4-dihydro-3H-1,2,4-triazol-3-one (produced in the following Reference Production Example 6) and 0.15 g (1.09 mmol) of methyl iodide in 3 ml of dry N,N-dimethylformamide was added 44 mg (1.09 mmol) of sodium hydride (60% oil dispersion) was added with ice-cooling. After vigorous bubbling ceased, the mixture was removed from an ice bath and stirred at room temperature for 7 hours. Water was added to the reaction solution and the mixture was extracted with ethyl acetate. The organic layer was washed twice with water, dried and concentrated. To the residue were added acetonitrile and n-hexane and the mixture was separated. The acetonitrile layer was concentrated to obtain 0.26 g of 5-methoxy-2-methyl-4-(3-phenoxybenzyl)-2,4-dihydro-3H-1,2,4-triazol-3-one (the compound 176 of the present invention) as a viscous oil.

$^1$H-NMR(CDCl$_3$TMS)

δ (ppm): 6.85–7.4 (9H, m), 4.67 (2H, s), 3.91 (3H, s), 3.37 (3H, s)

Reference Production Example 6

To a solution of 575 mg (5 mmol) of 5-methoxy-2,4-dihydro-3H-1,2,4-triazol-3-one in 7 ml of dry acetonitrile was added 726 mg (5.25 mmol) of potassium carbonate was added. A solution of 1.32 g (5 mmol) of 3-phenoxybenzylbromide in 9 ml of dry acetonitrile was added dropwise thereto at 55° C. After the mixture was stirred at the same temperature for additional 5.5 hours, water was added to the reaction mixture and the mixture was extracted with ethyl acetate. The organic layer was washed with water, dried and concentrated. To the resultant solid residue (1.36 g) was added a mixture of equal amounts of tert-butyl methyl ether and n-hexane. The mixture was cooled and the deposited solid was washed, ice-cooled, collected by filtration, and dried to obtain a residue. The residue was recrystallized from tert-butyl methyl ether to obtain 0.27 g of 5-methoxy-4-(3-phenoxybenzyl)-2,4-dihydro-3H-1,2,4-triazol-3-one as white powder.

$^1$H-NMR(CDCl$_3$, TMS)

δ (ppm): 8.25 (1H, br s), 6.9–7.4 (9H, m), 4.68 (2H, s), 3.93 (3H, s)

PRODUCTION EXAMPLE 11

A solution of 314 mg (1.0 mmol) of 5-chloro-2-methyl-4-{1-(3-phenylphenyl)ethyl}-2,4-dihydro-3H-1,2,4-triazol-3-one (the compound 12 of the present invention, produced in the following Reference Production Example 12) was added 0.85 g (4.4 mmol) of sodium methoxide (28% methanol solution) and the mixture was heated under reflux for 4 hours. Further, 0.85 g (4.4 mmol) of sodium methoxide (28% methanol solution) was added thereto, and the mixture was heated under reflux for 5.5 hours. After allowing to cool to room temperature, water was added to the reaction mixture was added and the mixture was extracted with tert-butyl methyl ether. The organic layer was washed with water, dried and concentrated. The residue (0.25 g) was subjected to silica gel preparative thin layer chromatography (developed with n-hexane:ethyl acetate=1:1) to obtain 0.21 g of 5-methoxy-2-methyl-4-{1-(3-phenylphenyl)ethyl}-2,4-dihydro-3H-1,2,4-triazol-3-one (the compound 11 of the present invention) as a viscous oil.

$^1$H-NMR(CDCl$_3$, TMS)

δ (ppm): 7.3–7.65 (9H, m), 5.38 (1H, q), 3.90 (3H, s), 3.35 (3H, s), 1.86 (3H, d)

PRODUCTION EXAMPLE 12

To a solution of 4.33 g (14.6 mmol) of triphosgene in 15 ml of methylene chloride was added dropwise a solution of 2.07 g (7.30 mmol) of 1,1-dimethyl-4-{1-(3-phenylphenyl) ethyl}semicarbazide (produced in the following Reference Production Example 7) in 20 ml of methylene chloride with ice-cooling. The mixture was removed from an ice bath, warmed to room temperature and heated under reflux for 4 hours. After allowing to cool to room temperature, the reaction mixture was poured into 150 ml of an about 5% aqueous solution of sodium bicarbonate, and the mixture was stirred for 1 hour. The organic layer was washed with water, dried and concentrated. The residue (1.93 g) was subjected to silica gel column chromatography (eluted with n-hexane:ethyl acetate=10:1 and then 5:1 and then 3:1) to obtain 418 mg (1.33 mmol) of 5-chloro-2-methyl-4-{1-(3-phenylphenyl)ethyl}-2,4-dihydro-3H-1,2,4-triazol-3-one (the compound 12 of the present invention) as an oil.

$^1$H-NMR(CDCl$_3$, TMS)

δ (ppm): 7.3–7.65 (9H, m), 5.52 (1H, q), 3.44 (3H, s), 1.97 (3H, d)

Reference Production Example 7

(1) A suspension of 6.71 g (55 mmol) of phenylboronic acid, 9.95 g (50 mmol) of 3-bromoacetophenone, 30 mg (0.13 mmol) of palladium acetate, 17.28 g (125 mmol) of potassium carbonate and 16.12 g (50 mmol) of tetrabutylammonium bromide in 55 ml of water was vigorously stirred under a stream of nitrogen and then stirred at 70° C. under an atmosphere of nitrogen for 75 minutes. Water was added to the reaction mixture and the mixture was extracted with tert-butyl methyl ether. Then, the organic layer was dried and concentrated. The residue (10.23 g) was subjected to silica gel column chromatography (eluted with n-hexane:ethyl acetate=7:1) to obtain 9.82 g of 3-acetylbiphenyl as oil.

$^1$H-NMR(CDCl$_3$, TMS)

δ (ppm): 8.20 (1H, t), 7.95 (1H, dt), 7.81 (1H, dt), 7.3–7.65 (6H, m), 2.66 (3H, s)

(2) To a solution of 9.82 g (50 mmol) of 3-acetylbiphenyl in 80 ml of dry methanol and 80 ml of dry tetrahydrofuran was added 3.36 g (80 mmol) of sodium borohydride portionwise with ice-cooling, and the mixture was stirred for 1 hour. To the reaction solution was added 600 ml of an about 5% aqueous solution of ammonium chloride and the mixture was extracted with tert-butyl methyl ether. The organic layer was dried and concentrated to obtain 9.86 g (49.7 mmol) of 3-(1-hydroxyethyl)biphenyl as an oil.

$^1$H-NMR(CDCl$_3$, TMS)

δ (ppm): 7.3–7.65 (9H, m), 4.98 (1H, q), 1.85 (1H, br), 1.55 (3H, d)

(3) To a solution of 3.97 g (20 mmol) of 3-(1-hydroxyethyl)biphenyl in 60 ml of dry diethyl ether was added dropwise 2.70 g (9.0 mmol) of phosphorous tribromide with ice-cooling, and the mixture was further stirred with ice-cooling for 3 hours. To the reaction solution were added ice water and tert-butyl methyl ether. The mixture was stirred for 30 minutes and separated. The organic layer was washed successively with an about 5% aqueous solution of sodium bicarbonate and water, dried and concentrated to obtain 3.73 g (14.28 nmol) of 3-(1-bromoethyl)biphenyl as an oil.

$^1$H-NMR(CDCl$_3$, TMS)

δ (ppm): 7.3–7.7 (9H, m), 5.28 (1H, q), 2.10 (3H, d)

(4) To a solution of 2.61 g (10 mmol) of 3-(1-bromoethyl) biphenyl in 30 ml of dry tetrahydrofuran was added 1.99 g (13 mmol) of silver cyanate and the mixture was heated under reflux for 2 hours. The reaction solution was filtered, and the filtrate was concentrated to obtain 2.29 g of 1-(3-phenylphenyl)ethylisocyanate.

$^1$H-NMR(CDCl$_3$, TMS)

δ (ppm): 7.25–7.65 (9H, m), 4.85 (1H, q), 1.65 (3H, d)

(5) To a solution of 2.29 g of 1-(3-phenylphenyl)ethylisocyanate in 8 ml of toluene was added dropwise 0.78 g (13 mmol) of N,N-dimethylhydrazine with ice-cooling. The mixture was removed from an ice bath and stirred for 1.5 hours. The reaction solution was concentrated, and the residue (2.89 g) was subjected to silica gel column chromatography (eluted with n-hexane:ethyl acetate=2:1and then 1:1 and then 1:2) to obtain 2.29 g (8.08 mmol) of 1,1-dimethyl-4-{1-(3-phenylphenyl)ethyl}semicarbazide as a viscous oil.

$^1$H-NMR(CDCl$_3$, TMS)

δ (ppm): 7.3–7.65 (9H, m), 6.38 (1H, br d), 5.10 (1H, m), 4.98 (1H, br s), 2.51 (6H, s), 1.55 (3H, d)

PRODUCTION EXAMPLE 13

To a solution of 5 mg of crude 4-{3-(bromomethyl) benzyl}-5-methoxy-2-methyl-2,4-dihydro-3H-1,2,4-triazol-3-one (the compound 62 of the present invention, produced in the following Production Example 14) and 3 mg (0.016 mmol) of 3-(trifluoromethyl)acetophenoneoxime was added a solution of 1 mg (0.025 mmol) of sodium hydride (60% oil dispersion) with ice-cooling. A reaction vessel was removed from an ice bath, and the mixture was stirred at room temperature for 2 hours. To the reaction mixture was added ice water and the mixture was extracted with tert-butyl methyl ether. The organic layer was washed twice with water, dried and concentrated. The residue was subjected to silica gel thin layer chromatography (developed with n-hexane:ethyl acetate=1:1), which afforded 2 mg of 5-methoxy-2-methyl-4-{3-[[α-methyl-(3-trifluoromethyl) benzylidene]-aminoxymethyl]benzyl}-2,4-dihydro-3H-1,2, 4-triazol-3-one (the compound 477 of the present invention).

$^1$H-NMR(CDCl$_3$, TMS)

δ (ppm): 7.89 (1H, s), 7.84 (1H, d), 7.61 (1H, d), 7.48 (1H, t), 7.25–7.4 (4H, m), 5.24 (2H, s), 4.71 (2H, s), 3.91 (3H, s), 3.36 (3H, s), 2.29 (3H, s)

PRODUCTION EXAMPLE 14

To a solution of 50 mg (0.20 mmol) of 4-{3-(hydroxymethyl)benzyl}-5-methoxy-2-methyl-2,4-dihydro-3H-1,2,4-triazol-3-one (the compound 476 of the present invention, produced in the following Production Example 15) in 5 ml of dry diethyl ether was added dropwise a solution of 30 mg (0.1 mmol) of phosphorous tribromide in 5 ml of dry diethyl ether with ice-cooling, and the mixture was stirred for 2.5 hours with ice-cooling. To the reaction solution were added ice water and tert-butyl methyl ether and the mixture was stirred for 30 minutes and separated. The organic layer was washed successively with an about 5% aqueous solution of sodium bicarbonate and with water twice, then dried and concentrated to obtain 5 mg of crude 4-{3-(bromomethyl)benzyl}-5-methoxy-2-methyl-2,4-dihydro-3H-1,2,4-triazol-3-one (the compound 62 of the present invention). $^1$H-NMR(CDCl$_3$, TMS)

δ (ppm): 7.2–7.4 (4H, m), 4.69 (2H, s), 4.47 (2H, s), 3.95 (3H, s), 3.37 (3H, s)

PRODUCTION EXAMPLE 15

To a solution of 0.16 g of crude 4-(3-formylbenzyl)-5-methoxy-2-methyl-2,4-dihydro-3H,1,2,4-triazol-3-one (the compound 55 of the present invention, produced in the following Production Example 16) in 3 ml of dry methanol and 3 ml of dry tetrahydrofuran was added 32 mg (0.75 mmol) of sodium borohydride portionwise with ice-cooling and the mixture was stirred for additional 1 hour with ice-cooling. The reaction mixture was added to 15 ml of an about 5% aqueous solution of ammonium chloride, and the mixture was extracted with tert-butyl methyl ether. The organic layer was dried. The residue (0.10 g) was subjected to silica gel thin layer chromatography (developed with ethyl acetate) to obtain 50 mg (0.20 mmol) of 4-{3-(hydroxymethyl)benzyl}-5-methoxy-2-methyl-2,4-dihydro-3H-1,2,4-triazol-3-one (the compound 476 of the present invention).

$^1$H-NMR(CDCl$_3$, TMS)

δ (ppm): 7.2–7.4 (4H, m), 4.67 (2H, s), 4.65 (2H, s), 3.93 (3H, s), 3.34 (3H, s), 2.70 (1H,br s)

PRODUCTION EXAMPLE 16

A solution of 0.35 g (1.50 mmol) of 4-(3-formylbenzyl)-5-methoxy-2,4-dihydro-3H-1,2,4-triazol-3-one (produced in the following Reference Production Example 8) and 0.23 g (1.65 mmol) of methyl iodide in 5 ml of dry N,N-dimethylformamide was added 66 mg (1.65 mmol) of sodium hydride (60% oil dispersion) with ice-cooling. After vigorous bubbling ceased, a reaction vessel was removed from an ice bath, and the mixture was stirred for 3 hours. Water was added to the reaction solution and the mixture was extracted with a mixed solvent of tert-butyl methyl ether and ethyl acetate. The organic layer was washed twice with water, dried and concentrated. Then, to the residue were added actetonitrile and n-hexane and the mixture was separated. The acetonitrile layer was concentrated. The residue (0.25 g) was subjected to silica gel thin layer chromatography (developed with ethyl acetate:toluene=2:1) to obtain 0.16 g of crude 4-(3-formylbenzyl)-5-methoxy-2-methyl-2,4-dihydro-3H-1,2,4-triazol-3-one (the compound 55 of the present invention).

$^1$H-NMR(CDCl$_3$, TMS)

δ (ppm): 10.01 (1H, s), 7.83 (1H, s), 7.83 (1H, d), 7.63 (1H, d), 7.51 (1H, t), 4.78 (2H, s), 3.95 (3H, s), 3.39 (3H, s)

Reference Production Example 8

To a solution of 5.00 g (25.5 mmol) of 3-(bromomethyl)benzonitrile in 50 ml of dry toluene was added dropwise 37.9 ml (36 mmol) of diisobutylaluminumhydride (0.95 mol/liter of n-hexane solution) with ice-cooling under an atmosphere of nitrogen and the mixture was stirred with ice-cooling for additional 1 hour. To the reaction solution was added 80 ml of chloroform with ice-cooling and further was added 200 ml of about 10% aqueous hydrochloric acid with ice-cooling, The mixture was stirred at room temperature for 1 hour. The organic layer was separated, washed with water, dried and concentrated. The solid residue (4.90 g) was washed with n-hexane, cooled, collected by filtration, and dried to obtain 4.27 g of crude 3-(bromomethyl) benzaldehyde as crystals.

$^1$H-NMR(CDCl$_3$, TMS)

δ (ppm): 10.02 (1H, s), 7.91 (1H, s), 7.83 (1H, d), 7.66 (1H, d), 7.53 (1H, t), 4.54 (2H, s)

To a solution of 0.92 g (8.0 mmol) of 5-methoxy-2,4-dihydro-3H-1,2,4-triazol-3-one in 15 ml of dry acetonitrile was added 1.16 g (8.4 mmol) of potassium carbonate. To the mixture was added dropwise a solution of 1.59 g of crude 3-(bromomethyl)benzaldehyde in 30 ml of dry acetonitrile at 55° C. under an atmosphere of nitrogen. After the mixture was stirred at the same temperature for additional 6 hours, water was added to the reaction mixture, and the mixture was extracted with ethyl acetate. The organic layer was washed with water, dried and concentrated. The residue (1.31 g) was subjected to silica gel column chromatography (eluted with n-hexane:ethyl acetate=1:1 and then 1:2) to obtain 0.35 g (1.50 mmol) of 4-(3-formylbenzyl)-5-methoxy-2,4-dihydro-3H-1,2,4-triazol-3-one as white powder.

$^1$H-NMR(CDCl$_3$, TMS)

δ (ppm): 10.01 (1H, s), 8.63 (1H, br s), 7.83 (1H, s), 7.83 (1H, d), 7.63 (1H, d), 7.52 (1H, t), 4.79 (2H, s), 3.97 (3H, s)

PRODUCTION EXAMPLE 17

According to the same manner as described in Production Example 7, except that 4-{5-(4-chlorophenyl)-2-methylbenzyl}-5-methoxy-2,4-dihydro-3H-1,2,4-triazol-3-one (produced in the following Reference Production Example 9) is used in place of 5-methoxy-4-(2-methyl-5-phenylbenzyl)-2,4-dihydro-3H-1,2,4-triazol-3-one, 4-{5-(4-chloro)-2-methylbenzyl}-5-methoxy-2-methyl-2,4-dihydro-3H-1,2,4-triazol-3-one (the compound 46 of the present invention) is obtained.

Reference Production Example 9

According to the same manner as described in Reference Production Example 4-(2), except that 4-chlorophenylboronic acid is used in place of phenylboronic acid, methyl 5-(4-chlorophenyl)-2-methylbenzoate is obtained. Then, according to the same manner as described in Reference Production Example 4-(3), except that methyl 5-(4-chlorophenyl)-2-methylbenzoate is used in place of methyl 5-phenyl-2-methylbenzoate, 5-(4-chlorophenyl)-2-methylbenzylalcohol is obtained. Then, according to the same manner as described in Reference Production Example 4-(4), except that 5-(4-chlorophenyl)-2-methybenzylalcohol is used in place of 5-phenyl-2-methylbenzylalcohol, 5-(4-chlorophenyl)-2-methylbenzylbromide is obtained. Then, according to the same manner as described in Reference Production Example 4-(5), except that 5-(4-chlorophenyl)-2-methylbenzylbromide is used in place of 5-phenyl-2-methylbenzylbromide, 4-{5-(4-chlorophenyl)-2-methylbenzyl}-5-methoxy-2,4-dihydro-3H-1,2,4-triazol-3-one is obtained.

PRODUCTION EXAMPLE 18

According to the same manner as described in Production Example 7, except that 5-methoxy-4-{2-methyl-5-(4-methylphenyl)benzyl}-2,4-dihydro-3H-1,2,4-triazol-3-one (produced in the following Reference Production Example 10) is used in place of 5-methoxy-4-(2-methyl-5-phenylbenzyl)-2,4-dihydro-3H-1,2,4-triazol-3-one, 5-methoxy-2-methyl-4-{2-methyl-5-(4-methylphenyl)benzyl}-2,4-dihydro-3H-1,2,4-triazol-3-one (the compound 49 of the present invention) is obtained.

Reference Production Example 10

According to the same manner as described in Reference Production Example 4-(2), except that 4-methylphenylboronic acid is used in place of phenylboronic acid, methyl 2-methyl-5-(4-methylphenyl)benzoate is obtained. Then, according to the same manner as described in Reference Production Example 4-(3), except that methyl 2-methyl-5-(4-methylphenyl)benzoate is used in place of methyl 5-phenyl-2-methylbenzoate, 2-methyl-5-(4-methylphenyl)benzylalcohol is obtained. Then, according to the same manner as described in Reference Production Example 4-(4), except that 2-methyl-5-(4-methylphenyl)benzylalcohol is used in place of 5-phenyl-2-methylbenzylalcohol, 2-methyl-5-(4-methylphenyl)benzylbromide is obtained. Then, according to the same manner as described in Reference Production Example 4-(5), except that 2-methyl-5-(4-methylphenyl)

benzylbromide is used in place of 5-phenyl-2-methylbenzylbromide, 5-methoxy-4-{2-methyl-5-(4-methylphenyl)benzyl}-2,4-dihydro-3H-1,2,4-triazol-3-one is obtained.

PRODUCTION EXAMPLE 19

A suspension of 1.19 g (9.46 mmol) of phenylboronic acid, 2.68 g (8.6 mmol) of 4-(5-bromo-2-methylbenzyl)-5-methoxy-2-methyl-2,4-dihydro-3H,1–2,4-triazol-3-one (the compound 299 of the present invention, produced in the following Production Example 20), 4 mg (0.017 mmol) of palladium (II) acetate, 2.97 g (21.5 mmol) of potassium carbonate and 2.77 g (8.6 mmol) of tetrabutylammonium bromide in 20 ml of water was vigorously stirred under a stream of nitrogen and then stirred at 70° C. under an atmosphere of nitrogen for 1 hour. Water was added to the reaction mixture and the mixture was extracted with ethyl acetate. The organic layer was washed with water, dried and concentrated. The residue (2.84 g) was subjected to silica gel column chromatography (eluted with n-hexane:ethyl acetate=2:1and then 1:1 and then 1:2) to obtain 2.47 g of 5-methoxy-2-methyl-4-(2-methyl-5-phenylbenzyl)-2,4-dihydro-3H-1,2,4-triazol-3-one (the compound 6 of the present invention) as a viscous oil (this was crystallized by addition of n-hexane and trituration).

The
$^1$H-NMR(CDCl$_3$TMS) spectrum date agreed with those described in Production Example 7.

PRODUCTION EXAMPLE 20

To a solution of 11.96 g (40.12 mmol) of 4-(5-bromo-2-methylbenzyl)-5-methoxy-2,4-dihydro-3H-1,2,4-triazol-3-one (produced in the following Reference Production Example 11) and 6.83 g (48.14 mmol) of methyl iodide in 100 ml of dry N,N-dimethylformamide was added 1.93 g (48.14 mmol) of sodium hydride (60% oil dispersion) with ice-cooling. After vigorous bubbling ceased, the mixture was removed from an ice bath and stirred at room temperature for 3 hours. The reaction solution was added to ice water (500 ml), and the mixture was extracted with ethyl acetate (300 ml). The organic layer was washed successively with water and saturated brine, then dried and concentrated. Cold n-hexane was added to the solid residue to wash it thoroughly. The solid was collected by filtration and dried to obtain 11.6 g of 4-(5-bromo-2-methylbenzyl)-5-methoxy-2-methyl-2,4-dihydro-3H-1,2,4-triazol-3-one (the compound 299 of the present invention) as crystals.

$^1$H-NMR(CDCl$_3$, TMS)

δ (ppm): 7.32 (1H, dd), 7.27 (1H, d), 7.03 (1H, d), 4.67 (2H, s), 3.94 (3H, s), 3.40 (3H, s), 2.34 (3H, s)

Reference Production Example 11

(1) To 250 g of stirred Na-X type zeolite dry powder (Zeolum typeF-9, produced by Tosoh Corporation; not greater than 100 meshes) was added dropwise 37.5 g (0.25 mol) of methyl 2-methylbenzoate. To the mixture was added dropwise 60.0 g (0.3754 mol) of bromine and the mixture was stirred at 80 to 85° C. for 1 hour. The reaction mixture was cooled, followed by addition of a solution of potassium carbonate (20 g) in water (250 ml), and further addition of 1 liter of methanol thereto. The mixture was stirred at room temperature and filtred. The filtrate was concentrated to about 100 ml and water and ethyl acetate were added and the mixture was separated. Then, the organic layer was washed with water and concentrated to obtain 20 g of a residue. On the other hand, the residual zeolite powder was washed twice with 1.1 liter of an 90% aqueous solution of methanol, and the washing was concentrated to about 100 ml. Water and ethyl acetate were added thereto and the mixture was separated. The organic layer was washed with water and concentrated to obtain 17 g of a residue. These residues were combined and distilled (an about 60 mm Vigoureux rectification tower was used; bp 80~95° C./0.6 mmHg) to obtain 17.0 g of methyl 5-bromo-2-methylbenzoate as crystals.

The $^1$H-NMR(CDCl$_3$, TMS) spectrum date agreed with those described in Reference Production Example 4-(1).

(2) To a suspension of 4.2 g (0.1094 mol) of lithium aluminum hydride in 250 ml of dry diethyl ether was added dropwise a solution of 33.4 g (0.1458 mol) of methyl 5-bromo-2-methylbenzoate in 50 ml of dry diethyl ether at room temperature over 30 minutes with ice-cooling under an atmosphere of nitrogen. The mixture was stirred at room temperature for 2 hours. About 10 ml of ethyl acetate was added dropwise thereto and further about 50 ml of tetrahydrofuran was added thereto. The mixture was added to 200 ml of a 10% aqueous solution of sulfuric acid and ice, and the mixture was separated. The organic layer was washed successively with water, a saturated aqueous solution of sodium bicarbonate and saturated brine, then dried and concentrated. The residue (28.7 g) was subjected to silica gel column chromatography (eluted with n-hexane:ethyl acetate=10:1 and then 5:1) to obtain 24.36 g of 5-bromo-2-methylbenzylalcohol as crystals.

$^1$H-NMR(CDCl$_3$, TMS)

δ (ppm): 7.51 (1H, d), 7.30 (1H, dd), 7.02 (1H, d), 4.63 (2H, d), 2.22 (3H, s), 2.07 (1H, t)

(3) To a solution of 24.4 g (0.1214 mol) of 5-bromo-2-methylbenzylalcohol in 200 ml of dry diethyl ether was added dropwise 16.4 g (0.06067 mol) of phosphorous tribromide over 30 minutes with ice-cooling. After the mixture was stirred for 3 hours with ice-cooling, the reaction mixture was added to ice water (500 ml), and the mixture was separated. The organic layer was washed successively with water, a saturated aqueous solution of sodium bicarbonate and saturated brine, then dried and concentrated to obtain 29.07 g of 5-bromo-2-methylbenzylbromide as crystals.

$^1$H-NMR(CDCl$_3$, TMS)

δ (ppm): 7.44 (1H, d), 7.33 (1H, dd), 7.05 (1H, d), 4.43 (2H, s), 2.35 (3H, s)

(4) To a solution of 12.7 g (0.112 mol) of 5methoxy-2,4-dihydro-3H-1,2,4-triazol-3-one in 150 ml of dry acetonitrile was added 16.0 g (0.1158 mol) of potassium carbonate with ice-cooling. To the mixture was added dropwise a solution of 29.1 g (0.1102 mol) of 5-bromo-2-methylbenzylbromide in 200 ml of dry acetonitrile. After the mixture was stirred at 55 to 60° C. for 5 hour, the reaction solution was added to ice water (about 1 liter), and the mixture was extracted with ethyl acetate (500 ml). The organic layer was washed with water, dried and concentrated. To the resultant semisolid residue, was added cold tert-butyl methyl ether and the solid was washed, collected by filtration and dried to obtain a solid residue (15.9 g). The residue was recrystallized from a mixed solvent of toluene and ethyl acetate to obtain 11.96 g of 4-(5-bromo-2-methylbenzyl)-5-methoxy-2,4-dihyro-3H-1,2,4-triazol-3-one as crystals.

$^1$H-NMR(CDCl$_3$, TMS)

δ (ppm): 8.80 (1H, br s), 7.31 (1H, dd), 7.27 (1H, d), 7.06 (1H, d), 4.70 (2H, s), 3.96 (3H, s), 2.35 (3H, s)

PRODUCTION EXAMPLE 21

A suspension of 0.19 g (1.18 mmol) of 4-chlorophenylboronic acid, 0.34 g (1.07 mmol) of 4-(5- bromo-2-methylbenzyl)-5-methoxy-2-methyl-2,4-dihydro-3H-1,2,4-triazol-3-one (the compound 299 of the present invention, produced in Production Example 20), 1 mg (0.004 mmol) of palladium (II) acetate, 0.37 g (2.68 mmol) of potassium carbonate and 0.34 g (1.07 mmol) of tetrabutylammonium bromide in 5 ml of water was vigorously stirred under a stream of nitrogen and stirred at 75° C. (bath temperature) under an atmosphere of nitrogen for 1 hour. Water was added to the reaction mixture and the mixture was extracted with ethyl acetate. The organic layer was dried and concentrated. The residue (0.41 g) was subjected to silica gel thin layer chromatography (developed with n-hexane:ethyl acetate=1:2) to obtain 0.37 g of 4-{5-(4-chlorophenyl)-2-methylbenzyl}-5-methoxy-2-methyl-2,4-dihydro-3H-1,2,4-trizol-3-one (the compound 46 of the present invention) as a viscous oil.

$^1$H-NMR(CDCl$_3$, TMS)

δ (ppm): 7.2–7.65 (7H, m), 4.77 (2H, s), 3.93 (3H, s), 3.39 (3H, s), 2.44 (3H, s)

PRODUCTION EXAMPLE 22

According to the same manner as described in Production Example 21, except that 0.16 g of 4-methylphenylboronic acid was used in place of 0.19 g of 4-chlorophenylboronic acid, 0.36 g of 5-methoxy-2-methyl-4-{5-(4-methylphenyl)-2-methylbenzyl}-2,4-dihydro-3H-1,2,4-triazol-3-one (the compound 49 of the present invention) was obtained as crystals.

$^1$H-NMR(CDCl$_3$, TMS)

δ (ppm): 7.15–7.45 (7H, m), 4.77 (2H, s), 3.92 (3H, s), 3.39 (3H, s), 2.43 (3H, s), 2.38 (3H, s)

PRODUCTION EXAMPLE 23

According to the same manner as described in Production Example 21, except that 0.18 g of 4-methoxyphenylboronic acid was used in place of 0.19 g of 4-chlorophenylboronic acid, 0.32 g of 5-methoxy-4-{5-(4-methoxyphenyl)-2-methylbenzyl}-2-methyl-2,4-dihydro-3H-1,2,4-triazol-3-one (the compound 47 of the present invention) was obtained as crystals.

$^1$H-NMR(CDCl$_3$, TMS)

δ (ppm): 6.85–7.5 (7H, m), 4.76 (2H, s), 3.92 (3H, s), 3.84 (3H, s), 3.39 (3H, s), 2.42 (3H, s)

PRODUCTION EXAMPLE 24

According to the same manner as described in Production Example 21, except that 0.17 g of 4-fluorophenylboronic acid was used in place of 0.19 g of 4-chlorophenylboronic acid, 0.32 g of 4-{5-(4-fluorophenyl)-2-methylbenzyl}-5-methoxy-2-methyl-2,4-dihydro-3H-1,2,4-triazol-3-one (the compound 480 of the present invention) was obtained as a viscous oil.

$^1$H-NMR(CDCl$_3$, TMS)

δ (ppm): 7.0–7.55 (7H, m), 4.77 (2H, s), 3.93 (3H, s), 3.39 (3H, s), 2.43 (3H, s)

PRODUCTION EXAMPLE 25

According to the same manner as described in Production Example 21, except that 0.19 g of 3-chlorophenylboronic acid was used in place of 0.19 g of 4-chlorophenylboronic acid, 0.32 g of 4-{5-(3-chlorophenyl)-2-methylbenzyl}-5-methoxy-2-methyl-2,4-dihydro-3H-1,2,4-triazol-3-one (the compound 47 of the present invention) was obtained as a viscous oil.

$^1$H-NMR(CDCl$_3$, TMS)

δ (ppm): 7.15–7.55 (7H, m), 4.77 (2H, s), 3.94 (3H, s), 3.39 (3H, s), 2.44 (3H, s)

PRODUCTION EXAMPLE 26

According to the same manner as described in Production Example 21, except that 0.19 g of 2-chlorophenylboronic acid was used in place of 0.19 g of 4-chlorophenylboronic acid, 0.29 g of 4-{5-(2-chlorophenyl)-2-methylbenzyl}-5-methoxy-2-methyl-2,4-dihydro-3H-1,2,4-triazol-3-one (the compound 48 of the present invention) was obtained as a viscous oil.

$^1$H-NMR(CDCl$_3$, TMS)

δ (ppm): 7.15–7.5 (7H, m), 4.77 (2H, s), 3.92 (3H, s), 3.38 (3H, s), 2.47 (3H, s)

PRODUCTION EXAMPLE 27

A suspension of 0.15 g (0.92 mmol) of 4-chlorophenylboronic acid, 0.28 g (0.84 mmol) of 4-(5-bromo-2-chlorobenzyl)-5-methoxy-2-methyl-2,4-dihydro-3H-1,2,4-triazol-3-one (the compound 501 of the present invention, produced in the following Production Example 28), 1 mg of (0.004 mmol) of palladium (II) acetate, 0.29 g (2.1 mmol) of potassium carbonate and 0.27 g (0.84 mmol) of tetrabutylammonium bromide in 5 ml of water was vigorously stirred under a stream of nitrogen and stirred under an atmosphere of nitrogen at 75° C. (bath temperature) for 1 hour. Water was added to the reaction mixture and the mixture was extracted with ethyl acetate. The organic layer was dried and concentrated. The residue (0.32 g) was subjected to silica gel thin layer chromatography (developed with n-hexane:ethyl acetate=1:2) to obtain 0.23 g of 4-{2-chloro-5-(4-chlorophenyl)benzyl}-5-methoxy-2-menthyl-2,4-dihydro-3H-1,2,4-triazol-3-one (the compound 19 of the present invention) as white powder.

$^1$H-NMR(CDCl$_3$, TMS)

δ (ppm): 7.2–7.5 (7H, m), 4.90 (2H, s), 3.94 (3H, s), 3.41 (3H, s)

PRODUCTION EXAMPLE 28

To a solution of 0.75 g (2.35 mmol) of 4-(5-bromo-2-chlorobenzyl)-5-methoxy-2,4-dihydro-3H-1,2,4-triazol-3-one (produced in the following Reference Production Example 12) and 0.40 g (2.82 mmol) of methyl iodide in 8 ml of dry N,N-dimethylformamide was added 113 mg (2.82 mmol) of sodium hydride (60% oil dispersion) with ice-cooling. After vigorous bubbling ceased, the mixture was removed from an ice bath and stirred for 2 hours. Ice water was added to the reaction mixture and the mixture was extracted with a mixed solvent of tert-butyl methyl ether and ethyl acetate. The organic layer was washed twice with water, dried and concentrated. To the solid residue (0.80 g), n-hexane was added, and the solid was thoroughly washed, then cooled, collected by filtration and dried to obtain 0.65 g of 4-(5-bromo-2-chlorobenzyl)-5-methoxy-2-methyl-2,4-dihydro-3H-1,2,4-triazol-3-one (the compound 501 of the present invention) as white powder.

$^1$H-NMR(CDCl$_3$, TMS)

δ (ppm): 7.2–7.4 (3H, m), 4.81 (2H, s), 3.94 (3H, s), 3.42 (3H, s)

Reference Production Example 12

(1) To a solution of 6.20 g (25 mmol) of 5-bromo-2-chlorobenzoic acid in 10 ml of dry tetrahydrofuran was added little by little 33.3 ml of borane-tetrahydrofuran complex (1.0 M tetrahydrofuran solution) over 15 minutes with ice-cooling under an atmosphere of nitrogen. The mixture was stirred for 2 hours with ice-cooling and then stirred at room temperature for 17 hours. To the mixture was added dropwise 8 ml of water and then 6 g of potassium carbonate portionwise was added thereto with ice-cooling. Water and tert-butyl methyl ether were added thereto and the mixture was separated. The water layer was extracted twice with tert-butyl methyl ether, and the organic layers were combined, dried and concentrated. To the residue (4.34 g), n-hexane was added to deposit crystals. The resultant crystals were cooled, collected by filtration and dried to obtain 2.08 g of 5-bromo-chlorobenzylalcohol as crystals.

$^1$H-NMR(CDCl$_3$, TMS)

δ (ppm): 7.66 (1H, d), 7.37 (1H, dd), 7.21 (1H, d), 4.76 (2H, s), 1.97 (1H, br s)

(2) To a solution of 2.08 g (9.39 mol) of 5-bromo-2-chlorobenzylalcohol in 30 ml of dry diethyl ether was added dropwise 1.27 g (4.23 mmol) of phosphorous tribromide with ice-cooling. The mixture was stirred with ice-cooling for 3 hours and stirred at room temperature for 1.5 hours. To the reaction solution were added ice water and then tert-butyl methyl ether. The mixture was stirred for 30 minutes and separated. The organic layer was washed successively with an about 5% aqueous solution of sodium bicarbonate and water, then dried and concentrated. The solid residue (1.99 g) was subjected to silica gel column chromatography (eluted with n-hexane) to obtain 1.88 g of 5-bromo-2-chlorobenzylbromide as flocculent crystals.

$^1$H-NMR(CDCl$_3$, TMS)

δ (ppm): 7.58 (1H, d), 7.38 (1H, dd), 7.25 (1H, d), 4.51 (2H, s)

(3) To a solution of 0.91 g (7.93 mmol) of 5-methoxy-2,4-dihydro-3H-1,2,4-triazol-3-one in 8 ml of dry acetonitrile was added 0.96 g (6.94 mmol) of potassium carbonate. To the mixture was added dropwise a solution of 1.88 g (6.61 mmol) of 5-bromo-2-chlorobenzylbromide in 20 ml of dry acetonitrile at 55° C. After the mixture was stirred at 55° C. for 5 hours, water was added to the reaction mixture and the mixture was extracted with ethyl acetate. The organic layer was washed with water, dried and concentrated. To the resultant solid residue (1.90 g) was added cold tert-butyl methyl ether and the solid was thoroughly washed, collected by filtration and dried to obtain 0.75 g of 4-(5-bromo-2-chlorobenzyl)-5-methoxy-2,4-dihydro-3H-1,2,4-triazol-3-one as white powder.

$^1$H-NMR(CDCl$_3$, TMS)

δ (ppm): 8.36 (1H, br s), 7.2–7.5 (3H, m), 4.83 (2H, s), 3.96 (3H, s)

PRODUCTION EXAMPLE 29

A suspension of 0.17 g (1.35 mmol) of phenylboronic acid, 0.36 g (1.07 mmol) of 4-(5-bromo-2-chlorobenzyl)-5-methoxy-2-methyl-2,4-dihydro-3H-1,2,4-triazol-3-one (the compound 501 of the present invention, produced in Production Example 28), 1 mg (0.004 mmol) of palladium (II) acetate, 0.37 g (2.68 mmol) of potassium carbonate and 0.34 g (1.07 mmol) of tetrabutylammonium bromide in 5 ml of water was vigorously stirred under a stream of nitrogen and stirred in an atmosphere of nitrogen at 75° C. (bath temperature) for 1 hour. Water was added to the reaction mixture and the mixture was extracted with ethyl acetate. Then, the organic layer was dried and concentrated. The residue (0.40 g) was subjected to silica gel thin layer chromatography (developed with n-hexane:ethyl acetate=1:2) to obtain 0.28 g of 4-(2-chloro-5-phenylbenzyl)-5-methoxy-2-methyl-2,4-dihydro-3H-1,2,4-triazol-3-one (the compound 487 of the present invention) as a viscous oil (when left at room temperature, it crystallized).

$^1$H-NMR(CDCl$_3$, TMS)

δ (ppm): 7.2–7.6 (8H, m), 4.90 (2H, s), 3.91 (3H, s), 3.39 (3H, s)

PRODUCTION EXAMPLE 30

A solution of 111 mg (0.45 mmol) of 3-phenylbenzylbromide and 77.4 mg (0.60 mmol) of 5-methoxy-2-methyl-2,4-dihydro-3H-1,2,4-triazol-3-one (produced in the following Intermediate Production Example 1) in 2 ml of N,N-dimethylformamide was subjected to nitrogen replacement, followed by quick addition of 24.0 mg (0.60 mmol) of sodium hydride with ice-cooling. The mixture was stirred for 1 hour and further stirred at room temperature overnight. To the reaction mixture was added tert-butyl methyl ether and the mixture was washed with water, dried and concentrated. The residue was subjected to silica gel column chromatography (eluted with n-hexane:ethyl acetate=2:1 and then 1:1) to obtain 51 mg (0.17 mmol) of 5-methoxy-2-methyl-4-(3-phenylbenzyl)-2,4-dihydro-3H-1,2,4-triazol-3-one (the compound 1 of the present invention).

The $^1$H-NMR(CDCl$_3$, TMS) spectrum data agreed with those described in Production Example 1.

Also, as a by-product (eluted with n-hexane:ethyl acetate=2:1), 53 mg (0.18 mmol) of 5-methoxy-2-methyl-3-(3-phenylbenzyloxy)-1,2,4-triazole was obtained.

$^1$H-NMR(CDCl$_3$, TMS)

δ (ppm): 7.36–7.65 (9H, m), 5.44 (2H, s), 3.91 (3H, s), 3.50 (3H, s)

PRODUCTION EXAMPLE 31

According to the same manner as described in Production Example 30, except that 118 mg of 2-methyl-5-phenylbenzylbromide is used in place of 111 mg of 3-phenylbenzylbromide, 5-methoxy-2-methyl-4-(2-methyl-5-phenylbenzyl)-2,4-dihydro-3H-1,2,4-triazol-3-one (the compound 6 of the present invention) is obtained.

PRODUCTION EXAMPLE 32

A mixture of 624 mg (2.0 mmol) of 4-(5-bromo-2-methylbenzyl)-5-methoxy-2-methyl-2,4-dihydro-3H-1,2,4-triazol-3-one (the compound 299 of the present invention), 1.00 g (7.1 mmol) of triethylsilylacetylene, 59 mg (0.084 mmol) of PdCl$_2$(PPh$_3$)$_2$, 32 mg (0.17 mmol) of copper (I) iodide, 90 mg (0.34 mmol) of triphenylphosphine and 1.5 g of triethylamine in 8 ml of acetonitrile was heated under reflux under an atmosphere of nitrogen for 4 hours. After cooling to room temperature, the reaction mixture was diluted with tert-butyl methyl ether, washed with water, dried and concentrated. The residue was subjected to silica gel column chromatography (eluted with hexane:ethyl acetate=3:1) to obtain 0.68 g (1.83 mmol). of 4-{5-(2-triethylsilyl)ethynyl-2-methylbenzyl}-5-methoxy-2-methyl-2,4-dihydro-3H-1,2,4-triazol-3-one (the compound 459 of the present invention).

$^1$H-NMR(CDCl$_3$, TMS)

δ (ppm): 7.30 (1H, dd, J=8.2 Hz), 7.23 (1H, s), 7.09 (1H, d, J=8 Hz), 4.67 (2H, s), 3.92 (3H, s), 3.40 (3H, s), 2.39 (3H, s), 1.04 (9H, t, J=8 Hz), 0.67 (6H, q, J=8 Hz)

PRODUCTION EXAMPLE 33

A mixture of 624 mg (2.0 mmol) of 4-(5-bromo-2-methylbenzyl)-5-methoxy-2-methyl-2,4-dihydro-3H-1,2,4-triazol-3-one (the compound 299 of the present invention), 1.50 g (18.3 mmol) of tert-butyl acetylene, 67 mg (0.095 irmmol) of $PdCl_2(PPh_3)_2$, 33 mg (0.17 mmol) of copper (I) iodide, 106 mg (0.40 mmol) of triphenylphosphine and 1.5 g of triethylamine in 8 ml of acetonitrile was stirred at room temperature under an atmosphere of nitrogen for 31 hours. The reaction mixture was diluted with ethyl acetate, washed with water, dried and concentrated. The residue was subjected to silica gel column chromatography (eluted with hexane:ethyl acetate=6:1) to obtain 0.21 g (0.66 mmol) of 4-{5-(3,3-dimethyl-1-butynyl)-2-methylbenzyl}-5-methoxy-2-methyl-2,4-dihydro-3H-1,2,4-triazol-3-one (the compound 526 of the present invention).

$^1$H-NMR(CDCl$_3$, TMS)

δ (ppm): 7.20 (1H, dd, J=8.2 Hz), 7.14 (1H, d, J=2 Hz), 7.06 (1H, d, J=8 Hz), 4.66 (2H, s), 3.92 (3H, s), 3.40 (3H, s), 2.37 (3H, s), 1.30 (9H, s)

PRODUCTION EXAMPLE 34

A mixture of 624 mg (2.0 mmol) of 4-(5-bromo-2-methylbenzyl)-5-methoxy-2-methyl-2,4-dihydro-3H-1,2,4-triazol-3-one (the compound 299 of the present invention), 700 mg (6.3 mmol) of 3-(trimethylsilyl)-1-propyne, 63 mg (0.095 mmol) of $PdCl_2(PPh_3)_2$, 32 mg (0.17 mmol) of copper (I) iodide, 104 mg (0.40 mmol) of triphenylphosphine and 1.0 g of triethylamine in 6 ml of acetonitrile was stirred at 80° C. under an atmosphere of nitrogen for 9 hours. After cooling to room temperature, the reaction mixture was diluted with tert-butyl methyl ether, washed with water, dried and concentrated. The residue was subjected to silica gel column chromatography (eluted with hexane:ethyl acetate=2:1) to obtain 0.30 g (0.68 mmol) of 4-{5-(3-trimethylsilyl-1-propynyl)-2-methylbenzyl}-5-methoxy-2-methyl-2,4-dihydro-3H-1,2,4-triazol-3-one (the compound 527 of the present invention).

$^1$H-NMR(CDCl$_3$, TMS)

δ (ppm): 7.18 (1H, dd, J=8.2 Hz), 7.12 (1H, s), 7.05 (1H, d, J=8 Hz), 4.66 (2H, s), 3.92 (3H, s), 3.39 (3H, s), 2.37 (3H, s), 1.67 (2H, s), 0.15 (9H, s)

PRODUCTION EXAMPLE 35

To a solution of 4.56 g (14.6 mmol) of 4-(5-bromo-2-methylbenzyl)-5-methoxy-2-methyl-2,4-dihydro-3H-1,2,4-triazol-3-one (the compound 299 of the present invention) in 30 ml of N,N-dimethylformamide were added 4.20 g (16 mmol) of thallium (I) acetate, 9.34 ml (72.6 mmol) of butyl vinyl ether, 604 mg (3.64 mmol) of 1,3-bis(diphenylphosphino)propane, 160 mg (0.72 mmol) of palladium (II) acetate and 2.44 ml (17.5 mmol) of triethylamine and the mixture was stirred at 90° C. under an atmosphere of nitrogen for 8 hours. After the reaction mixture was cooled to room temperature, diluted hydrochloric acid (prepared by mixing 21 ml of concentrated hydrochloric acid and 130 ml of water) was added thereto, and the mixture was stirred for 30 minutes. The reaction mixture was filtered with cotton and washed with chloroform, and the filtrate was separated. After the water layer was extracted with chloroform once again, the organic layers were combined, washed with water (twice), dried and concentrated. Then, to the semisolid residue was added a mixture of equal amounts of tert-butyl methyl ether and hexane and the mixture was stirred at room temperature for a while. The solid was collected by filtration to obtain 2.58 g of 4-(5-acetyl-2-methylbenzyl)-5-methoxy-2-methyl-2,4-dihydro-3H-1,2,4-triazol-3-one (the compound 73 of the present invention) as pale yellow powder.

$^1$H-NMR(CDCl$_3$, TMS)

δ (ppm): 7.75–7.85 (2H, m), 7.25 (1H, d), 4.75 (2H, s), 3.94 (3H, s), 3.39 (3H, s), 2.56 (3H, s), 2.47 (3H, s)

PRODUCTION EXAMPLE 36

To a solution of 275 mg of 4-(5-acetyl-2-methylbenzyl)-5-methoxy-2-methyl-2,4-dihydro-3H-1,2,4-triazol-3-one (the compound 73 of the present invention, produced in Production Example 35) in 4 ml of methanol were added 134 mg (1.2 mmol) of propoxyamine hydrochloride and 95 mg (1.2 mmol) of pyridine and the mixture was stirred at room temperature for 8 hours. After most of the methanol was removed, to the residue was added ethyl acetate and it was washed successively with diluted hydrochloric acid, an aqueous solution of diluted sodium bicarbonate and water. The organic layer was dried and concentrated. The residue (0.31 g) was subjected to silica gel preparative thin layer chromatography (developed with hexane::ethyl acetate=1:1) to obtain 0.27 g of 5-methoxy-2-methyl-4-{2-methyl-5-(1-proxyimino)ethyl}benzyl-2,4-dihydro-3H-1,2,4-triazol-3-one (the compound 303 of the present invention) as an oil.

$^1$H-NMR(CDCl$_3$, TMS)

δ (ppm): 7.45–7.5 (2H, m), 7.14 (1H, d), 4.73 (2H, s), 4.13 (2H, t), 3.92 (3H, s), 3.38 (3H, s), 2.41 (3H, s), 2.19 (3H, s), 1.75 (2H, m), 0.97 (3H, t)

PRODUCTION EXAMPLE 37

To a solution of 275 mg of 4-(5-acetyl-2-methylbenzyl)-5-methoxy-2-methyl-2,4-dihydro-3H-1,2,4-triazol-3-one (the compound 73 of the present invention, produced in Production Example 35) in 4 ml of methanol were added 192 mg (1.2 mmol) of benzyloxyamine hydrochloride and 95 mg (1.2 mmol) of pyridine and the mixture was stirred at room temperature for 2 hours. The reaction mixture was subjected as such to silica gel preparative thin layer chromatography (developed with hexane:ethyl acetate=4:3) to obtain 0.27 g of 4-{5-(1-benzyloxyimino)ethyl-2-methyl}benzyl-5-methoxy-2-methyl-2,4-dihydro-3H-1,2,4-triazol-3-one (the compound 314 of the present invention) as an oily matter.

$^1$H-NMR(CDCl$_3$, TMS)

δ (ppm): 7.25–7.5 (7H, m), 7.12 (1H, d), 5.21 (2H, s), 4.71 (2H, s), 3.88 (3H, s), 3.37 (3H, s), 2.40 (3H, s), 2.21 (3H, s)

PRODUCTION EXAMPLE 38

A mixture of 524 mg (1.68 mmol) of 4-(5-bromo-2-methylbenzyl)-5-methoxy-2-methyl-2,4-dihydro-3H-1,2,4-triazol-3-one (the compound 299 of the present invention), 534 mg (5.22 mmol) of trimethylsilylacetylene, 19 mg (0.085 mmol) of palladium (II) acetate, 37 mg (0.14 mmol) of triphenylphosphine and 1.5 ml of triethylamine in 2 ml of toluene was stirred at bath temperature of 80 to 90° C. under an atmosphere of nitrogen for 3 hours. After cooling to room temperature, the reaction mixture was filtered and washed with toluene. The filtrate was concentrated, and the residue (0.79 g) was subjected to silica gel preparative thin layer chromatography (developed with hexane:ethyl acetate=1:2) to obtain 0.28 g 4-{5-(2-trimethylsilyl)ethynyl-2-methylbenzyl}-5-methoxy-2-methyl-2,4-dihydro-3H-1,2,4-triazol-3-one (the compound 457 of the present invention) (including raw compound 4-(5-bromo-2-methylbenzyl)-5-methoxy-2-methyl-2,4-dihydro-3H-1,2,4-triazol-3-one as an impurity).

¹H-NMR(CDCl₃, TMS)

δ (ppm): 7.2–7.35 (2H, m), 7.08 (1H, d), 4.67 (2H, s), 3.92 (3H, s), 3.40 (3H, s), 2.38 (3H, s), 0.24 (9H, s)

PRODUCTION EXAMPLE 39

To a solution of 0.44 g (1.4 mmol) of 4-(5-bromo-2-methylbenzyl)-5-methoxy-2-methyl-2,4-dihydro-3H-1,2,4-triazol-3-one (the compound 299 of the present invention) in 8 ml of N,N-dimethylformamide were added 30 mg (0.042 mmol) of PdCl₂(PPh₃)₂ and 0.12 g (1.4 mmol) of copper (II) oxide powder and the mixture was stirred at 80° C. under an atmosphere of nitrogen for 30 minutes. To the reaction mixture was added a solution of 0.48 g (2.0 mmol) of trimethyl(2-pyridyl)tin in 4 ml of N,N-dimethylformamide and the mixture was stirred at 80° C. under an atmosphere of nitrogen for 3 hours. After cooling to room temperature, the reaction mixture was poured into ice water, and ethyl acetate was added thereto. The mixture was filtered with cotton and separated, and the organic layer was washed twice with water, dried and concentrated. The residue (0.43 g) was subjected to silica gel preparative thin layer chromatography (developed with ethyl acetate) to obtain 0.18 g of 5-methoxy-2-methyl-4-{2-methyl-5-(2-pyridyl)benzyl}-2,4-dihydro-3H-1,2,4-triazol-3-one (the compound 152 of the present invention) as a viscous oil.

¹H-NMR(CDCl₃, TMS)

δ (ppm): 8.65 (1H, m), 7.8–7.9 (2H, m), 7.6–7.75 (2H, m), 7.15–7.3 (2H, m), 4.79 (2H, m), 3.91 (3H, s), 3.39 (3H, s), 2.45 (3H, s)

PRODUCTION EXAMPLE 40

To a solution of 1.80 g (5.77 mmol) of 4-(5-bromo-2-methylbenzyl)-5-methoxy-2-methyl-2,4-dihydro-3H-1,2,4-triazol-3-one (the compound 299 of the present invention), 0.89 g (5.77 mmol) of 4-chlorobenzonitrile, 75 mg (0.577 mmol) of anhydrous nickel (II) chloride, and 0.31 g (1.15 mmol) of triphenylphosphine in 6 ml of pyridine was heated to 80° C. under an atmosphere of nitrogen. Then, 0.79 g (12.1 mmol) of zinc powder was added thereto, and the mixture was stirred at 80° C. under an atmosphere of nitrogen for 5 hours. After cooling to room temperature, the mixture was poured into a mixture of diluted hydrochloric acid (prepared by mixing 72 ml of water and 8 ml of concentrated hydrochloric acid) and ice, and ethyl acetate was added thereto. The resultant mixture was filtered with cotton and separated, and the organic layer was washed successively with an aqueous solution of sodium bicarbonate and water, then dried and concentrated. The residue (2.17 g) was subjected to silica gel column chromatography (eluted with hexane:ethyl acetate=2:1and then 1:1 for eluting impurities and then 1:2 for eluting the desired compound) to obtain 0.65 g of 4-{5-(4-cyanophenyl)-2-methylbenzyl}-5-methoxy-2-methyl-2,4-dihydro-3H-1,2,4-triazol-3-one (the compound 489 of the present invention) as crystals.

¹H-NMR(CDCl₃, TMS)

δ (ppm): 7.6–7.75 (4H, m), 7.4–7.45 (2H, m), 7.28 (1H, d), 4.78 (2H, s), 3.94 (3H, s), 3.39 (3H, s), 2.46 (3H, s)

PRODUCTION EXAMPLE 41

To a solution of 3.33 g (11.0 mmol) of 4-(5-bromo-2-fluorobenzyl)-5-methoxy-2,4-dihydro-3H-1,2,4-triazol-3-one (produced in the following Reference Production Example 13) and 1.88 g (13.2 mmol) of methyl iodide in 30 ml of N,N-dimethyformamide was added 0.53 g (13.2 mmol) of sodium hydride (60% oil dispersion) portionwise with ice-cooling. After vigorous bubbling ceased, an ice bath was removed and the mixture was stirred at room temperature for 3 hours. To the reaction mixture, ice water was added, and the mixture was extracted with a mixed solvent of ethyl acetate and tert-butyl methyl ether. The organic layer was washed with water (twice), dried and concentrated. Then, to the solid residue was added hexane, and the mixture was stirred for a while and cooled. The solid was collected by filtration to obtain 2.77 g of 4-(5-bromo-2-fluorobenzyl)-5-methoxy-2-methyl-2,4-dihydro-3H-1,2,4-triazol-3-one (the compound 528 of the present invention) as white powder.

¹H-NMR(CDCl₃, TMS)

δ (ppm): 7.35–7.45 (2H, m), 6.95 (1H, t), 4.75 (2H, s), 3.95 (3H, s), 3.39 (3H, s)

Reference Production Example 13

(1) To a solution of 9.45 g (50 mmol) of 5-bromo-2-fluorotoluene in 30 ml of carbon tetrachloride were added 9.08 g (50 mmol) of N-bromosuccinimide and 0.26 g (1 mmol) of 1,1'-azobis(cyclohexane-1-carbonitrile) and the mixture was heated under reflux for 5 hours. After cooling to room temperature, the reaction mixture was filtered, and the filtrate was concentrated to obtain 13.54 g of crude 5-bromo-2-fluorobenzylbromide as liquid.

¹H-NMR(CDCl₃, TMS)

δ (ppm): 7.35–7.6 (2H, m), 6.96 (1H, t), 4.44 (2H, s)

(2) To a solution of 5.75 g (50 mmol) of 5-methoxy-2,4-dihydro-3H-1,2,4-triazol-3-one in 30 ml of acetonitrile was added 6.21 g (45 mmol) of potassium carbonate. A solution of 13.54 g of crude 5-bromo-2-fluorobenzylbromide in 50 ml of acetonitrile was added dropwise at 55° C. thereto. After the mixture was stirred at 55° C. for 2.5 hours, 1.15 g of 5-methoxy-2,4-dihydro-3H-1,2,4-triazol-3-one and 1.24 g of potassium carbonate were added thereto and then the mixture was stirred at 55° C. for 3 hours. Water was added to the reaction mixture and the mixture was extracted with a mixed solvent of ethyl acetate and tert-butyl methyl ether. The organic layer was washed with water, dried and concentrated. Then, to the semisolid residue (13.37 g) was added a mixture of equal amounts of tert-butyl methyl ether and hexane, then stirred for a while and cooled. The resultant solid was collected by filtration to obtain 3.64 g of 4-(5-bromo-2-fluorobenzyl)-5-methoxy-2,4-dihydro-3H-1,2,4-triazol-3-one as white powder.

¹H-NMR(CDCl₃, TMS)

δ (ppm): 8.26 (1H, br), 7.35–7.45 (2H, m), 6.94 (1H, t), 4.76 (2H, s), 3.96 (3H, s)

PRODUCTION EXAMPLE 42

A suspension of 0.17 g (1.35 mmol) of phenylboronic acid, 338 mg (1.07 mmol) of 4-(5-bromo-2-fluorobenzyl)-5-methoxy-2-methyl-2,4-dihydro-3H-1,2,4-triazol-3-one (the compound 528 of the present invention, produced in Production Example 41), 1 mg (0.004 mmol) of palladium (II) acetate, 0.37 g (2.68 mmol) of potassium carbonate and 0.34 g (1.07 mmol) of tetrabuthyammonium bromide in 5 ml of water was vigorously stirred under an stream of nitrogen and stirred at bath temperature of 75° C. under an atmosphere of nitrogen for 1 hour. Water was added to the reaction mixture and the mixture was extracted with ethyl acetate. The organic layer was dried and concentrated. The residue (0.35 g) was subjected to silica gel preparative thin layer chromatography (developed with hexane:ethyl acetate=1:2) to obtain 0.27 g of 4-(2-fluoro-5-phenylbenzyl)-5-methoxy-2-methyl-2,4-dihydro-3H-1,2,4-triazol-3-one (the compound 529 of the present invention) as an oily matter.

$^1$H-NMR(CDCl$_3$, TMS)

δ (ppm): 7.3–7.55 (7H, m), 7.11 (1H, t), 4.84 (2H, s), 3.94 (3H, s), 3.37 (3H, s)

PRODUCTION EXAMPLE 43

A mixture of 195 mg (0.691 mmol) of 4,4,5,5-tetramethyl-2-{3-(4-pyrimidinyl)phenyl}-1,3,2-dioxoborolane (produced in the following Reference Production Example 14), 200 mg (0.692 mmol) of 4-(5-bromo-2-methylbenzyl)-5-methoxy-2-methyl-2,4-dihydro-3H-1,2,4-triazol-3-one (the compound 299 of the present invention, produced in Production Example 20), 734.mg (3.46 mmol) of tripotassium phosphate hydrate, 28 mg (0.03 mmol) of {1,1'-bis(diphenylphosphino)ferrocene}dichloropalladium (II) methylene chloride complex, 7 mg (0.03 mmol) of palladium (II) acetate and 3 ml of ethyleneglycoldimethyl ether was stirred at 83° C. for 4 hours. Then, the mixture was cooled to room temperature. Then, saturated brine was added and the mixture was extracted with ethyl acetate. The organic layer was dried and concentrated. The residue was subjected to silica gel preparative thin layer chromatography (developed with ethyl acetate:isopropanol=12:1) to obtain 102 mg of 5-methoxy-2-methyl-4-{2-methyl-5-[3-(4-pyrimidinyl)phenyl]}benzyl-2,4-dihydro-3H-1,2,4-triazol-3-one (the compound 534 of the present invention).

$^1$H-NMR(CDCl$_3$, TMS)

δ (ppm): 9.28 (1H, d, J=1.3 Hz), 8.80 (1H, d, J=5.4 Hz), 8.28 (1H, t, J=1.8 Hz), 8.02–8.05 (1H, m), 7.77 (1H, dd, J=5.4 Hz, J=1.5 Hz), 7.67–7.70 (1H, m), 7.48–7.60 (3H, m), 7.29 (1H, m), 4.80 (2H, s), 3.95 (3H, s), 3.39 (3H, s), 2.47 (3H, s)

Reference Production Example 14

(1) A mixture of 9.0 g (59.9 mmol) of 3-bromoacetophenone, 17.1 g (118 mmol) of N,N',N''-methylidynetrisformamide, 0.57 g (3.0 mmol) of p-toluenesulfonic acid and 27 g of formamide was stirred at 160° C. for 2 hours. After the reaction mixture was cooled to room temperature, a 5% aqueous solution of caustic soda was added thereto, and the mixture was adjusted to pH 4 with a 5% aqueous hydrochloric acid and extracted with ethyl acetate. The organic layer was washed successively with a saturated aqueous solution of ammonium chloride and saturated brine, then dried and concentrated. The resultant solid residue was recrystallized from a mixture ethanol:water=1:2 to obtain 2.49 g of 4-(3-bromophenyl)pyrimidine.

$^1$H-NMR(CDCl$_3$, TMS)

δ (ppm): 9.29 (1H, d, J=0.9 Hz), 8.81 (1H, d, J=5.4 Hz), 8.28 (1H, t, J=1.7 Hz), 8.01 (1H, d J=7.8 Hz), 7.71 (1H, dd, J=5.1, 1.2 Hz), 7.7 (1H, dd), 7.40 (1H, t, J=7.8 Hz)

(2) A mixture of 0.7 g (6.31 mmol) of 4-(3-bromophenyl)pyrimidine, 0.91 g (3.9 mmol) of bis(pinacolate)diborone, 0.121 g (0.149 mmol) of {1,1'-bis(diphenylphosphino)ferrocene}dichloropalladium (II) methylene chloride complex, 0.88 g (9.0 mmol) of potassium acetate and dimethylsulfoxide (2 ml) was stirred at 80° C. for 4 hours. After the mixture was cooled to room temperature, water was added thereto, and the mixture was extracted with ethyl acetate. The organic layer was washed successively with water and saturated brine, then dried and concentrated. The residue was subjected to silica gel column chromatography (eluted with a mixed solvent of hexane and ethyl acetate) to obtain 520 mg of 4,4,5,5-tetramethyl-2-{3-(4-pyrimidinyl)phenyl}-1,3,2-dioxoborolane.

$^1$H-NMR(CDCl$_3$, TMS)

δ (ppm): 9.3 (1H, s), 8.8 (1H, d), 8.5 (1H, s), 8.2 (1H, d), 8.0 (1H, d), 7.8 (1H, d), 7.5 (1H, t), 1.37 (12H, s)

PRODUCTION EXAMPLE 44

A mixture of 300 mg (0.835 mmol) of 5-methoxy-2-methyl-4-{2-methyl-5-(4,4,5,5-tetramethyl-1,3,2-dioxoborolanyl)}benzyl-2,4-dihydro-3H-1,2,4-triazol-3-one (produced in the following Intermediate Production Example 2), 173 mg (1.09 mmol) of 2-bromopyrimidine, 890 mg (4.19 mml) of tripotassium phosphate hydrate, 34 mg (0.042 mmol) of {1,1'-bis(diphenylphosphino)ferrocene}dichloropalladium (II) methylene chloride complex, 9 mg (0.04 mmol) of palladium (II) acetate and 4 ml of ethyleneglycoldimethyl LA ether was stirred at 83° C. for 4 hours. After the mixture was cooled to room temperature, Celite and ethyl acetate were added thereto, and the resultant mixture was filtered, and the filtrate was concentrated. The residue was subjected to silica gel preparative thin layer chromatography (eluted with isopropyl alcohol:ethyl acetate=1:99) to obtain 109 mg of 5-methoxy-2-methyl-4-{2-methyl-5-(2-pyrimidinyl)benzyl}-2,4-dihydro-3H-1,2,4-triazol-3-one (the compound 166 of the present invention).

$^1$H-NMR(CDCl$_3$, TMS)

δ (ppm): 8.77 (2H, dd, J=4.9 Hz, J=0.8 Hz), 8.24–8.29 (2H, m), 7.14–7.31 (2H, m), 4.81 (2H, s), 3.92 (3H, s), 3.40 (3H, s), 2.47 (3H, s)

PRODUCTION EXAMPLE 45

A suspension of 2.00 g (8.77 mmol) of 3-(benzyloxy)phenylboronic acid, 2.49 g (7.97 mmol) of 4-(5-bromo-2-methylbenzyl)-5-methoxy-2-methyl-2,4-dihydro-3H-1,2,4-triazol-3-one (the compound 299 of the present invention), 8.4 mg (0.037 mmol) of palladium (II) acetate, 2.75 g (19.9 mmol) of potassium carbonate and 2.60 g (8.07 mmol) of tetrabutylammonium bromide in 18.5 ml of water was vigorously stirred under a stream of nitrogen and stirred at 70° C. under an atmosphere of nitrogen for 1 hour. To the reaction mixture was added water and the mixture was extracted with ethyl acetate. The organic layer was washed with brine, dried and concentrated. The residue (3.68 g) was subjected to silica gel column chromatography (developed with hexane:ethyl=1:2) to obtain 2.93 g of 4-{5-(3-benzyloxy)phenyl-2-methyl}benzyl-5-methoxy-2-methyl-2,4-dihydro-3H-1,2,4-triazol-3-one (the compound 530 of the present invention) as a viscous oily matter.

$^1$H-NMR(CDCl$_3$, TMS)

δ (ppm): 7.1–7.5 (11H, m), 6.95 (1H, m), 5.11 (2H, s), 4.77 (2H, s), 3.92 (3H, s), 3.39 (3H, s), 2.44 (3H, s)

PRODUCTION EXAMPLE 46

A suspension of 0.23 g (1.16 mmol) of 3-phenylphenylboronic acid, 0.34 g (1.09 mmol) of 4-(5-bromo-2-methylbenzyl)-5-methoxy-2-methyl-2,4-dihydro-3H-1,2,4-triazol-3-one (the compound 299 of the present invention), 2.3 mg (0.01 mmol) palladium (II) acetate, 0.37 g (2.68 mmol) of potassium carbonate and 0.34 g (1.07 mmol) of tetrabutylammonium bromide in 5 ml of water was vigorously stirred under a stream of nitrogen and stirred at 70° C. under an atmosphere of nitrogen for 1 hour. To the reaction mixture was added water and the mixture was extracted with ethyl acetate. The organic layer was washed with brine, dried and concentrated. The residue (0.48 g) was subjected to silica gel preparative thin layer chromatography (developed with hexane:ethyl acetate=1:2) to obtain 0.32 g of 5-methoxy-2-methyl-4-{2-methyl-5-(3-phenyl) phenyl}benzyl-2,4-dihydro-3H-1,2,4-triazol-3-one (the compound 531 of the present invention) as a viscous oil.

$^1$H-NMR(CDCl$_3$, TMS)

δ (ppm): 7.2–7.8 (12H, m), 4.79 (2H, s), 3.93 (3H, s), 3.39 (3H, s), 2.46 (3H, s)

PRODUCTION EXAMPLE 47

A suspension of 0.22 g (1.16 mmol) of 3,4-dichlorophenylboronic acid, 0.34 g (1.09 mmol) of 4-(5-bromo-2-methylbenzyl)-5-methoxy-2-methyl-2,4-dihydro-3H-1,2,4-triazol-3-one (the compound 299 of the present invention), 3.9 mg (0.016 mmol) of palladium (II) acetate, 0.37 g (2.68 mmol) of potassium carbonate and 0.34 g (1.07 mmol) of tetrabutylammonium bromide in 5 ml of water was vigorously stirred under a stream of nitrogen and stirred at 70° C. under an atmosphere of nitrogen for 1 hour. To the reaction mixture was added water and the mixture was extracted with chloroform. The organic layer was washed with brine, dried and concentrated. The residue (0.84 g) was subjected to silica gel preparative thin layer chromatography (developed with chloroform:ethyl acetate=1:2) to obtain 0.27 g of 4-{5-(3,4-dichlorophenyl)-2-methyl}benzyl-5-methoxy-2-methyl-2,4-dihydro-3H-1,2,4-triazol-3-one (the compound 45 of the present invention) as solid.

$^1$H-NMR(CDCl$_3$, TMS)

δ (ppm): 7.60 (1H, d), 7.48 (1H, d), 7.3~7.4 (3H, m), 7.24 (1H, d), 4.77 (2H, s), 3.94 (3H, s), 3.40 (3H, s), 2.45 (3H, s)

PRODUCTION EXAMPLE 48

A suspension of 0.18 g (1.14 mmol) of 3,5-difluorophenylboronic acid, 0.34 g (1.09 mmol) of 4-(5-bromo-2-methylbenzyl)-5-methoxy-2-methyl-2,4-dihydro-3H-1,2,4-triazol-3-one (the compound 299 of the present invention), 7.1 mg (0.029 mmol) of palladium (II) acetate, 0.37 g (2.68 mmol) of potassium carbonate and 0.34 g (1.07 mmol) of tetrabutylammonium bromide in 5 ml of water was vigorously stirred under a stream of nitrogen and stirred at 70° C. under an atmosphere of nitrogen for 1 hour. To the reaction mixture, water was added, and the mixture was extracted with chloroform. The organic layer was washed with brine, dried and concentrated. The residue (0.78 g) was subjected to silica gel preparative thin layer chromatography (developed with chloroform:ethyl acetate=1:2) to obtain 0.25 g of 4-{5-(3,5-difuluorophenyl)-2-methyl}benzyl-5-methoxy-2-methyl-2,4-dihydro-3H-1,2,4-triazol-3-one (the compound 532 of the present invention) as white powder.

$^1$H-NMR(CDCl$_3$, TMS)

δ (ppm): 7.2–7.45 (3H, m), 6.95–7.10 (2H, m), 6.77 (1H, tt), 4.77 (2H, s), 3.94 (3H, s), 3.40 (3H, s), 2.45 (3H, s)

PRODUCTION EXAMPLE 49

A suspension of 0.16 g (1.16 mmol) of 2-fluorophenylboronic acid, 0.34 g (1.09 mmol) of 4-(5-bromo-2-methylbenzyl)-5-methoxy-2-methyl-2,4-dihyro-3H-1,2,4-triazol-3-one (the compound 299 of the present invention), 4.7 mg (0.014 mmol) of palladium (II) acetate, 0.37 g (2.68 mmol) of potassium carbonate and 0.34 g (1.07 mmol) of tetrabutylammonium bromide in 5 ml of water was vigorously stirred under a stream of nitrogen and stirred at 70° C. under an atmosphere of nitrogen for 1 hour. To the reaction mixture, water was added, and the mixture was extracted with chloroform. The organic layer was washed with brine, dried and concentrated. The residue (1.34 g) was subjected to silica gel preparative thin layer chromatography (developed with chloroform:ethyl acetate=1:2) to obtain 0.26 g of $^4$-{5-(2-fluorophenyl)-2-methyl}benzyl-5-methoxy-2-methyl-2,4-dihydro-3H-1,2,4-triazol-3-one (the compound 533 of the present invention) as an oil.

$^1$H-NMR(CDCl$_3$, TMS)

δ (ppm): 7.05~7.45 (7H, m), 4.77 (2H, s), 3.93 (3H, s), 3.39 (3H, s), 2.45 (3H, s)

PRODUCTION EXAMPLE 50

A suspension of 0.16 g (1.16 mmol) of 3-fluorophenylboronic acid, 0.34 g (1.09 mmol) of 4-(5-bromo-2-methylbenzyl)-5-methoxy-2-methyl-2,4-dihydro-3H-1,2,4-triazol-3-one (the compound 299 of the present invention), 7.1 mg (0.022 mmol) of palladium (II) acetate, 0.37 g (2.68 mmol) of potassium carbonate and 0.34 g (1.07 mmol) of tetrabutylammonium bromide in 5 ml of water was vigorously stirred under a stream of nitrogen and stirred at 70° C. under an atmosphere of nitrogen for 1 hour. To the reaction mixture, water was added, and the mixture was extracted with chloroform. The organic layer was washed with brine, dried and concentrated. The residue (0.83 g) was subjected to silica gel preparative thin layer chromatography (developed with chloroform:ethyl acetate=1:2) to obtain 0.29 g of 4-{5-(3-fluorophenyl)-2-methyl}benzyl-5-methoxy-2-methyl-2,4-dihydro-3H-1,2,4-triazol-3-one (the compound 28 of the present invention) as an oil.

$^1$H-NMR(CDCl$_3$, TMS)

δ (ppm): 7.15–7.45 (6H, m), 6.95–7.1 (1H, m), 4.78 (2H, s), 3.94 (3H, s), 3.40 (3H, s), 2.45 (3H, s)

PRODUCTION EXAMPLE 51

A suspension of 0.20 g (1.2 mmol) of 3-methylphenylboronic acid, 0.34 g (1.09 mmol) of 4-(5-bromo-2-methylbenzyl)-5-methoxy-2-methyl-2,4-dihydro-3H-1,2,4-triazol-3-one (the compound 299 of the present invention), 4 mg (0.022 mmol) of palladium (II) acetate, 0.37 g (2.7 mmol) of potassium carbonate and 0.35 g (1.09 mmol) of tetrabutylammonium bromide in 5 ml of water was vigorously stirred under a stream of nitrogen and stirred at 70° C. under an atmosphere of nitrogen for 2 hours. To the reaction mixture, brine was added, and the mixture was extracted with chloroform. The organic layer was washed with brine, dried and concentrated. The residue (0.94 g) was subjected to silica gel preparative thin layer chromatography (developed with chloroform:ethyl acetate=2:1) to obtain 0.33 g of 4-{5-(3-methylphenyl)-2-methyl}benzyl-5-methoxy-2-methyl-2,4-dihydro-3H-1,2,4-triazol-3-one (the compound 50 of the present invention) as an oil.

$^1$H-NMR(CDCl$_3$, TMS)

δ (ppm): 7.1–7.45 (7H, m), 4.79 (2H, s), 3.92 (3H, s), 3.39 (3H, s), 2.44 (3H, s), 2.41 (3H, s)

PRODUCTION EXAMPLE 52

A mixture of 437 mg (1.4 mmol) of 4-(5-bromo-2-methylbenzyl)-5-methoxy-2-methyl-2,4-dihydro-3H-1,2,4-triazol-3-one (the compound 299 of the present invention), 325 mg (2.8 mol) of benzylacetylene, 41 mg (0.058 mmol) of PdCl$_2$(PPh$_3$)$_2$, 33 mg (0.17 mmol) of copper (I) iodide, 82 mg (0.31 mmol) of triphenylphosphine and 0.80 g of triethylamine in 4 ml of acetonitrile was heated under reflux under an atmosphere of nitrogen for 9 hours. After cooling to room temperature, the reaction mixture was diluted with tert-butyl ether, washed with water, dried and concentrated. The residue was subjected to silica gel column chromatography (eluted with hexane:ethyl acetate=2:1) to obtain 0.25 g of 4-{5-(3-phenyl-1-propynyl)-2-methylbenzyl}-5-methoxy-2-methyl-2,4-dihydro-3H-1,2,4-triazol-3-one (the compound 535 of the present invention).

$^1$H-NMR(CDCl$_3$, TMS)

δ (ppm): 7.15–7.45 (7H, m), 7.09 (1H, d, J=8 Hz), 4.68 (2H, s), 3.92 (3H, s), 3.40 (3H, s), 2.38 (3H, s)

PRODUCTION EXAMPLE 53

To a solution of 9.24 g (31.1 mmol) of triphosgene in 50 ml of methylene chloride was added dropwise a solution of 4.41 g (15.6 mmol) of 1,1-dimethyl-4-(2-methyl-5-phenylbenzyl)semicarbazide (produced in the following Reference Production Example 15) in 35 ml of methylene chloride with ice-cooling. The mixture was removed from an ice bath, allowed to warm to room temperature, and heated under reflux for 6 hours. After allowing to cool to room temperature, the reaction mixture was poured into 300 ml of an about 5% aqueous solution of sodium bicarbonate, and the mixture was stirred for 1 hour. The organic layer was washed with water, dried and concentrated. The residue was subjected to silica gel column chromatography (developed with n-hexane:ethyl acetate=2:1and then 1:1) to obtain 2.01 g (6.4 mmol) of 5-chloro-2-methyl-4-(2-methyl-5-phenylbenzyl)-2,4-dihydro-3H-1,2,4-triazol-3-one (the compound 7 of the present invention) having a melting point of 115.7° C.

$^1$H-NMR(CDCl$_3$, TMS)

δ (ppm): 7.25–7.55 (8H, m), 4.92 (2H, s), 3.49 (3H, s), 2.44 (3H, s)

Reference Production Example 15

(1) To a solution of 7.83 g (30 mmol) of 2-methyl-5-phenylbenzylbromide in 90 ml of dry tetrahydrofuran, was added 5.84 g (39 mmol) of silver cyanate and the mixture was heated under reflux for 2 hours. The reaction mixture was filtered, and the filtrate was concentrated to obtain 7.11 g of crude 2-methyl-5-phenylbenzylisocyanate.

$^1$H-NMR(CDCl$_3$, TMS)

δ (ppm): 7.25–7.65 (8H, m), 4.53 (2H, s), 2.37 (3H, s)

(2) To a suspension of 7.11 g of crude 2-methyl-5-phenylbenzylisocyanate in 24 ml of toluene was added dropwise 2.10 g (35 mmol) of N,N-dimethylhydrazine with ice-cooling, and the mixture was removed from an ice bath and stirred for 2 hours. The reaction solution was concentrated, and the solid residue was recrystallized from ethanol to obtain 4.41 g (15.6 mmol) of 1,1-dimethyl-4-(2-methyl-5-phenylbenzyl)semicarbazide.

$^1$H-NMR(CDCl$_3$, TMS)

δ (ppm): 7.25–7.65 (8H, m), 6.27 (1H, br), 5.22 (1H, br), 4.48 (2H, d), 2.49 (6H, s), 2.38 (3H, s)

PRODUCTION EXAMPLE 54

A solution of 500 mg (1.59 mmol) of 5-chloro-2-methyl-4-(2-methyl-5-phenylbenzyl)-2,4-dihydro-3H-1,2,4-triazol-3-one (the compound 7 of the present invention, produced in Production Example 53) in 5 ml of N,N-dimethylacetamide was added 1.0 ml of sodium thiomethoxide (15% aqueous solution), and the mixture was stirred at 80° C. for 4.5 hours. Water was added to the reaction mixture and the mixture was extracted with t-butyl methyl ether. The organic layer was washed with water, dried and concentrated. The residue was subjected to silica gel column chromatography (eluted with n-hexane:ethyl acetate=2:1 and then 1:1) to obtain 0.32 g (0.98 mmol) of 5-methylthio-2-methyl-4-(2-methyl-5-phenylbenzyl)-2,4-dihydro-3H-1,2,4-triazol-3-one (the compound 8 of the present invention) having a melting point of 95.6° C.

$^1$H-NMR(CDCl$_3$, TMS)

δ (ppm): 7.25–7.60 (8H, m), 4.86 (2H, s), 3.49 (3H, s), 2.42 (3H, s), 2.41 (3H, s)

PRODUCTION EXAMPLE 55

To a solution of 0.86 g (3.08 mmol) of 5-methyl-4-(2-methyl-5-phenylbenzyl)-2,4-dihydro-3H-1,2,4-triazol-3-one (produced in the following Reference Production Example 16) and 1.31 g (9.24 mmol) of methyl iodide in 20 ml of dry N,N-dimethylformamide was added 0.37 g (9.24 mmol) of sodium hydride (60% oil dispersion) with ice-cooling. After vigorous bubbling ceased, the mixture was removed from an ice bath and stirred at room temperature for 1 hour. After the mixture was cooled again, 200 ml of 5% aqueous hydrochloric acid was added thereto, and the mixture was extracted with t-butyl methyl ether. The organic layer was washed successively with water, a 5% aqueous solution of sodium bicarbonate and saturated brine, then dried and concentrated. The residue was subjected to silica gel column chromatography (developed with n-hexane:ethyl acetate=1:1 then ethyl acetate) to obtain 0.73 g (2.50 mmol) of 2,5-dimethyl-4-(2-methyl-5-phenylbenzyl)-2,4-dihydro-3H-1,2,4-triazol-3-one (the compound 10 of the present invention) having a melting point of 138.9° C.

$^1$H-NMR(CDCl$_3$, TMS)

δ (ppm): 7.10–7.55 (8H, m), 4.87 (2H, s), 3.47 (3H, s), 2.38 (3H, s), 2.05 (3H, s)

Reference Production Example 16

(1) To a solution of 2.47 g (11.1 mmol) of crude 2-methyl-5-phenylbenzylisocyanate in 50 ml of tetrahydrofuran was added 0.82 g of acetohydrazide and the mixture was heated under reflux for 1 hour. After allowing to cool to room temperature, the reaction mixture was concentrated, and the residue was recrystallized from ethanol to obtain 0.93 g (3.13 mmol) of 1-acetyl-4-(2-methyl-5-phenylbenzyl)semicarbazide.

$^1$H-NMR(CDCl$_3$, TMS)

δ (ppm): 7.95 (1H, br), 7.15–7.60 (8H, m), 5.17 (2H, br), 4.48 (2H, d), 2.28 (3H, s), 1.90 (3H, s)

(2) To 10 ml of a 2% aqueous solution of potassium hydroxide was added 0.87 g (2.92 mmol) of 1-acetyl-4-(2-methyl-5-phenhybenzyl)semicarbazide and the mixture was stirred at 90° C. for 3 hours. After allowing to cool to room temperature, the reaction mixture was extracted with ethyl acetate, and the organic layer was washed with water, dried and concentrated. The residue was subjected to silica gel column chromatography (eluted with ethyl acetate) to obtain 0.87 g of 5-methyl-4-(2-methyl-5-phenylbenzyl)-2,4-dihydro-3H-1,2,4-triazol-3-one.

$^1$H-NMR(CDCl$_3$, TMS)

δ (ppm): 9.38 (1H, br), 7.1–7.55 (8H, m), 4.88 (2H, s), 2.38 (3H, s), 2.06 (3H, s)

PRODUCTION EXAMPLE 56

To a solution of 0.36 g (1.17 mmol) of 5-methoxy-4-{1-(2-methyl-5-phenyl)phenylethyl}-2,4-dihydro-3H-1,2,4- triazol-3-one (produced in the following Reference Production Example 17) and 0.22 ml (3.50 mmol) of methyl iodide in 10 ml of dry N,N-dimethylformamide was added 0.14 g (3.50 mmol) of sodium hydride (60% oil dispersion) with ice-cooling. After vigorous bubbling ceased, the reaction mixture was removed from an ice bath and stirred at room temperature for 1 hour. After the mixture was cooled again, 200 ml of 5% aqueous hydrochloric acid was added thereto, and the mixture was extracted with tert-butyl methyl ether. The organic layer was washed with water, a 5% aqueous solution of sodium bicarbonate and saturated brine, then dried and concentrated. The residue was subjected to silica gel preparative thin layer chromatography (developed with n-hexane:ethyl acetate=2:1) to obtain 0.22 g (0.69 mmol) of 5-methoxy-2-methyl-4-{1-(2-methyl-5-phenyl)phenylethyl}-2,4-dihydro-3H-1,2,4-triazol-3-one (the compound 537 of the present invention).

$^1$H-NMR(CDCl$_3$, TMS)

δ (ppm): 7.15–7.85 (8H, m), 5.53 (1H, q), 3.89 (3H, s), 3.35 (3H, s), 2.40 (3H, s), 1.82 (3H, d)

Reference Production Example 17

(1) Five ml of dry diethyl ether was poured into 600 mg of magnesium, and a catalytic amount of iodide was added thereto. The mixture was stirred until the color of the iodide faded and 1.40 ml (22.4 mmol) of methyl iodide was added dropwise thereto. After completion of the addition, the mixture was further stirred for 30 minutes. Then, the reaction mixture was cooled to 0° C. and 4.00 g (20.4 mmol) of 2-methyl-5-phenylbenzaldehyde was slowly added dropwise thereto. After the mixture was stirred for additional 1 hour, an aqueous solution of saturated ammonium chloride was added thereto. Then the mixture was removed from an ice bath, warmed to room temperature and extracted with t-butyl methyl ether. The organic layer was washed with saturated brine, dried and concentrated to obtain 4.33 g (20.38 mmol) of 1-(2-methyl-5-phenyl)phenylethanol.

$^1$H-NMR(CDCl$_3$, TMS)

δ (ppm): 7.15–7.80 (8H, m), 5.19 (1H, q), 2.38 (3H, s), 1.77 (1H, br), 1.52 (3H, d)

(2) To a solution of 4.33 g (20.38 mmol) of 1-(2-methyl-5-phenyl)phenylethanol in dry diethyl ether was added dropwise 2.21 g (8.15 mmol) of phosphorous tribromide with ice-cooling. The mixture was removed from an ice bath and stirred at room temperature for 9 hours. To the reaction mixture was added ice water was added, and the mixture was separated. Then, the organic layer was washed twice with a 5% aqueous solution of sodium bicarbonate, then dried and concentrated to obtain 4.98 g (18.1 mmol) of 1-(2-methyl-5-phenyl)phenylbromoethane.

$^1$H-NMR(CDCl$_3$, TMS)

δ (ppm): 7.20–7.80 (8H, m), 5.48 (1H, q), 2.48 (3H, s), 2.14 (3H, d)

(3) To a mixture of 0.99 g (8.63 mol) of 5-methoxy-2,4-dihydro-3H-1,2,4-triazol-3-one and 22 ml of dry acetonitrile was added 0.99 g (7.20 mol) of potassium carbonate and the mixture was stirred for 10 minutes. To the suspension was added 1.98 g (7.19 mol) of 1-(2-methyl-5-phenyl)phenylbromoethane, and the mixture was stirred at 50° C. for 7 hours. After the reaction mixture was allowed to cool to room temperature, 200 ml of water was added, and the mixture was extracted 3 times with 70 ml of t-butyl methyl ether. The organic layer was washed with water, dried and concentrated. The residue was subjected to silica gel column chromatography (eluted with n-hexane:ethyl acetate=2:1and then 1:1) to obtain 0.36 g (1.17 mmol) of the crystalline compound, 5-methoxy-4-{1-(2-methyl-5-phenyl)phenylethyl}-2,4-dihydro-3H-1,2,4-triazol-3-one.

$^1$H-NMR(CDCl$_3$, TMS)

δ (ppm): 9.15 (1H, br), 7.10–7.90 (8H, m), 5.54 (1H, q), 3.88 (3H, s), 2.40 (3H, s), 1.83 (3H, d)

PRODUCTION EXAMPLE 57

To a solution of 0.29 g (0.96 mmol) of 5-cyclopropyl-4-(2-methyl-5-phenylbenzyl)-2,4-dihydro-3H-1,2,4-triazol-3-one (produced in the following Reference Production Example 18) and 0.15 g (1.05 mmol) of methyl iodide in 10 ml of dry N,N-dimethylformamide was added 0.06 g (1.43 mmol) of sodium hydride (60% oil dispersion) with ice-cooling. After vigorous bubbling ceased, the mixture was removed from an ice bath and stirred at room temperature for 1 hour. After the mixture was cooled again, 70 ml of 5% aqueous hydrochloric acid was added thereto, and the mixture was extracted with tert-butyl methyl ether. The organic layer was washed successively with water, a 5% aqueous solution of sodium bicarbonate, and saturated brine, then dried and concentrated. The residue was subjected to silica gel preparative thin layer chromatography (developed with n-hexane:ethyl acetate=1:2) to obtain 0.25 g (0.78 mmol) of 5-cyclopropyl-2-methyl-4-(2-methyl-5-phenylbenzyl)-2,4-dihydro-3H-1,2,4-triazol-3-one (the compound 538 of the present invention) having a melting point of 102.4° C.

$^1$H-NMR(CDCl$_3$, TMS)

δ (ppm): 7.15–7.55 (8H, m), 4.98 (2H, s), 3.45 (3H, s), 2.40 (3H, s), 1.42 (1H, m), 0.75–0.9 (4H, m)

Reference Production Example 18

(1) To a suspension of 3.11 g (12.7 mmol) of crude 2-methyl-5-phenylbenzylisocyanate in 24 ml of toluene was added 1.27 g (12.7 mmol) of cyclopropylcarbonylhydrazide, and the mixture was stirred at 60° C. for 1.5 hours. After allowing to cool to room temperature, the reaction solution was concentrated, and the residue was recrystallized from ethanol to obtain 1.86 g (5.75 mmol) of 1-cycloprpylcarbonyl-4-(2-methyl-5-phenylbenzyl) semicarbazide having a melting point of 147.0° C.

$^1$H-NMR(CDCl$_3$, TMS)

δ (ppm): 9.21 (1H, br), 8.03 (1H, br), 7.05–7.60 (8H, m), 6.16 (1H, br), 4.24 (2H, d), 2.19 (3H, s), 1.14 (1H, s), 0.73 (2H, br), 0.57 (2H, m)

(2) To 20 ml of a 2% aqueous solution of potassium hydroxide was added 1.67 g (5.16 mmol) of 1-cycropropylcarbonyl-4-(2-methyl-5-phenylbenzyl) semicarbazide and the mixture was stirred at 90° C. for 7 hours. After allowing to cool to room temperature, the reaction solution was extracted with ethyl acetate, and the organic layer was washed with water, dried and concentrated. The residue was subjected to silica gel column chromatography (eluted with n-hexane:ethyl acetate=1:1) to obtain 0.64 g (2.09 mmol) of 5-cyclopropyl-4-(2-methyl-5-phenylbenzyl)-2,4-dihydro-3H-1,2,4-trizol-3-one.

$^1$H-NMR(CDCl$_3$, TMS)

δ (ppm): 9.20 (1H, br), 7.15–7.55 (8H, m), 4.98 (2H, s), 2.40 (3H, s), 1.42 (1H, m), 0.86 (2H, m), 0.78 (2H, m)

Examples of the production of the alkoxytriazolone compound represented by the formula [II-1] are set forth below.

Intermediate Production Example 1

To a solution of 19.3 g (420 mmol) of methylhydrazine in tetrahydrofuran (80 ml) was added dropwise 20.0 ml (210 mml) of ethyl chlorocarbonate over 40 minutes with ice-cooling under an atmosphere of nitrogen. After the mixture was stirred at room temperature for 2 hours, impurities were removed by filtration, and the filtrate was concentrated under reduced pressure to obtain 21.7 g of a crude product of N-ethoxycarbonyl-N-methylhydrazine as a colorless oil.

$^1$H-NMR(CDCl$_3$, TMS)

δ (ppm): 1.28 (3H, t, J=7.5 Hz), 3.11 (3H, s), 4.1 (2H, br), 4.17 (2H, q, J=7.5 Hz)

To a solution of 9.49 g (90 mmol) of cyanogen bromide in methanol (6 ml) was added dropwise 18.4 ml (90 mmol) of sodium methoxide (28% methanol solution) with ice-cooling under an atmosphere of nitrogen and the mixture was stirred overnight. After the reaction mixture was neutralized with concentrated hydrochloric acid, impurities were removed by filtration, and the filtrate was cooled. Then, a solution of 10.6 g of a crude product of N-ethoxycarbonyl-N-methylhydrazine in methanol (8 ml) was added thereto. Further, 1.2 ml of concentrated hydrochloric acid was added thereto, and the mixture was stirred at room temperature for 21 hours. Then, 18.4 ml (90 mmol) of sodium methoxide (28% methanol solution) was added thereto, and the mixture was stirred at 60° C. for 10 hours. Then, the reaction mixture was concentrated under reduced pressure, and water was added to the residue. The mixture was acidified with concentrated hydrochloric acid and extracted with ethyl acetate. The organic layer was washed with water, dried and concentrated. The residue (colorless powder) was washed with tert-butyl methyl ether to obtain 1.24 g (9.6 mmol) of 5-methoxy-2-methyl-2,4-dihydro-3H-1,2,4-triazol-3-one.

$^1$H-NMR(DMSO-D6)

δ (ppm): 3.17 (3H, s), 3.82 (3H, s), 11.38 (1H, br-s)

The following will describe a production example of a boron compound represented by a general formula [III-1].

Intermediate Production Example 2

A mixture of 3 g (10.4 mmol) of 4-(5-bromo-2-methylbenzyl)-5-methoxy-2-methyl-2,4-dihydro-3H-1,2,4-triazol-3-one (the compound 299 of the present invention, produced in Production Example 20), 3.16 g (12.4 mmol) of bis(pinacolate)diborone, 0.42 g (0.51 mmol) of {1,1'-bis(diphenylphosphino)ferrocene}dichloropalladium (II) methylene chloride complex, 3.05 g (31.1 mmol) of potassium acetate and dimethylsulfoxide (75 ml) was stirred at 80° C. for 8 hours. After the mixture was cooled to room temperature, ethyl acetate and Celite were added thereto, and the resultant mixture was filtered. The filtrate was successively washed with water and saturated brine, then dried and concentrated. The residue was subjected to neutral alumina column chromatography (eluted with a mixed solvent of hexane: and ethyl acetate) to obtain 1.76 g of 5-methoxy-2-methyl-4-{2-methyl-5-(4,4,5,5-tetramethyl-1,3,2-dioxoboronyl)}benzyl-2,4-dihydro-3H-1,2,4-triazol-3-one.

$^1$H-NMR(CDCl$_3$, TMS)

δ (ppm): 7.61~7.64 (2H, m) , 7.16 (1H, d, J=7.5 Hz), 4.72 (2H, s), 3.90 (3H, s), 3.39 (3H, s), 2.41 (3H, s), 1.32 (12H, s)

Examples of the compounds of the present invention with compound numbers are shown in Tables 1 to 23.

The compound represented by the formula:

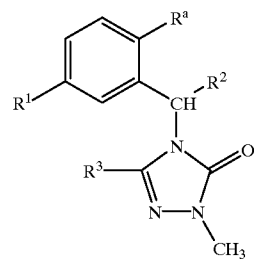

TABLE 1

| Number | R$^1$ | R$^a$ | R$^3$ | R$^2$ |
|---|---|---|---|---|
| 1 | Ph | H | MeO | H |
| 2 | Ph | H | Cl | H |
| 3 | Ph | H | MeS | H |
| 4 | Ph | H | cyano | H |
| 5 | Ph | H | Me | H |
| 6 | Ph | Me | MeO | H |
| 7 | Ph | Me | Cl | H |
| 8 | Ph | Me | MeS | H |
| 9 | Ph | Me | cyano | H |
| 10 | Ph | Me | Me | H |
| 11 | Ph | H | MeO | Me |
| 12 | Ph | H | Cl | Me |
| 13 | Ph | H | MeS | Me |
| 14 | Ph | H | cyano | Me |
| 15 | Ph | H | Me | Me |
| 16 | 2-Me-Ph | H | MeO | H |
| 17 | 3,4-Me$_2$-Ph | H | MeO | H |
| 18 | 2,4-Me$_2$-Ph | H | MeO | H |
| 19 | 4-Cl-Ph | Cl | MeO | H |
| 20 | 3,4-Cl$_2$-Ph | H | MeO | H |
| 21 | 4-Cl-Ph | H | MeO | H |
| 22 | 3-Cl-Ph | H | MeO | H |
| 23 | 2-Cl-Ph | H | MeO | H |
| 24 | 4-Me-Ph | H | MeO | H |
| 25 | 3-Me-Ph | H | MeO | H |

TABLE 2

| Number | R$^1$ | R$^a$ | R$^3$ | R$^2$ |
|---|---|---|---|---|
| 26 | 3,4-Cl$_2$-Ph | H | MeO | Me |
| 27 | 3,4-Cl$_2$-Ph | H | Cl | Me |
| 28 | 3-F-Ph | Me | MeO | H |
| 29 | 4-Cl-Ph | H | Cl | Me |
| 30 | 4-Cl-Ph | H | MeO | Me |
| 31 | 4-Cl-Ph | Me | MeS | H |
| 32 | 3,4-Me$_2$-Ph | Me | Cl | H |
| 33 | 2,4-Me$_2$-Ph | Me | Cl | H |
| 34 | 4-Cl-Ph | Me | cyano | H |
| 35 | 3,4-Cl$_2$-Ph | Me | Cl | H |
| 36 | 4-Cl-Ph | Me | Cl | H |
| 37 | 3-Cl-Ph | Me | Cl | H |
| 38 | 4-Cl-Ph | Me | Me | H |
| 39 | 4-Me-Ph | Me | Cl | H |
| 40 | 3-Me-Ph | Me | Cl | H |
| 41 | 2-Me-Ph | Me | MeO | H |
| 42 | 3,4-Me$_2$-Ph | Me | MeO | H |
| 43 | 2,4-Me$_2$-Ph | Me | MeO | H |
| 44 | 3-MeO-Ph | Me | MeO | H |
| 45 | 3,4-Cl$_2$-Ph | Me | MeO | H |
| 46 | 4-Cl-Ph | Me | MeO | H |
| 47 | 3-Cl-Ph | Me | MeO | H |
| 48 | 2-Cl-Ph | Me | MeO | H |
| 49 | 4-Me-Ph | Me | MeO | H |
| 50 | 3-Me-Ph | Me | MeO | H |

TABLE 3

| Number | R$^1$ | R$^a$ | R$^3$ | R$^2$ |
|---|---|---|---|---|
| 51 | Me | H | MeO | H |
| 52 | Me | H | Cl | H |
| 53 | Me | Me | MeO | H |
| 54 | Me | Me | Cl | H |
| 55 | HC(=O) | H | MeO | H |
| 56 | HC(=O) | H | MeO | Me |
| 57 | n-Hex | H | MeO | H |
| 58 | cyano | H | MeO | Me |
| 59 | cyano | H | MeO | H |
| 60 | cyano | Me | MeO | H |
| 61 | ClCH$_2$ | H | MeO | H |
| 62 | BrCH$_2$ | H | MeO | H |
| 63 | t-Bu | H | MeO | H |
| 64 | Me | H | MeO | Me |
| 65 | t-Bu | H | MeO | Me |
| 66 | t-Bu | Me | MeO | H |
| 67 | ClCH$_2$ | Me | MeO | H |
| 68 | BrCH$_2$ | Me | MeO | H |
| 69 | ClCH$_2$ | H | MeO | Me |
| 70 | BrCH$_2$ | H | MeO | Me |
| 71 | n-Bu | Me | MeO | H |
| 72 | MeC(=O) | H | MeO | H |
| 73 | MeC(=O) | Me | MeO | H |
| 74 | MeC(=O) | H | MeO | Me |
| 75 | HC(=O) | Me | MeO | H |

TABLE 4

| Number | R$^1$ | R$^a$ | R$^3$ | R$^2$ |
|---|---|---|---|---|
| 76 | H$_2$C=CH | H | MeO | H |
| 77 | c-Hex | H | MeO | H |
| 78 | c-Hex | Me | MeO | H |
| 79 | n-PrCH=CH | H | MeO | H |
| 80 | n-PrCH=CH | Me | MeO | H |
| 81 | n-PentCH=CH | Me | MeO | H |
| 82 | n-HexCH=CH | Me | MeO | H |
| 83 | PhCH$_2$CH$_2$CH=C(Me) | H | MeO | H |
| 84 | PhCH$_2$CH$_2$CH=C(Me) | Me | MeO | H |
| 85 | Me$_2$C=CH | Me | MeO | H |
| 86 | Me$_2$C=C(Me) | Me | MeO | H |
| 87 | MeCH=C(Me) | Me | MeO | H |
| 88 | Me-OC(=O) | H | MeO | H |
| 89 | Me-OC(=O) | Me | MeO | H |
| 90 | Me-OC(=O) | H | MeO | Me |
| 91 | PhCH$_2$CH=CH | H | MeO | H |
| 92 | PhCH$_2$CH=C(Me) | H | MeO | H |
| 93 | PhCH$_2$CH=C(Me) | Me | MeO | H |
| 94 | Cl | H | Cl | H |
| 95 | Br | H | Cl | H |
| 96 | NO$_2$ | Me | MeO | H |
| 97 | NO$_2$ | H | MeO | Me |
| 98 | NO$_2$ | H | MeO | H |
| 99 | I | H | Cl | H |
| 100 | Cl | Me | Cl | H |

TABLE 5

| Number | R$^1$ | R$^a$ | R$^3$ | R$^2$ |
|---|---|---|---|---|
| 101 | Bn | Me | MeO | H |
| 102 | PhCH$_2$CH$_2$ | Me | MeO | H |
| 103 | PhCH=CH | Me | MeO | H |
| 104 | PhSCH$_2$ | Me | MeO | H |
| 105 | Cl | Me | Cl | H |
| 106 | Br | Me | Cl | H |
| 107 | I | Me | Cl | H |
| 108 | PhC(Me)=NOCH$_2$ | Me | MeO | H |
| 109 | 3-CF$_3$-PhC(Me)=NOCH$_2$ | Me | MeO | H |
| 110 | PhC(=O)OCH$_2$ | Me | MeO | H |
| 111 | 2-Me-PhOCH$_2$ | Me | MeO | H |
| 112 | Cl | H | Cl | Me |
| 113 | Br | H | Cl | Me |
| 114 | I | H | Cl | Me |
| 115 | NH$_2$ | H | MeO | H |
| 116 | MeOC(=O)C(Me)=CH | Me | MeO | H |
| 117 | MeOC(=O)CH=C(Me) | Me | MeO | H |
| 118 | MeOC(=O)C(Me)=C(Me) | Me | MeO | H |
| 119 | NH$_2$ | H | MeO | Me |
| 120 | 2-Cl-PhOCH$_2$ | Me | MeO | H |
| 121 | NH$_2$ | Me | MeO | H |
| 122 | 2,4-Cl$_2$-PhOCH$_2$ | Me | MeO | H |
| 123 | 2,5-Me$_2$-PhOCH$_2$ | Me | MeO | H |
| 124 | 2,5-Me$_2$-BnO | Me | MeO | H |
| 125 | 4-Cl-PhC(Me)=NOCH$_2$ | Me | MeO | H |

TABLE 6

| Number | R$^1$ | R$^a$ | R$^3$ | R$^2$ |
|---|---|---|---|---|
| 126 | 2-Cl-PhC(Me)=NOCH$_2$ | Me | MeO | H |
| 127 | 2,4-Cl$_2$-PhC(Me)=NOCH$_2$ | Me | MeO | H |
| 128 | OH | H | MeO | H |
| 129 | OH | Me | MeO | H |
| 130 | OH | H | MeO | Me |
| 131 | MeOC(=O)C(CO$_2$Me)=C(Me) | Me | MeO | H |
| 132 | MeOC(=O)C(CN)=C(Me) | Me | MeO | H |
| 133 | 2,4-Me$_2$-PhC(Me)=NOCH$_2$ | Me | MeO | H |
| 134 | MeOCH$_2$CH=C(Me) | Me | MeO | H |
| 135 | EtOCH$_2$CH=C(Me) | Me | MeO | H |
| 136 | PhCH=C(Me) | Me | MeO | H |
| 137 | BnOCH=C(Me) | Me | MeO | H |
| 138 | 4-Me-BnOCH=C(Me) | Me | MeO | H |
| 139 | 3-Me-BnOCH=C(Me) | Me | MeO | H |
| 140 | 2-Me-BnOCH=C(Me) | Me | MeO | H |
| 141 | 3,4-Me$_2$-BnOCH=C(Me) | Me | MeO | H |
| 142 | PhOCH$_2$CH=C(Me) | Me | MeO | H |
| 143 | 2-Me-PhC(Me)=NOCH$_2$ | Me | MeO | H |
| 144 | 4-Me-PhC(Me)=NOCH$_2$ | Me | MeO | H |
| 145 | 2-Me-BnO | Me | MeO | H |
| 146 | 2-Cl-BnO | Me | MeO | H |
| 147 | 4-Cl-BnO | Me | MeO | H |
| 148 | 4-Cl-PhOCH$_2$ | Me | MeO | H |
| 149 | 2-Cl,4-Me-PhOCH$_2$ | Me | MeO | H |
| 150 | 2-Me-PhOCH$_2$ | Me | MeO | H |

TABLE 7

| Number | R$^1$ | R$^a$ | R$^3$ | R$^2$ |
|---|---|---|---|---|
| 151 | 6-Me-Py-2-yl | Me | MeO | H |
| 152 | Py-2-yl | Me | MeO | H |
| 153 | Py-3-yl | Me | MeO | H |
| 154 | Py-4-yl | Me | MeO | H |
| 155 | 6-Cl-Py-2-yl | Me | MeO | H |
| 156 | 3-Cl-Py-2-yl | Me | MeO | H |
| 157 | 3-MeO-Py-2-yl | Me | MeO | H |
| 158 | 2-thienyl | Me | MeO | H |
| 159 | 3-thienyl | Me | MeO | H |
| 160 | 2-furyl | Me | MeO | H |
| 161 | 3-furyl | Me | MeO | H |
| 162 | 2-benzothienyl | Me | MeO | H |
| 163 | 3-benzothienyl | Me | MeO | H |
| 164 | 5-MeO-Py-2-yl | Me | MeO | H |
| 165 | pyrrol-1-yl | Me | MeO | H |
| 166 | 2-pyrimidinyl | Me | MeO | H |
| 167 | 4-pyrimidinyl | Me | MeO | H |
| 168 | 1-pyrazolyl | Me | MeO | H |
| 169 | 5-thiazolyl | Me | MeO | H |
| 170 | 5-oxazolyl | Me | MeO | H |
| 171 | benzothiazol-2-ylthio | Me | MeO | H |
| 172 | 2-quinolinyl | Me | MeO | H |
| 173 | 4-Me-oxazol-2-yl | Me | MeO | H |

TABLE 7-continued

| Number | R$^1$ | R$^a$ | R$^3$ | R$^2$ |
|---|---|---|---|---|
| 174 | 3-Me-Py-2-yl | Me | MeO | H |
| 175 | 3-Cl-5-CF$_3$-Py-2-yl | Me | MeO | h |

TABLE 8

| Number | R$^1$ | R$^a$ | R$^3$ | R$^2$ |
|---|---|---|---|---|
| 176 | PhO | H | MeO | H |
| 177 | 4-Me-PhO | Me | MeO | H |
| 178 | 3-Me-PhO | Me | MeO | H |
| 179 | 2-Me-PhO | Me | MeO | H |
| 180 | 3,4-Me$_2$-PhO | Me | MeO | H |
| 181 | PhO | Me | MeO | H |
| 182 | 4-Cl-PhO | Me | MeO | H |
| 183 | Py-2-yloxy | Me | MeO | H |
| 184 | 5-CF$_3$-Py-2-yloxy | Me | MeO | H |
| 185 | 3-Cl-5-CF$_3$-Py-2-yloxy | Me | MeO | H |
| 186 | 5-CF$_3$-Py-2-yloxy | H | MeO | H |
| 187 | pyrimidin-4-yloxy | Me | MeO | H |
| 188 | 6-Cl-pyrimidin-4-yloxy | Me | MeO | H |
| 189 | 3-Cl-5-CF$_3$-Py-2-yloxy | H | MeO | H |
| 190 | pyrimidin-2-yloxy | Me | MeO | H |
| 191 | PhO | H | MeO | Me |
| 192 | 5-Cl-Py-2-yloxy | Me | MeO | H |
| 193 | BnO | H | MeO | H |
| 194 | BnO | Me | MeO | H |
| 195 | BnO | H | MeO | Me |
| 196 | allyloxy | Me | MeO | H |
| 197 | propargyloxy | Me | MeO | H |
| 198 | cyclopropylmethyloxy | Me | MeO | H |
| 199 | i-PrO | Me | MeO | H |
| 200 | t-BuO | Me | MeO | H |

TABLE 9

| Number | R$^1$ | R$^a$ | R$^3$ | R$^2$ |
|---|---|---|---|---|
| 201 | BnN(Me) | Me | MeO | H |
| 202 | 5-CF$_3$-Py-2-ylamino | Me | MeO | H |
| 203 | 3-Cl-5-CF$_3$-Py-2-ylamino | Me | MeO | H |
| 204 | PhS | Me | MeO | H |
| 205 | 4-Me-PhS | Me | MeO | H |
| 206 | 3-Me-PhS | Me | MeO | H |
| 207 | 2-Me-PhS | Me | MeO | H |
| 208 | 3,4-Me$_2$-PhS | Me | MeO | H |
| 209 | BnS | Me | MeO | H |
| 210 | 4-Me-BnS | Me | MeO | H |
| 211 | 3-Me-BnS | Me | MeO | H |
| 212 | 2-Me-BnS | Me | MeO | H |
| 213 | 3,4-Me$_2$-BnS | Me | MeO | H |
| 214 | Py-2-ylthio | Me | MeO | H |
| 215 | 5-CF$_3$-Py-2-ylthio | Me | MeO | H |
| 216 | 3-Cl-5-CF$_3$-Py-2-ylthio | Me | MeO | H |
| 217 | pyrimidine-4-ylthio | Me | MeO | H |
| 218 | pyrimidine-2-ylthio | Me | MeO | H |
| 219 | N-(5-CF$_3$-Py-2-yl)-N(Me) | Me | MeO | H |
| 220 | N-(3-Cl-5-CF$_3$-Py-2-yl)-N(Me) | Me | MeO | H |
| 221 | n-PrS | Me | MeO | H |
| 222 | t-BuS | Me | MeO | H |
| 223 | 5-MeO-Py-2-ylthio | Me | MeO | H |
| 224 | cyclopropylmethylthio | Me | MeO | H |
| 225 | propargylthio | Me | MeO | H |

TABLE 10

| Number | R$^1$ | R$^a$ | R$^3$ | R$^2$ |
|---|---|---|---|---|
| 226 | MeON=C(Me) | H | MeO | H |
| 227 | EtON=C(Me) | H | MeO | H |
| 228 | n-PrON=C(Me) | H | MeO | H |
| 229 | i-PrON=C(Me) | H | MeO | H |
| 230 | n-BuON=C(Me) | H | MeO | H |
| 231 | i-BuON=C(Me) | H | MeO | H |
| 232 | sec-BuON=C(Me) | H | MeO | H |
| 233 | n-Pent-ON=C(Me) | H | MeO | H |
| 234 | n-Hex-ON=C(Me) | H | MeO | H |
| 235 | t-Bu-ON=C(Me) | H | MeO | H |
| 236 | c-PrCH$_2$ON=C(Me) | H | MeO | H |
| 237 | c-PentCH$_2$ON=C(Me) | H | MeO | H |
| 238 | t-BuCH$_2$ON=C(Me) | H | MeO | H |
| 239 | BnON=C(Me) | H | MeO | H |
| 240 | 4-Me-BnON=C(Me) | H | MeO | H |
| 241 | 3-Me-BnON=C(Me) | H | MeO | H |
| 242 | 2-Me-BnON=C(Me) | H | MeO | H |
| 243 | 3,4-Me$_2$-BnON=C(Me) | H | MeO | H |
| 244 | 2,5-Me$_2$-BnON=C(Me) | H | MeO | H |
| 245 | 4-Cl-BnON=C(Me) | H | MeO | H |
| 246 | 3-Cl-BnON=C(Me) | H | MeO | H |
| 247 | 2-Cl-BnON=C(Me) | H | MeO | H |
| 248 | 3,4-Cl$_2$-BnON=C(Me) | H | MeO | H |
| 249 | BnON=C(Me) | H | Cl | H |
| 250 | BnON=C(Me) | H | MeS | H |

TABLE 11

| Number | R$^1$ | R$^a$ | R$^3$ | R$^2$ |
|---|---|---|---|---|
| 251 | MeOCH$_2$CH$_2$ON=C(Me) | H | MeO | H |
| 252 | EtOCH$_2$CH$_2$ON=C(Me) | H | MeO | H |
| 253 | PhCH$_2$CH$_2$ON=C(Me) | H | MeO | H |
| 254 | PhON=C(Me) | H | MeO | H |
| 255 | 2,4-Cl$_2$-BnON=C(Me) | H | MeO | H |
| 256 | PhOCH$_2$CH$_2$ON=C(Me) | H | MeO | H |
| 257 | PhO(CH$_2$)$_3$ON=C(Me) | H | MeO | H |
| 258 | 4-Me-Ph(CH$_2$)$_2$ON=C(Me) | H | MeO | H |
| 259 | 2-Me-Ph(CH$_2$)$_2$ON=C(Me) | H | MeO | H |
| 260 | 2,4-Me$_2$-BnON=C(Me) | H | MeO | H |
| 261 | PhO(CH$_2$)$_4$ON=C(Me) | H | MeO | H |
| 262 | 4-Me-PhO(CH$_2$)$_2$ON=C(Me) | H | MeO | H |
| 263 | 2-Me-PhO(CH$_2$)$_2$ON=C(Me) | H | MeO | H |
| 264 | 4-Cl-PhCH(Me)ON=C(Me) | H | MeO | H |
| 265 | 2-Cl-PhCH(Me)ON=C(Me) | H | MeO | H |
| 266 | PhCH(Me)ON=C(Me) | H | MeO | H |
| 267 | 4-Me-PhCH(Me)ON=C(Me) | H | MeO | H |
| 268 | 2-Me-PhCH(Me)ON=C(Me) | H | MeO | H |
| 269 | 4-t-Bu-BnON=C(Me) | H | MeO | H |
| 270 | BnON=C(CN) | H | MeO | H |
| 271 | MeON=C(Me)CH$_2$ON=C(Me) | H | MeO | H |
| 272 | PhON=C(Me)CH$_2$ON=C(Me) | H | MeO | H |
| 273 | PhCH(CN)ON=C(Me) | H | MeO | H |
| 274 | BnON=C(Me) | H | Cyano | H |
| 275 | BnON=C(Me) | H | Me | H |

TABLE 12

| Number | R$^1$ | R$^a$ | R$^3$ | R$^2$ |
|---|---|---|---|---|
| 276 | BnON=C(Me) | Me | MeS | H |
| 277 | BnON=C(Me) | Me | Cyano | H |
| 278 | Cl | H | MeO | Me |
| 279 | Br | H | MeO | Me |
| 280 | I | H | MeO | Me |
| 281 | PhOCH$_2$ | H | MeO | H |
| 282 | Ph-C(=O)—O | H | MeO | H |
| 283 | PhOCH$_2$ | Me | MeO | H |
| 284 | Ph-C(=O)—O | Me | MeO | H |
| 285 | Ph-OCH$_2$C(=O)—O | Me | MeO | H |
| 286 | HON=C(Me) | H | MeO | H |
| 287 | HON=C(Me) | Me | MeO | H |
| 288 | HON=C(Me) | H | MeO | Me |
| 289 | BnON=C(Me) | Me | Me | H |
| 290 | BnON=CH | Me | MeO | H |

TABLE 12-continued

| Number | R¹ | Rᵃ | R³ | R² |
|---|---|---|---|---|
| 291 | 5-CF₃-Py-2-yl-ON=C(Me) | Me | MeO | H |
| 292 | 3-Cl-5-CF₃-Py-2-yl-ON=C(Me) | Me | MeO | H |
| 293 | 5-CF₃-Py-2-yl-ON=C(Me) | H | MeO | H |
| 294 | 3-Cl-5-CF₃-Py-2-yl-ON=C(Me) | H | MeO | H |
| 295 | Cl | H | MeO | H |
| 296 | Br | H | MeO | H |
| 297 | I | H | MeO | H |
| 298 | Cl | Me | MeO | H |
| 299 | Br | Me | MeO | H |
| 300 | I | Me | MeO | H |

TABLE 13

| Number | R¹ | Rᵃ | R³ | R² |
|---|---|---|---|---|
| 301 | MeON=C(Me) | Me | MeO | H |
| 302 | EtON=C(Me) | Me | MeO | H |
| 303 | n-PrON=C(Me) | Me | MeO | H |
| 304 | i-PrON=C(Me) | Me | MeO | H |
| 305 | n-BuON=C(Me) | Me | MeO | H |
| 306 | i-BuON=C(Me) | Me | MeO | H |
| 307 | sec-BuON=C(Me) | Me | MeO | H |
| 308 | n-Pent-ON=C(Me) | Me | MeO | H |
| 309 | n-Hex-ON=C(Me) | Me | MeO | H |
| 310 | t-Bu-ON=C(Me) | Me | MeO | H |
| 311 | c-PrCH₂ON=C(Me) | Me | MeO | H |
| 312 | c-PentCH₂ON=C(Me) | Me | MeO | H |
| 313 | t-BuCH₂ON=C(Me) | Me | MeO | H |
| 314 | BnON=C(Me) | Me | MeO | H |
| 315 | 4-Me-BnON=C(Me) | Me | MeO | H |
| 316 | 3-Me-BnON=C(Me) | Me | MeO | H |
| 317 | 2-Me-BnON=C(Me) | Me | MeO | H |
| 318 | 3,4-Me₂-BnON=C(Me) | Me | MeO | H |
| 319 | 2,5-Me₂-BnON=C(Me) | Me | MeO | H |
| 320 | 4-Cl-BnON=C(Me) | Me | MeO | H |
| 321 | 3-Cl-BnON=C(Me) | Me | MeO | H |
| 322 | 2-Cl-BnON=C(Me) | Me | MeO | H |
| 323 | 3,4-Cl₂-BnON=C(Me) | Me | MeO | H |
| 324 | HC≡CCH₂ON=C(Me) | Me | MeO | H |
| 325 | H₂C=CHCH₂ON=C(Me) | Me | MeO | H |

TABLE 14

| Number | R¹ | Rᵃ | R³ | R² |
|---|---|---|---|---|
| 326 | MeOCH₂CH₂ON=C(Me) | Me | MeO | H |
| 327 | EtOCH₂CH₂ON=C(Me) | Me | MeO | H |
| 328 | PhCH₂CH₂ON=C(Me) | Me | MeO | H |
| 329 | PhON=C(Me) | Me | MeO | H |
| 330 | 2,4-Cl₂-BnON=C(Me) | Me | MeO | H |
| 331 | PhOCH₂CH₂ON=C(Me) | Me | MeO | H |
| 332 | PhO(CH₂)₃ON=C(Me) | Me | MeO | H |
| 333 | 4-Me-Ph(CH₂)₂ON=C(Me) | Me | MeO | H |
| 334 | 2-Me-Ph(CH₂)₂ON=C(Me) | Me | MeO | H |
| 335 | 2,4-Me₂-BnON=C(Me) | Me | MeO | H |
| 336 | PhO(CH₂)₄ON=C(Me) | Me | MeO | H |
| 337 | 4-Me-PhO(CH₂)₂ON=C(Me) | Me | MeO | H |
| 338 | 2-Me-PhO(CH₂)₂ON=C(Me) | Me | MeO | H |
| 339 | 4-Cl-PhCH(Me)ON=C(Me) | Me | MeO | H |
| 340 | 2-Cl-PhCH(Me)ON=C(Me) | Me | MeO | H |
| 341 | PhCH(Me)ON=C(Me) | Me | MeO | H |
| 342 | 4-Me-PhCH(Me)ON=C(Me) | Me | MeO | H |
| 343 | 2-Me-PhCH(Me)ON=C(Me) | Me | MeO | H |
| 344 | 4-t-Bu-BnON=C(Me) | Me | MeO | H |
| 345 | BnON=C(CN) | Me | MeO | H |
| 346 | MeON=C(Me)CH₂ON=C(Me) | Me | MeO | H |
| 347 | PhON=C(Me)CH₂ON=C(Me) | Me | MeO | H |
| 348 | PhCH(CN)ON=C(Me) | Me | MeO | H |
| 349 | BnON=C(Me) | Me | Cl | H |
| 350 | PhCH(MeO)ON=C(Me) | Me | MeO | H |

TABLE 15

| Number | R¹ | Rᵃ | R³ | R² |
|---|---|---|---|---|
| 351 | MeON=C(Me) | H | MeO | Me |
| 352 | EtON=C(Me) | H | MeO | Me |
| 353 | n-PrON=C(Me) | H | MeO | Me |
| 354 | i-PrON=C(Me) | H | MeO | Me |
| 355 | n-BuON=C(Me) | H | MeO | Me |
| 356 | i-BuON=C(Me) | H | MeO | Me |
| 357 | sec-BuON=C(Me) | H | MeO | Me |
| 358 | n-Pent-ON=C(Me) | H | MeO | Me |
| 359 | n-Hex-ON=C(Me) | H | MeO | Me |
| 360 | t-Bu-ON=C(Me) | H | MeO | Me |
| 361 | c-PrCH₂ON=C(Me) | H | MeO | Me |
| 362 | c-PentCH₂ON=C(Me) | H | MeO | Me |
| 363 | t-BuCH₂ON=C(Me) | H | MeO | Me |
| 364 | BnON=C(Me) | H | MeO | Me |
| 365 | 4-Me-BnON=C(Me) | H | MeO | Me |
| 366 | 3-Me-BnON=C(Me) | H | MeO | Me |
| 367 | 2-Me-BnON=C(Me) | H | MeO | Me |
| 368 | 3,4-Me₂-BnON=C(Me) | H | MeO | Me |
| 369 | 2,5-Me₂-BnON=C(Me) | H | MeO | Me |
| 370 | 4-Cl-BnON=C(Me) | H | MeO | Me |
| 371 | 3-Cl-BnON=C(Me) | H | MeO | Me |
| 372 | 2-Cl-BnON=C(Me) | H | MeO | Me |
| 373 | 3,4-Cl₂-BnON=C(Me) | H | MeO | Me |
| 374 | BnON=C(Me) | H | Cl | Me |
| 375 | BnON=C(Me) | H | MeS | Me |

TABLE 16

| Number | R¹ | Rᵃ | R³ | R² |
|---|---|---|---|---|
| 376 | MeOCH₂CH₂ON=C(Me) | H | MeO | Me |
| 377 | EtOCH₂CH₂ON=C(Me) | H | MeO | Me |
| 378 | PhCH₂CH₂ON=C(Me) | H | MeO | Me |
| 379 | PhON=C(Me) | H | MeO | Me |
| 380 | 2,4-Cl₂-BnON=C(Me) | H | MeO | Me |
| 381 | PhOCH₂CH₂ON=C(Me) | H | MeO | Me |
| 382 | PhO(CH₂)₃ON=C(Me) | H | MeO | Me |
| 383 | 4-Me-Ph(CH₂)₂ON=C(Me) | H | MeO | Me |
| 384 | 2-Me-Ph(CH₂)₂ON=C(Me) | H | MeO | Me |
| 385 | 2,4-Me₂-BnON=C(Me) | H | MeO | Me |
| 386 | PhO(CH₂)₄ON=C(Me) | H | MeO | Me |
| 387 | 4-Me-PhO(CH₂)₂ON=C(Me) | H | MeO | Me |
| 388 | 2-Me-PhO(CH₂)₂ON=C(Me) | H | MeO | Me |
| 389 | 4-Cl-PhCH(Me)ON=C(Me) | H | MeO | Me |
| 390 | 2-Cl-PhCH(Me)ON=C(Me) | H | MeO | Me |
| 391 | PhCH(Me)ON=C(Me) | H | MeO | Me |
| 392 | 4-Me-PhCH(Me)ON=C(Me) | H | MeO | Me |
| 393 | 2-Me-PhCH(Me)ON=C(Me) | H | MeO | Me |
| 394 | 4-t-Bu-BnON=C(Me) | H | MeO | Me |
| 395 | BnON=C(CN) | H | MeO | Me |
| 396 | MeON=C(Me)CH₂ON=C(Me) | H | MeO | Me |
| 397 | PhON=C(Me)CH₂ON=C(Me) | H | MeO | Me |
| 398 | PhCH(CN)ON=C(Me) | H | MeO | Me |
| 399 | BnON=C(Me) | H | Cyano | Me |
| 400 | BnON=C(Me) | H | Me | Me |

TABLE 17

| Number | R¹ | Rᵃ | R³ | R² |
|---|---|---|---|---|
| 401 | MeSC(Me)=N | Me | MeO | H |
| 402 | MeC(=S)—NH | Me | MeO | H |
| 403 | c-PrC(=S)—NH | Me | MeO | H |
| 404 | n-BuSC(Me)=N | Me | MeO | H |
| 405 | MeSC(Et)=N | Me | MeO | H |
| 406 | MeSC(n-Pr)=N | Me | MeO | H |
| 407 | 4-Me-BnSC(c-Pr)=N | Me | MeO | H |
| 408 | MeSC(c-Pr)=N | Me | MeO | H |
| 409 | MeSC(c-Pent)=N | Me | MeO | H |
| 410 | MeSC(c-Hex)=N | Me | MeO | H |
| 411 | BnSC(Me)=N | Me | MeO | H |
| 412 | BnSC(Et)=N | Me | MeO | H |

TABLE 17-continued

| Number | R¹ | Rᵃ | R³ | R² |
|---|---|---|---|---|
| 413 | BnSC(n-Pr)=N | Me | MeO | H |
| 414 | 4-MeO-BnSC(c-Pr)=N | Me | MeO | H |
| 415 | BnSC(c-Pr)=N | Me | MeO | H |
| 416 | 4-Cl-BnSC(c-Pr)=N | Me | MeO | H |
| 417 | BnSC(c-Pent)=N | Me | MeO | H |
| 418 | 4-Me-BnSC(Me)=N | Me | MeO | H |
| 419 | 4-Cl-BnSC(Me)=N | Me | MeO | H |
| 420 | 4-MeO-BnSC(Me)=N | Me | MeO | H |
| 421 | EtSC(Ph)=N | Me | MeO | H |
| 422 | n-PrSC(Ph)=N | Me | MeO | H |
| 423 | i-BuSC(Me)=N | Me | MeO | H |
| 424 | BnSC(Me)=N | H | MeO | H |
| 425 | BnSC(c-Pr)=N | H | MeO | H |

TABLE 18

| Number | R¹ | Rᵃ | R³ | R² |
|---|---|---|---|---|
| 426 | MeSC(SMe)=N | Me | MeO | H |
| 427 | 4-MeO-BnSC(SMe)=N | Me | MeO | H |
| 428 | PhSC(SMe)=N | Me | MeO | H |
| 429 | n-BuSC(SMe)=N | Me | MeO | H |
| 430 | BnSC(SMe)=N | Me | MeO | H |
| 431 | 4-Cl-BnSC(SMe)=N | Me | MeO | H |
| 432 | 4-Me-BnSC(SMe)=N | Me | MeO | H |
| 433 | 4-CF₃-BnSC(SMe)=N | Me | MeO | H |
| 434 | 4-CF₃O-BnSC(SMe)=N | Me | MeO | H |
| 435 | EtSC(SEt)=N | Me | MeO | H |
| 436 | BnSC(SMe)=N | Me | MeO | H |
| 437 | MeSC(=S)—NH | Me | MeO | H |
| 438 | BnSC(=S)—NH | Me | MeO | H |
| 439 | 4-Cl-BnSC(=S)—NH | Me | MeO | H |
| 440 | 4-Me-BnSC(=S)—NH | Me | MeO | H |
| 441 | 4-CF₃-BnSC(=S)—NH | Me | MeO | H |
| 442 | 2-Me-BnSC(SMe)=N | Me | MeO | H |
| 443 | 4-Et-BnSC(SMe)=N | Me | MeO | H |
| 444 | 4-Cl-BnSC(S(c-Pr))=N | Me | MeO | H |
| 445 | 4-Me-BnSC(S(c-Pr))=N | Me | MeO | H |
| 446 | 4-CF₃-BnSC(S(c-Pr))=N | Me | MeO | H |
| 447 | 4-CF₃O-BnSC(S(c-Pr))=N | Me | MeO | H |
| 448 | 4-MeO-BnSC(S(c-Pr))=N | Me | MeO | H |
| 449 | BnSC(SMe)=N | H | MeO | H |
| 450 | BnSC(=S)—NH | H | MeO | H |

TABLE 19

| Number | R¹ | Rᵃ | R³ | R² |
|---|---|---|---|---|
| 451 | Et₃CC≡C | H | MeO | H |
| 452 | Et₃CC≡C | H | Cl | H |
| 453 | Et₃CC≡C | Me | MeO | H |
| 454 | Et₃CC≡C | Me | Cl | H |
| 455 | Me₃SiC≡C | H | MeO | H |
| 456 | Me₃SiC≡C | H | Cl | H |
| 457 | Me₃SiC≡C | Me | MeO | H |
| 458 | Me₃SiC≡C | Me | Cl | H |
| 459 | Et₃SiC≡C | Me | MeO | H |
| 460 | Me₂C(n-Bu)C≡C | Cl | MeO | H |
| 461 | c-Hex-C≡C | Me | MeO | H |
| 462 | 4-Cl-PhOC(Me)₂C≡C | Me | MeO | H |
| 463 | PhOC(Me)₂C≡C | Me | MeO | H |
| 464 | Me₂C(n-Bu)C≡C | Me | MeO | H |
| 465 | Me₂C(Ph)C≡C | Me | MeO | H |
| 466 | Et₂C(OEt)C≡C | Me | MeO | H |
| 467 | Et₂C(Me)C≡C | Me | MeO | H |
| 468 | Et₃CC≡C | Cl | MeO | H |
| 469 | Me₃SiC≡C | Cl | MeO | H |
| 470 | Me₃SiC≡C | H | MeO | Me |
| 471 | Et₃CC≡C | H | MeO | Me |
| 472 | Et₃CC≡C | H | Cl | Me |
| 473 | Et₃CC≡C | Me | MeS | H |

TABLE 19-continued

| Number | R¹ | Rᵃ | R³ | R² |
|---|---|---|---|---|
| 474 | Et₃CC≡C | Me | Cyano | H |
| 475 | Et₃CC≡C | Me | Me | H |

TABLE 20

| Number | R¹ | Rᵃ | R³ | R² |
|---|---|---|---|---|
| 476 | HOCH₂ | H | MeO | H |
| 477 | 3-CF₃-PhC(Me)=NOCH₂ | H | MeO | H |
| 478 | 4-MeO-Ph | Me | MeO | H |
| 479 | 4-CF₃-Ph | Me | MeO | H |
| 480 | 4-F-Ph | Me | MeO | H |
| 481 | 2-MeO-Ph | Me | MeO | H |
| 482 | 2,4-Cl₂-Ph | Me | MeO | H |
| 483 | 3,5-Cl₂-Ph | Me | MeO | H |
| 484 | 5-chloro-2-thienyl | Me | MeO | H |
| 485 | HOCH₂ | Me | MeO | H |
| 486 | Ph | Et | MeO | H |
| 487 | Ph | Cl | MeO | H |
| 488 | 4-NO₂-Ph | Me | MeO | H |
| 489 | 4-CN-Ph | Me | MeO | H |
| 490 | 4-MeS-Ph | Me | MeO | H |
| 491 | 4-Et-Ph | Me | MeO | H |
| 492 | 4-EtO-Ph | Me | MeO | H |
| 493 | 5-CF₃-Py-2-yl | Me | MeO | H |
| 494 | (3,4-OCH₂O)-Ph | Me | MeO | H |
| 495 | (3,4-OCF₂O)-Ph | Me | MeO | H |
| 496 | 4-CF₃O-Ph | Me | MeO | H |
| 497 | 4-PhO-Ph | Me | MeO | H |
| 498 | 4-CF₂BrO-Ph | Me | MeO | H |
| 499 | 2,5-Me₂-Ph | Me | MeO | H |
| 500 | 3-PhO-Ph | Me | MeO | H |

TABLE 21

| Number | R¹ | Rᵃ | R³ | R² |
|---|---|---|---|---|
| 501 | Br | Cl | MeO | H |
| 502 | Br | MeO | MeO | H |
| 503 | Br | Et | MeO | H |
| 504 | Br | CF₃ | MeO | H |
| 505 | Ph | CF₃ | MeO | H |
| 506 | Ph | MeO | MeO | H |
| 507 | 4-MeO-Ph | MeO | MeO | H |
| 508 | 4-Cl-Ph | MeO | MeO | H |
| 509 | 3-Cl-Ph | MeO | MeO | H |
| 510 | 2-Cl-Ph | MeO | MeO | H |
| 511 | 4-Me-Ph | MeO | MeO | H |
| 512 | 3-Me-Ph | MeO | MeO | H |
| 513 | 2-Me-Ph | MeO | MeO | H |
| 514 | 3,4-Cl₂-Ph | MeO | MeO | H |
| 515 | 3-Cl-Ph | Cl | MeO | H |
| 516 | 2-Cl-Ph | Cl | MeO | H |
| 517 | 4-Me-Ph | Cl | MeO | H |
| 518 | 3-Me-Ph | Cl | MeO | H |
| 519 | 2-Me-Ph | Cl | MeO | H |
| 520 | 3,4-Cl₂-Ph | Cl | MeO | H |
| 521 | 3-CN-Ph | Me | MeO | H |
| 522 | 2-CN-Ph | Me | MeO | H |
| 523 | 5-Cl-Py-2-yl | Me | MeO | H |
| 524 | 6-Cl-Py-3-yl | Me | MeO | H |
| 525 | 3,4-(MeO)₂-Ph | Me | MeO | H |

TABLE 22

| Number | R¹ | Rᵃ | R³ | R² |
|---|---|---|---|---|
| 526 | Me₃CC≡C | Me | MeO | H |
| 527 | Me₃SiCH₂C≡C | Me | MeO | H |
| 528 | Br | F | MeO | H |

TABLE 22-continued

| Number | R¹ | Rᵃ | R³ | R² |
|---|---|---|---|---|
| 529 | Ph | F | MeO | H |
| 530 | 3-OBn-Ph | Me | MeO | H |
| 531 | 3-Ph-Ph | Me | MeO | H |
| 532 | 3,5-F₂-Ph | Me | MeO | H |
| 533 | 2-F-Ph | Me | MeO | H |
| 534 | 3-(4-pyrimidinyl)-Ph | Me | MeO | H |
| 535 | Ph-CH₂C≡C | Me | MeO | H |
| 536 | Ph-C≡C | Me | MeO | H |
| 537 | Ph | Me | MeO | Me |
| 538 | Ph | Me | c-Pr | H |
| 539 | Ph | Me | Et | H |
| 540 | Ph | Me | Vinyl | H |
| 541 | Ph | Me | C≡CH | H |
| 542 | t-BuCH=CH | Me | MeO | H |
| 543 | 6-CF₃-Py-2-yl | Me | MeO | H |
| 544 | 6-Ph-Py-2-yl | Me | MeO | H |
| 545 | 6-OMe-Py-2-yl | Me | MeO | H |
| 546 | 6-Me-2-pyrimidinyl | Me | MeO | H |
| 547 | 6-CF₃-2-pyrimidinyl | Me | MeO | H |
| 548 | 6-Ph-2-pyrimidinyl | Me | MeO | H |
| 549 | 6-Cl-2-pyrimidinyl | Me | MeO | H |
| 550 | 3-(2-pyrimidinyl)-Ph | Me | MeO | H |

TABLE 23

| Number | R¹ | Rᵃ | R³ | R² |
|---|---|---|---|---|
| 551 | 6-OBn-2-pyrimidinyl | Me | MeO | H |
| 552 | 6-OPh-2-pyrimidinyl | Me | MeO | H |
| 553 | 6-CH₂OPh-2-pyrimidinyl | Me | MeO | H |
| 554 | 2-thiazolyl | Me | MeO | H |
| 555 | 4-thiazolyl | Me | MeO | H |
| 556 | 2-Ph-4-thiazolyl | Me | MeO | H |
| 557 | 2-Ph-5-thiazolyl | Me | MeO | H |
| 558 | 4-Ph-2-thiazolyl | Me | MeO | H |
| 559 | 5-Ph-2-thiazolyl | Me | MeO | H |
| 560 | sec-Bu-C≡C | Me | MeO | H |
| 561 | i-Bu-C≡C | Me | MeO | H |
| 562 | n-Bu-C≡C | Me | MeO | H |
| 563 | n-Pr-C≡C | Me | MeO | H |
| 564 | i-Pr-C≡C | Me | MeO | H |
| 565 | c-Pr-C≡C | Me | MeO | H |
| 566 | c-Pent-C≡C | Me | MeO | H |
| 567 | 6-OBn-Py-2-yl | Me | MeO | H |
| 568 | 6-CH₂OPh-Py-2-yl | Me | MeO | H |
| 569 | 2-Cl-PhOC(Me)2C≡C | Me | MeO | H |
| 570 | 3-Cl-PhOC(Me)2C≡C | Me | MeO | H |
| 571 | 6-sec-Bu-2-pyrimidinyl | Me | MeO | H |
| 572 | 6-n-Bu-2-pyrimidinyl | Me | MeO | H |
| 573 | 4,6-Me2-2-pyrimidinyl | Me | MeO | H |
| 574 | 6-OMe-2-pyrimidinyl | Me | MeO | H |
| 575 | benzothiazole-2-yl | Me | MeO | H |

In the above Tables, Me, Et, Pr, Bu, Pent, Hex, Ph, Py and Bn represent methyl, ethyl, propyl, butyl, pentyl, hexyl, phenyl, pyridyl, and benzyl, respectively. Also, n-, i-, sec-, t- and c- represent normal-, iso-, secondary-, tertiary, cyclo, respectively.

Formulation Examples are set forth below. In the Formulation Examples, all the "parts" represent "parts by weight", and the compounds of the present invention are designated by the corresponding numbers as shown in Tables 1–23.

Formulation Example 1

A wettable powder of each compound is obtained by thoroughly pulverizing and mixing 50 parts of each of the compounds 1 to 575 of the present invention, 3 parts of calcium ligninsulfonate, 2 parts of sodium laurylsulfate and 45 parts of synthetic hydrous silicate.

Formulation Example 2

A suspension of each compound is obtained by mixing 25 parts of each of the compounds 1 to 575 of the present invention, 3 parts of polyoxyethylene sorbitan monooleate, 3 parts of CMC and 69 parts of water, and subjecting the resultant mixture to wet pulverization until the particle size thereof becomes 5 microns or less.

Formulation Example 3

A dust preparation of each compound is obtained by thoroughly pulverizing and mixing 2 parts of each of the compounds 1 to 575 of the present invention, 88 parts of kaolin clay and 10 parts of talc.

Formulation Example 4

An emulsifiable concentrate of each compound is obtained by thoroughly mixing 20 parts of each of the compounds 1 to 575 of the present invention, 14 parts of polyoxyethylene styryl phenyl ether, 6 parts of calcium dodecylbenzene sulfonate and 60 parts of xylene.

Formulation Example 5

Granules of each compound is obtained by thoroughly pulverizing and mixing 2 parts of each of the compounds 1 to 575 of the present invention, 1 part of synthetic hydrous silicate, 2 parts of calcium ligninsulfonate, 30 parts of bentonite and 65 parts of kaoline clay, adding water to the resultant mixture, followed by kneading, granulating and drying.

Formulation Example 6

A 20% aqueous suspension of each compound is obtained by mixing 20 parts of each of the compounds 1 to 575 of the present invention and 1.5 parts of sorbitan trioleate with 28.5 parts of an aqueous solution containing 2 parts of polyvinyl alcohol, pulverizing the mixture with a sand grinder (particle size: 3 μm or less), adding 40 parts of an aqueous solution containing 0.05 parts of xanthan gum and 0.1 parts of aluminum magnesium silicate thereto, further adding 10 parts of propylene glycol, and then stirring and mixing the resultant mixture.

The effectiveness of the compounds of the present as an agricultural and horticultural fungicide are illustrated by the following Test Examples. The compounds of the present invention are designated by the corresponding compound numbers shown in Tables 1 to 23.

The control effects of the compounds of the present invention were determined by visual observation as to infected areas on treated plants at the time of examination, followed by comparison between the infected areas on plants of untreated groups and those on plants of groups treated with the compounds of the present invention.

Test Example 1
Preventive Efficacy Against *Pyricularia oryzae* on Rice

Plastic pots were filled with sand loam, and seeds of rice plants (Nihon Bare) were sowed therein and cultivated in a greenhouse for 20 days. The compounds 1, 2, 6, 7, 8, 10, 19, 21, 28, 45, 46, 47, 48, 49, 50, 152, 176, 296, 299, 303, 314, 457, 459, 478, 480, 487, 489, 526, 527, 529, 530, 531, 532, 533, 534 and 535 of the present invention formulated in wettable powders according to Formulation Example 1 were diluted with water to a prescribed concentration (500 ppm), and the dilution was well sprayed over the foliage of the rice plants by foliage spraying. After the spraying, the plants were air-dried, and inoculated with a suspension of *Pyricularia oryzae* by spraying. After the inoculation, the plants were placed in a humid condition at 28° C. for 6 days, and the control effect was examined. The results showed that infected areas on the plants of the groups treated with the compounds of the present invention were not greater than 10% of infected areas on those of the untreated groups.

Test Example 2
Curative Efficacy Against *Erysiphe graminis* f. sp. tritici on Wheat
Plastic pots were filled with sand loam, and seeds of wheat (Norin 73 go) were sowed therein and cultivated in a greenhouse for 10 days. The seedlings of wheat entering into the 2 leaf stage were inoculated with spores of *Erysiphe graminis* f. sp. tritici by dusting. After the inoculation, the seedlings were placed at 23° C. in a greenhouse for 2 days. The compounds 1, 6, 7, 19, 21, 28, 45, 46, 47, 49, 50, 152, 176, 314, 457, 459, 480, 487, 489, 529, 530, 531, 532 and 533 of the present invention formulated in suspensions according to Formulation Example 2 were diluted with water to a prescribed concentration (500 ppm), and the dilution was well sprayed by foliage spraying over the foliage of the wheat inoculated with *Erysiphe graminis*. After the spraying, the seedlings were placed in lighting for 7 days, and the control effect was examined. The results showed that infected areas on the plants of the groups treated with the compounds of the present invention were not greater than 10% of infected areason those of the untreated group.

Test Example 3
Preventive Efficacy Against *Puccinia recondita* on Wheat
Plastic pots were filled with sand loam, and seeds of wheat (Norin 73 go) were sowed therein and cultivated in a greenhouse for 10 days. The compounds 1, 6, 7, 8, 10, 21, 28, 45, 46, 47, 48, 49, 50, 152, 176, 299, 314, 457, 478, 480, 526, 529, 530, 531, 532, 533 and 535 of the present invention formulated in emulsifiable concentrates according to Formulation Example 4 were diluted with water to a prescribed concentration (500 ppm), and the dilution was well sprayed over the foliage of the wheat by foliage spraying. After the spraying, the plants were air-dried, and inoculated with spores of *Puccinia recondite*. After the inoculation, the plants were first placed in a dark and humid condition at 23° C. for 1 day and then in lighting for 6 days, and the control effect was examined. The results showed that infected areas on the plants of the groups treated with the compounds of the present invention were not greater than 10% of infected areas on those of the untreated groups.

Test Example 4
Preventive Efficacy Against *Leptosphaeria nodorum* on Wheat
Plastic pots were filled with sand loam, and seeds of wheat (Norin 73 go) were sowed therein and cultivated in a greenhouse for 10 days. The compounds 1, 2, 6, 7, 8, 10, 11, 21, 28, 45, 46, 47, 48, 49, 50, 152, 176, 239, 299, 303, 314, 457, 478, 480, 489, 526, 529, 530, 531, 533, 534 and 535 of the present invention formulated in emulsifiable concentrates according to Formulation Example 4 were diluted with water to a prescribed concentration (500 ppm), and the dilution was well sprayed over the foliage of the wheat by foliage spraying. After the spraying, the plants were air-dried and inoculated with a spore suspension of *Leptosphaeria nodorum* by spraying. After the inoculation, the plants were first placed in a dark and humid condition at 15° C. for 4 days and then in lighting for 7 days, and the control effect was examined. The results showed that infected areas on the plants of the groups treated with the compounds of the present invention were not greater than 10% of infected areas on those of the untreated groups.

Test Example 5
Preventive Efficacy Against *Pseudocercosporella herpotrichoides* on Wheat
Plastic pots were filled with sand loam, and seeds of wheat (Norin 73 go) were sowed therein and cultivated in a greenhouse for 10 days. The compounds 1, 6, 7, 10, 21, 28, 45, 46, 47, 49, 50, 152, 176, 239, 303, 314, 457, 480, 489, 526, 529, 530, 531, 532, 533 and 535 of the present invention formulated in emulsifiable concentrates according to Formulation Example 4 were diluted with water to a prescribed concentration (500 ppm), and the dilution was well sprayed over the foliage of the wheat by foliage spraying. After the spraying, the plants were air-dried and inoculated with PDA medium containing spores of *Pseudocercosporella herpotrichoides* at their roots. After the inoculation, the plants were first placed in a dark and humid condition at 15° C. for 7 days and then in lighting for 4 days, and the control effect was examined. The results showed that infected areas on the plants of the groups treated with the compounds of the present invention were not greater than 10% of infected areas on those of the untreated groups.

Test Example 6
Preventive Efficacy Against *Plasmopara viticola* on Grape
Plastic pots were filled with sand loam, and seeds of grapes (Berry A) were sowed therein and cultivated in a greenhouse for 40 days. The compounds 6, 7, 8, 10, 19, 21, 28, 45, 46, 47, 48, 49, 50, 303, 457, 459, 478, 480, 487, 489, 526, 527, 528, 529, 530, 531, 532, 533, 534 and 535 of the present invention formulated in suspensions according to Formulation Example 2 were diluted with water to a prescribed concentration (200 ppm), and the dilution was well sprayed over the foliage of the grapes by foliage spraying. After the spraying, the plants were air-dried and inoculated with a suspension of *Plasmopara viticola* zoosporangia by spraying. After the inoculation, the plants were first placed in a humid condition at 23° C. for 1 day and then in a greenhouse for 6 days, and the control effect was examined. The results showed that infected areas on the plants of the groups treated with the compounds of the present invention were not greater than 10% of infected areas on those of the untreated groups.

Test Example 7
Preventive Efficacy Against *Bottytis cinerea* on Cucumber
Plastic pots were filled with sand loam, and seeds of cucumbers (Sagami Hanshiro) were sowed therein and cultivated in a greenhouse for 12 days. The compounds 6, 19, 21, 28, 46, 47, 48, 49, 50, 314, 457, 478, 480, 487, 526 and 533 of the present invention formulated in wettable powders according to Formulation Example 1 were diluted with water to a prescribed concentration (500 ppm), and the dilution was well sprayed over the foliage of the cucumbers by foliage spraying. After the spraying, the plants were air-dried, and PDA medium containing mycelia of *Botrytis cinerea* were attached on cucumber leaves. After the inoculation, the cucumbers were placed in a humid condition at 10° C. for 4 days, and the control effect was examined. The results showed that infected areas on the plants of the groups treated with the compounds of the present invention were not greater than 10% of infected areas on those of the untreated groups.

Test Example 8
Preventive Efficacy Against *Sphaerotheca fuliginea* on Cucumber

Plastic pots were filled with sand loam, and seeds of cucumbers (Sagami Hanshiro) were sowed therein and cultivated in a greenhouse for 12 days. The compounds 6, 7, 10, 21, 28, 45, 46, 47, 49, 50, 152, 457, 478, 480, 489, 526, 527, 529, 530, 531, 532 and 533 of the present invention formulated in suspensions according to Formulation Example 2 were diluted with water to a prescribed concentration (200 ppm), and the dilution was well sprayed over the foliage of the cucumbers by foliage spraying. After the spraying, the plants were air-dried and inoculated with spores of *Sphaerotheca fuliginea*. After the inoculation, the plants were placed in a 23° C. for 12 days, and the control effect was examined. The results showed that infected areas on the plants of the groups treated with the compounds of the present invention were not greater than 10% of infected areas on those of the untreated groups.

As described hereinabove, the compounds of the present invention have an excellent control effect against plant diseases.

What is claimed is:
1. A triazolone compound represented by the formula (I)

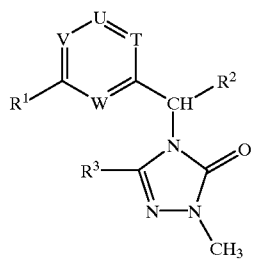

wherein
R$^1$ represents $C_{1-10}$ alkyl, $C_{2-10}$ alkenyl, $C_{2-10}$ alkynyl, halogen, nitro, cyano, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, $C_{2-19}$ heteroarylalkyl, $A^1$—$L^1$—, $A^1$—ON=CA$^2$—, $A^1$—ON=C(Me) CH$_2$ON=CA$^2$—, $A^1$C(A$^2$)=NOCH$_2$—, $A^1$SC(A$^2$)=N—, $A^1$C(=S)NH—, $A^1$SC(=S)NH—, $A^1$SC(SA$^2$)=N—, $A^1$—ON=C(CN)—, $A^1$—ON=C(Me) CH$_2$ON=C(CN)—, or $A^1$C(CN)=NOCH$_2$—(wherein L$^1$ represents oxygen, sulfur, carbonyl, —OCH$_2$—, —SCH$_2$—, —C(=O)O—, —OC(=O)—, —C(=O) OCH$_2$—, —NH—, or $C_{1-6}$ alkylimino; A$^1$ and A$^2$ are the same or different, and each represents hydrogen, $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalky, $C_{6-10}$ aryl, $C_{7-20}$ arylalkyl, $C_{1-9}$ heteroaryl, or $C_{2-19}$ heteroarylalkyl);

R$^2$ represents hydrogen, or $C_{1-6}$ alkyl;
R$^3$ represents $C_{1-6}$ alkoxy, $C_{1-6}$ alkylthio, cyano, halogen, vinyl, ethynyl, cyclopropyl, or $C_{1-6}$ alkyl;
one of T, U and V represents CR$^4$, another one represents CH or nitrogen, and the remaining one represents CR$^5$ or nitrogen;
W represents CR$^6$ or nitrogen; (wherein R$^4$, R$^5$ and R$^6$ are the same or different, and each represents hydrogen, halogen, $C_{1-6}$ alkyl, $C_{1-6}$ alkoxy, $C_{1-6}$ haloalkyl, $C_{1-6}$ haloalkoxy, cyano, nitro, $C_{2-6}$ alkoxycarbonyl, $C_{1-6}$ alkylthio, or $C_{1-6}$ haloalkylthio), and wherein, in R$^1$, A$^1$ and A$^2$ of the triazolone compound represented by the formula (I), the $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{1-9}$ heteroaryl and/or $C_{2-19}$ heteroarylalkyl may be substituted with the same or different substituents which are one or more substituents selected from the following Group A; and
the $C_{6-10}$ aryl and $C_{7-20}$ arylalkyl may be substituted with the same or different substituents which are one or more substituents selected from the group consisting of the following Group A and Group B;
Group A halogen, $C_{1-10}$ alkyl, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, phenoxymethyl, $C_{1-9}$ heteroaryl, ($C_{1-9}$ heteroaryl)methyloxy, ($C_{1-9}$ heteroaryl)oxymethyl, $C_{1-9}$ heteroaryloxy (wherein each of the phenyl, phenoxy, benzyloxy, phenoxymethyl, $C_{1-9}$ heteroary, ($C_{1-9}$ heteroaryl)methyloxy, ($C_{1-9}$ heteroaryl)oxymethyl, and $C_{1-9}$ heteroaryloxy may be substituted with one or more substituents selected from the group consisting of halogen, $C_{1-6}$ alkyl, $C_{1-6}$ alkoxy, trifluoromethyl, and cyano), hydroxyl, cyano and nitro;
Group B methylenedioxy and difluoromethylenedioxy (each of the methylenedioxy and difluoromethylenedioxy is attached to the two adjacent carbon atoms of the aryl moiety).

2. A triazolone compound represented by the formula (I)

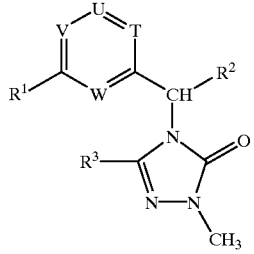

wherein
R$^1$ represents $C_{1-10}$ alkyl, $C_{2-10}$ alkenyl, $C_{2-10}$ alkynyl, halogen, nitro, cyano, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, $C_{2-19}$ heteroarylalkyl, $A^1$—$L^1$—, $A^1$—ON=CA$^2$—, $A^1$—ON=C(Me) CH$_2$ON=CA$^2$—, $A^1$C(A$^2$)=NOCH$_2$—, $A^1$SC(A$^2$)=N—, $A^1$C(=S)NH—, $A^1$SC(=S)NH—, $A^1$SC(SA$^2$)=N—, $A^1$—ON=C(CN)—, $A^1$—ON=C(Me) CH$_2$ON=C(CN)—, or $A^1$C(CN)=NOCH$_2$—, (wherein L$^1$ represents oxygen, sulflur, carbonyl, —OCH$_2$—, —SCH$_2$—, —C(=O)O—, —OC(=O)—, —C(=O)OCH$_2$—, —NH—, or $C_{1-6}$ alkylimino; A$^1$ and A$^2$ are the same or different, and each represents hydrogen, $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, or $C_{2-19}$ heteroarylalkyl);
R$^2$ represents hydrogen, or $C_{1-6}$ alkyl;
R$^3$ represents $C_{1-6}$ alkoxy, $C_{1-6}$ alkylthio, cyano, halogen, vinyl, ethynyl, cyclopropyl, or $C_{1-6}$ alkyl;
one of T, U and V represents CR$^4$, another one represents CH or nitrogen, and the remaining one represents CR$^5$ or nitrogen;

W represents $CR^6$ or nitrogen; (wherein $R^4$, $R^5$ and $R^6$ are the same or different, and each represents hydrogen, halogen, $C_{1-6}$ alkyl, $C_{1-6}$ alkoxy, $C_{1-6}$ haloalkyl, $C_{1-6}$ haloalkoxy, cyano, nitro, $C_{2-6}$ alkoxycarbonyl, $C_{1-6}$ alkylthio, or $C_{1-6}$ haloalkylthio), and wherein, in $R^1$, $A^1$ and $A^2$ of the triazolone compound represented by the formula (I), the $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{1-9}$ heteroaryl and $C_{2-19}$ heteroarylalkyl may be substituted with the same or different substituents which are one or more substituents selected from the following Group A1; and the $C_{6-10}$ aryl and $C_{7-20}$ arylalkyl may be substituted with the same or different substituents which are one or more substituents selected from the group consisting of the following Group A1 and Group B:

Group A1 halogen, $C_{1-10}$ alky, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, pyridine-2-yloxy (wherein each of the phenyl, phenoxy, benzyloxy, and pyridine-2-yloxy may be substituted with one or more substituents selected from the group consisting of halogen, $C_{1-6}$ alkyl, $C_{1-6}$ alkoxy, trifluoromethyl, and cyano), hydroxyl, cyano and nitro;

Group B methylenedioxy and difluoromethylenedioxy (each of the methylenedioxy and difluoromethylenedioxy is attached to the two adjacent carbon atoms of the aryl moiety).

3. A triazolone compound represented by the formula (I)

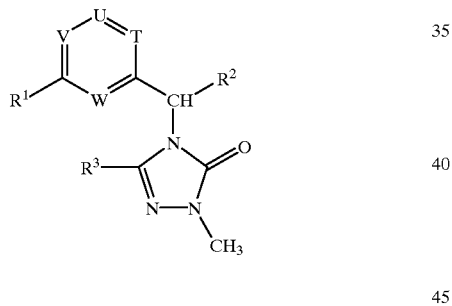

wherein $R^1$ represents $C_{1-10}$ alkyl, $C_{2-10}$ alkenyl, $C_{2-10}$ alkynyl, halogen, nitro, cyano, $C_{3-10}$ cycloalkyl, $C_{4-20}$ cycloalkylalkyl, $C_{5-20}$ cycloalkenyl, $C_{6-20}$ cycloalkenylalkyl, $C_{6-10}$ aryl, $C_{7-20}$ arylalkyl, $C_{1-9}$ heteroaryl, $C_{2-19}$ heteroarylalkyl, $A^1-L^1-$, $A^1-ON=CA^2-$, $A^1-ON=C(Me)CH_2ON=CA^2-$, $A^1C(A^2)=NOCH_2-$, $A^1SC(A^2)=N-$, $A^1C(=S)NH-$, $A^1SC(=S)NH-$, $A^1SC(SA^2)=N-$, $A^1-ON=C(CN)-$, $A^1-ON=C(Me)CH_2ON=C(CN)-$, or $A^1C(CN)=NOCH_2-$ (wherein $L^1$ represents oxygen, sulfur, carbonyl, $-OCH_2-$, $-SCH_2-$, $-C(=O)O-$, $-OC(=O)-$, $-C(=O)OCH_2-$, $-NH-$, or $C_{1-6}$ alkylimino; $A^1$ and $A^2$ are the same or different, and each represents hydrogen, $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, or $C_{2-19}$ heteroarylalkyl);

$R^2$ represents hydrogen, or $C_{1-6}$ alkyl;

$R^3$ is $C_{1-6}$ alkoxy, $C_{1-6}$ alkylthio, cyano, halogen, or $C_{1-6}$ alkyl;

one of T, U and V represents $CR^4$, another one represents CH or nitrogen, and the remaining one represents $CR^5$ or nitrogen;

W represents $CR^6$ or nitrogen; (wherein $R^4$, $R^5$ and $R^6$ are the same or different, and each represents hydrogen, halogen, $C_{1-6}$ alkyl, $C_{1-6}$ alkoxy, $C_{1-6}$ haloalkyl, $C_{1-6}$ haloalkoxy, cyano, nitro, $C_{2-6}$ alkoxycarbonyl, $C_{1-6}$ alkylthio, or $C_{1-6}$ haloalkylthio), and wherein, in $R^1$, $A^1$ and $A^2$ of the triazolone compound represented by the formula (I), the $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{1-9}$ heteroaryl and/or $C_{2-19}$ heteroarylalkyl may be substituted with the same or different substituents which are one or more substituents selected from the following Group A; and the $C_{6-10}$ aryl and $C_{7-20}$ arylalkyl may be substituted with the same or different substituents which are one or more substituents selected from the group consisting of the following Group A and Group B:

Group A halogen, $C_{1-10}$ alkyl, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, phenoxymethyl, $C_{1-9}$ heteroaryl, ($C_{1-9}$ heteroaryl)methyloxy, ($C_{1-9}$ heteroaryl)oxymethyl, $C_{1-9}$ heteroaryloxy (wherein each of the phenyl, phenoxy, benzyloxy, phenoxymethyl, $C_{1-9}$ heteroaryl, ($C_{1-9}$ heteroaryl)methyloxy, ($C_{1-9}$ heteroaryl)oxymethyl, and $C_{1-9}$ heteroaryloxy may be substituted with one or more substituents selected from the group consisting of halogen, $C_{1-6}$ alkyl, $C_{1-6}$ alkoxy, trifluoromethyl, and cyano), hydroxyl, cyano and nitro;

Group B methylenedioxy and difluoromethylenedioxy (each of the methylenedioxy and difluoromethylenedioxy is attached to the two adjacent carbon atoms of the aryl moiety).

4. A triazolone compound represented by the formula (I)

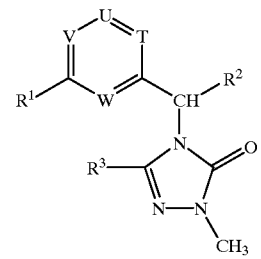

wherein $R^1$ represents $C_{1-10}$ alkyl, $C_{2-10}$ alkenyl, $C_{2-10}$ alkynyl, halogen, nitro, cyano, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, $C_{2-19}$ heteroarylalkyl, $A^1-L^1-$, $A^1-ON=CA^2-$, $A^1-ON=C(Me)CH_2ON=CA^2-$, $A^1C(A^2)=NOCH_2-$, $A^1SC(A^2)=N-$, $A^1C(=S)NH-$, $A^1SC(=S)NH-$, $A^1SC(SA^2)=N-$, $A^1-ON=C(CN)-$, $A^1-ON=C(Me)CH_2ON=C(CN)-$, or $A^1C(CN)=NOCH_2-$ (wherein $L^1$ represents oxygen, sulfur, carbonyl, $-OCH_2-$, $-SCH_2-$, $-C(=O)O-$, $-OC(=O)-$, $-C(=O)OCH_2-$, $-NH-$, or $C_{1-6}$ alkylimino; $A^1$ and $A^2$ are the same or different, and each represents hydrogen, $C_{1-10}$ alkyl, $C_{2-10}$ alkenyl, $C_{2-10}$ alkynyl, $C_{3-10}$ cycloalkyl, C4-20 cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, or $C_{2-19}$ heteroarylalkyl);

$R^2$ represents hydrogen, or $C_{1-6}$ alkyl;

$R^3$ is $C_{1-6}$ alkoxy, $C_{1-6}$ alkylthio, cyano, halogen, or $C_{1-6}$ alkyl;

one of T, U and V represents $CR^4$, another one represents CH or nitrogen, and the remaining one represents $CR^5$ or nitrogen;

W represents $CR^6$ or nitrogen; (wherein $R^4$, $R^5$ and $R^6$ are the same or different, and each represents hydrogen, halogen, $C_{1-6}$ alkyl, $C_{1-6}$ alkoxy, $C_{1-6}$ haloalkyl, $C_{1-6}$ haloalkoxy, cyano, nitro, $C_{2-6}$ alkoxycarbonyl, $C_{1-6}$ alkylthio, or $C_{1-6}$ haloalkylthio), and wherein, in $R^1$, $A^1$ and $A^2$ of the triazolone compound represented by the formula (I), the $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{1-9}$ heteroaryl and $C_{2-19}$ heteroarylalkyl may be substituted with the same or different substituents which are one or more substituents selected from the following Group A1; and the $C_{6-10}$ aryl and $C_{7-20}$ arylalkyl may be substituted with the same or different substituents which are one or more substituents selected from the group consisting of the following Group A1 and Group B:

Group A1 halogen, $C_{1-10\ alkyl}$, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, pyridine-2-yloxy (wherein each of the phenyl, phenoxy, benzyloxy, and pyridine-2-yloxy may be substituted with one or more substituents selected from the group consisting of halogen, $C_{1-6}$ alkyl, $C_{1-6}$ alkoxy, trifluoromethyl, and cyano), hydroxyl, cyano and nitro;

Group B methylenedioxy and difluoromethylenedioxy (each of the methylenedioxy and difluoromethylene-dioxy is attached to the two adjacent carbon atoms of the aryl moiety).

5. A triazolone compound represented by the formula (IV)

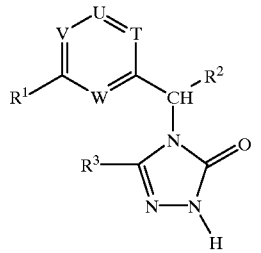

wherein wherein $R^1$ represents $C_{1-10}$ alkyl, $C_{2-10}$ alkenyl, $C_{2-10}$ alkynyl, halogen, nitro, cyano, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, $C_{2-19}$ heteroarylalkyl, $A^1$—$L^1$—, $A^1$—O N═C$A^2$—, $A^1$—O N═C(Me) CH$_2$ON═CA$^2$—, $A^1$C($A^2$)═NOCH$_2$—, $A^1$SC($A^2$)═N—, $A^1$C(═S)NH—, $A^1$SC(═S)NH—, $A^1$SC(S$A^2$)═N—, $A^1$—ON═C(CN)—, $A^1$—ON═C(Me)CH$_2$ON═C(CN)—, or $A^1$C(CN)═NOCH$_2$—(wherein $L^1$ represents oxygen, sulfur, carbonyl, —OCH$_2$—, —SCH$_2$—, —C(═O)O—, —OC(═O)—, —C(═O)OCH$_2$—, —NH—, or $C_{1-6}$ alkylimino; $A^1$ and $A^2$ are the same or different, and each represents hydrogen, $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, or $C_{2-19}$ heteroarylalkyl);

$R^2$ represents hydrogen, or $C_{1-6}$ alkyl;

$R^3$ represents $C_{1-6}$ alkoxy, $C_{1-6}$ alkylthio, cyano, halogen, vinyl, ethynyl, cyclopropyl, or $C_{1-6}$ alkyl;

one of T, U and V represents $CR^4$, another one represents CH or nitrogen, and the remaining one represents $CR^5$ or nitrogen; and W represents $CR^6$ or nitrogen; (wherein $R^4$, $R^5$ and $R^6$ are the same or different, and each represents hydrogen, halogen, $C_{1-6}$ alkyl, $C_{1-6}$ alkoxy, $C_{1-6}$ haloalkyl, $C_{1-6}$ haloalkoxy, cyano, nitro, $C_{2-6}$ alkoxycarbonyl, $C_{1-6}$ alkylthio, or $C_{1-6}$ haloalkylthio), and wherein, in $R^1$, $A^1$ and $A^2$ of the triazolone compound represented by the formula (I), the $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{1-9}$ heteroaryl and/or $C_{2-19}$ heteroarylalkyl may be substituted with the same or different substituents which are one or more substituents selected from the following Group A; and the $C_{6-10}$ aryl and $C_{7-20}$ arylalkyl may be substituted with the same or different substituents which are one or more substituents selected from the group consisting of the following Group A and Group B:

Group A halogen, $C_{1-10}$ alkyl, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, phenoxymethyl, $C_{1-9}$ heteroaryl, ($C_{1-9}$ heteroaryl)methyloxy, ($C_{1-9}$ heteroaryl)oxymethyl, $C_{1-9}$ heteroaryloxy (wherein each of the phenyl, phenoxy, benzyloxy, phenoxymethyl, $C_{1-9}$ heteroaryl, ($C_{1-9}$ heteroaryl)methyloxy, ($C_{1-9}$ heteroaryl)oxymethyl, and $C_{1-9}$ heteroaryloxy may be substituted with one or more substituents selected from the group consisting of halogen, $C_{1-6}$ alkyl, $C_{1-6}$ alkoxy, trifluoromethyl, and cyano), hydroxyl, cyano and nitro;

Group B methylenedioxy and difluoromethylenedioxy (each of the methylenedioxy and difluoromethylene-dioxy is attached to the two adjacent carbon atoms of the aryl moiety).

6. A triazolone compound represented by the formula (IV)

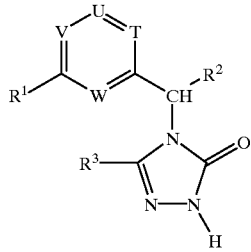

wherein $R^1$ represents $C_{1-10}$ alkyl, $C_{2-10}$ alkenyl, $C_{2-10}$ alkynyl, halogen, nitro, cyano, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, $C_{2-19}$ heteroarylalkyl, $A^1-L^1-$, $A^1-ON=CA^2-$, $A^1-ON=C(Me)CH_2ON=CA^2-$, $A^1C(A^2)=NOCH_2-$, $A^1SC(A^2)=N-$, $A^1C(=S)NH-$, $A^1SC(=S)NH-$, $A^1SC(SA^2)=N-$, $A^1-ON=C(CN)-$, $A^1-ON=C(Me)CH_2ON=C(CN)-$, or $A^1C(CN)=NOCH_2-$ (wherein $L^1$ represents oxygen, sulfur, carbonyl, $-OCH_2-$, $-SCH_2-$, $-C(=O)O-$, $-OC(=O)-$, $-C(=O)OCH_2-$, $-NH-$, or $C_{1-6}$ alkylimino; $A^1$ and $A^2$ are the same or different, and each represents hydrogen, $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ hereoaryl, or $C_{2-19}$ heteroarylalkyl);

$R^2$ represents hydrogen, or $C_{1-6}$ alkyl;

$R^3$ represents $C_{1-6}$ alkoxy, $C_{1-6}$ alkylthio, cyano, halogen, vinyl, ethynyl, cyclopropyl, or $C_{1-6}$ alkyl;

one of T, U and V represents $CR^4$, another one represents CH or nitrogen, and the remaining one represents $CR^5$ or nitrogen; and W represents $CR^6$ or nitrogen; (wherein $R^4$, $R^5$ and $R^6$ are the same or different, and each represents hydrogen, halogen, $C_{1-6}$ alkyl, $C_{1-6}$ alkoxy, $C_{1-6}$ haloalkyl, $C_{1-6}$ haloalkoxy, cyano, nitro, $C_{2-6}$ alkoxycarbonyl, $C_{1-6}$ alkylthio, or $C_{1-6}$ haloalkylthio), and wherein, in $R^1$, $A^1$ and $A^2$ of the triazolone compound represented by the formula (I), the $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{1-9}$ heteroaryl and $C_{2-19}$ heteroarylalkyl may be substituted with the same or different substituents which are one or more substituents selected from the following Group A1; and the $C_{6-10}$ aryl and $C_{7-20}$ arylalkyl may be substituted with the same or different substituents which are one or more substituents selected from the group consisting of the following Group A1 and Group B:

Group A1 halogen, $C_{1-10}$ alkyl, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, pyridine-2-yloxy (wherein each of the phenyl, phenoxy, benzyloxy, and pyridine-2-yloxy may be substituted with one or more substituents selected from the group consisting of halogen, $C_{1-6}$ alkyl, $C_{1-6}$ alkoxy, trifluoromethyl, and cyano), hydroxyl, cyano and nitro;

Group B methylenedioxy and difluoromethylenedioxy (each of the methylenedioxy and difluoromethylenedioxy is attached to the two adjacent carbon atoms of the aryl moiety).

7. A triazolone compound represented by the formula (IV)

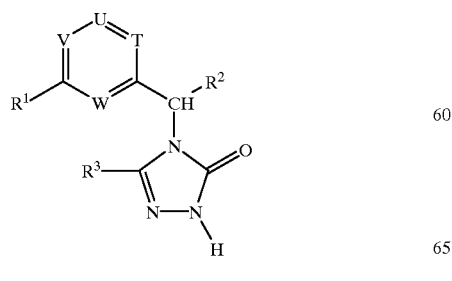

wherein $R^1$ represents $C_{1-10}$ alkyl, $C_{2-10}$ alkenyl, $C_{2-10}$ alkynyl, halogen, nitro, cyano, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, $C_{2-19}$ heteroarylalkyl, $A^1-L^1-$, $A^1-ON=CA^2-$, $A^1-ON=C(Me)CH_2ON=CA^2-$, $A^1C(A^2)=NOCH_2-$, $A^1SC(A^2)=N-$, $A^1C(=S)NH-$, $A^1SC(=S)NH-$, $A^1SC(SA^2)=N-$, $A^1-ON=C(CN)-$, $A^1-ON=C(Me)CH_2ON=C(CN)-$, or $A^1C(CN)=NOCH_2-$ (wherein $L^1$ represents oxygen, sulfur, carbonyl, $-OCH_2-$, $-SCH_2-$, $-C(=O)O-$, $-OC(=O)-$, $-C(=O)OCH_2-$, $-NH-$, or $C_{1-6}$ alkylimino; $A^1$ and $A^2$ are the same or different, and each represents hydrogen, $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, or $C_{2-19}$ heteroarylalkyl);

$R^2$ represents hydrogen, or $C_{1-6}$ alkyl;

$R^3$ is $C_{1-6}$ alkoxy, $C_{1-6}$ alkylthio, cyano, halogen, or $C_{1-6}$ alkyl;

one of T, U and V represents $CR^4$, another one represents CH or nitrogen, and the remaining one represents $CR^5$ or nitrogen; and W represents $CR^6$ or nitrogen; (wherein $R^4$, $R^5$ and $R^6$ are the same or different, and each represents hydrogen, halogen, $C_{1-6}$ alkyl, $C_{1-6}$ alkoxy, $C_{1-6}$ haloalkyl, $C_{1-6}$ haloalkoxy, cyano, nitro, $C_{2-6}$ alkoxycarbonyl, $C_{1-6}$ alkylthio, or $C_{1-6}$ haloalkylthio), and wherein, in $R^1$, $A^1$ and $A^2$ of the triazolone compound represented by the formula (I), the $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{1-9}$ heteroaryl and/or $C_{2-19}$ heteroarylalkyl may be substituted with the same or different substituents which are one or more substituents selected from the following Group A; and the $C_{6-10}$ aryl and $C_{7-20}$ arylalkyl may be substituted with the same or different substituents which are one or more substituents selected from the group consisting of the following Group A and Group B:

Group A halogen, $C_{1-10}$ alkyl, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, phenoxymethyl, $C_{1-9}$ heteroaryl, ($C_{1-9}$ heteroaryl)methyloxy, ($C_{1-9}$ heteroaryl)oxymethyl, $C_{1-9}$ heteroaryloxyl(wherein each of the phenyl, phenoxy, benzyloxy, phenoxymethyl, $C_{1-9}$ heteroaryl, ($C_{1-9}$ heteroaryl)methyloxy, ($C_{1-9}$ heteroaryl)oxymethyl, and $C_{1-9}$ heteroaryloxy may be substituted with one or more substituents selected from the group consisting of halogen, $C_{1-6}$ alkyl, $C_{1-6}$ alkoxy, trifluoromethyl, and cyano), hydroxyl, cyano and nitro;

Group B methylenedioxy and difluoromethylenedioxy (each of the methylenedioxy and difluoromethylenedioxy is attached to the two adjacent carbon atoms of the aryl moiety).

8. A triazolone compound represented by the formula (IV)

wherein
represents $C_{1-10}$ alkyl, $C_{2-10}$ alkenyl, $C_{2-10}$ alkynyl, halogen, nitro, cyano, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, $C_{2-19}$ heteroarylalkyl, $A^1$—$L^1$—, $A^1$—ON=$CA^2$—, $A^1$—ON=C(Me)$CH_2$ON=$CA^2$—, $A^1C(A^2)$=$NOCH_2$—, $A^1SC(A^2)$=N—, $A^1C(=S)NH$—, $A^1SC(=S)NH$—, $A^1SC(SA^2)$=N—, $A^1$—ON=C(CN)—, $A^1$—ON=C(Me)$CH_2$ON=C(CN)—, or $A^1C(CN)$=$NOCH_2$—(wherein $L^1$ represents oxygen, sulfur, carbonyl, —$OCH_2$—, —$SCH_2$—, —C(=O)O—, —OC(=O)—, —C(=O)$OCH_2$—, —NH—, or $C_{1-6}$ alkylimino; $A^1$ and $A^2$ are the same or different, and each represents hydrogen, $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, or $C_{2-19}$ heteroarylalkyl);
$R^2$ represents hydrogen, or $C_{1-6}$ alkyl;
$R^3$ is $C_{1-6}$ alkoxy, $C_{1-6}$ alkylthio, cyano, halogen, or $C_{1-6}$ alkyl;
one of T, U and V represents $CR^4$, another one represents CH or nitrogen, and the remaining one represents $CR^5$ or nitrogen; and
W represents $CR^6$ or nitrogen; (wherein $R^4$, $R^5$ and $R^6$ are the same or different, and each represents hydrogen, halogen, $C_{1-6}$ alkyl, $C_{1-6}$ alkoxy, $C_{1-6}$ haloalkyl, $C_{1-6}$ haloalkoxy, cyano, nitro, $C_{2-6}$ alkoxycarbonyl, $C_{1-6}$ alkylthio, or $C_{1-6}$ haloalkylthio), and
wherein, in $R^1$, $A^1$ and $A^2$ of the triazolone compound represented by the formula (I), the $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{1-9}$ heteroaryl and $C_{2-19}$ heteroarylalkyl may be substituted with the same or different substituents which are one or more substituents selected from the following Group A1; and
the $C_{6-10}$ aryl and $C_{7-20}$ arylalkyl may be substituted with the same or different substituents which are one or more substituents selected from the group consisting of the following Group A1 and Group B:
Group A1 halogen, $C_{1-10}$ alkyl, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, pyridine-2-yloxy (wherein each of the phenyl, phenoxy, benzyloxy, and pyridine-2-yloxy may be substituted with one or more substituents selected from the group consisting of halogen, $C_{1-6}$ alkyl, $C_{1-6}$ alkoxy, trifluoromethyl, and cyano), hydroxyl, cyano and nitro;
Group B methylenedioxy and difluoromethylenedioxy (each of the methylenedioxy and difluoromethylenedioxy is attached to the two adjacent carbon atoms of the aryl moiety).

9. The triazolone compound according to any one of claims 1,2,3 or 4, wherein $R^3$ of the above formula (I) is methoxy, methylthio, cyano, halogen, vinyl, ethynyl, cyclopropyl, ethyl, or methyl.

10. The triazolone compound according to any one of claims 1,2,3 or 4, wherein $R^3$ of the above formula (I) is methoxy, methylthio, cyano, halogen, ethyl, or methyl.

11. The triazolone compound according to any one of claims 1,2,3 or 4, wherein $R^3$ of the above formula (I) is methoxy.

12. The triazolone compound according to any one of claims 1,2,3 or 4, wherein one of T, U and V of the above formula (I) is $CR^4$, another one is CH, and the remaining one is $CR^5$; and W is $CR^6$.

13. The triazolone compound according to any one of claims 1,2,3 or 4, wherein $R^4$, $R^5$ and $R^6$ of the triazolone derivative represented by the above formula (I) are the same or different and are hydrogen, halogen or methyl.

14. The triazolone compound according to any one of claims 1,2,3 or 4, wherein U, V and W are CH and T is $CR^4$.

15. The triazolone compound according to claim 14, wherein $R^4$ is methyl.

16. The triazolone compound according to any one of claims 1,2,3 or 4, wherein $R^1$ of the above formula (I) is phenyl, $C_{1-9}$ heteroaryl, $C_{2-10}$ alkynyl or $A^1$—ON=$CA^2$—.

17. The triazolone compound according to claim 15, wherein $R^1$ of the above formula (I) is phenyl, $C_{1-9}$ heteroaryl, $C_{2-10}$ alkynyl or $A^1$—ON=C(Me)—.

18. The triazolone compound according to any one of claims 1,2,3 or 4, wherein $R^2$ of the above formula (I) is hydrogen or methyl.

19. The triazolone compound according to any one of claims 1,2,3 or 4, wherein $R^2$ of the above formula (I) is hydrogen.

20. The triazolone compound according to any one of claims 1 or 3, wherein $R^1$ of the above formula (I) is phenyl, $C_{1-9}$ heteroaryl, $C_{2-10}$ alkynyl or $A^1$—ON=$CA^2$—,
wherein $C_{2-10}$ alkynyl and $C_{1-9}$ heteroaryl may be substituted with the same or different substituents which are one or more substituents selected from the following Group A; and
the phenyl may be substitued with the same or different substituents which are one or more substituents selected from the group consisting of the following Group A and Group B:
Group A halogen, $C_{1-10}$ alkyl, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, phenoxymethyl, $C_{1-9}$ heteroaryl, ($C_{1-9}$ heteroaryl)methyloxy, ($C_{1-9}$ heteroaryl)oxymethyl, $C_{1-9}$ heteroaryloxy (wherein each of the phenyl, phenoxy, benzyloxy, phenoxymethyl, $C_{1-9}$ heteroaryl, ($C_{1-9}$ heteroaryl)methyloxy, ($C_{1-9}$ heteroaryl)oxymethyl, and $C_{1-9}$ heteroaryloxy may be substituted with one or more substituents selected from the group consisting of halogen, $C_{1-6}$ alkyl, $C_{1-6}$ alkoxy, trifluoromethyl, and cyano), hydroxyl, cyano and nitro;
Group B methylenedioxy and difluoromethylenedioxy (each of the methylenedioxy and difluoromethylenedioxy is attached to the two adjacent carbon atoms of the aryl moiety).

21. The triazolone compound according to any one of claims 2 or 4, wherein $R^1$ of the above formula (I) is phenyl, $C_{1-9}$ heteroaryl, $C_{2-10}$ alkynyl or $A^1$—ON=$CA^2$—, wherein $C_{2-10}$ alkynyl and $C_{1-9}$ heteroaryl may be substituted with the same or different substituents which are one or more substituents selected from the following Group A1; and the phenyl may be substitued with the same or different substituents which are one or more substituents selected from the group consisting of the following Group A1 and Group B:

Group A1 halogen, $C_{1-10}$ alkyl, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, pyridine-2-yloxy (wherein each of the phenyl, phenoxy, benzyloxy, and pyridine-2-yloxy may be substituted with one or more substituents selected from the group consisting of halogen, $C_{1-6}$ alkyl, $C_{1-6}$ alkoxy, trifluoromethyl, and cyano), hydroxyl, cyano and nitro;

Group B methylenedioxy and difluoromethylenedioxy (each of the methylenedioxy and difluoromethylenedioxy is attached to the two adjacent carbon atoms of the aryl moiety).

22. The triazolone compound according to claim 14, wherein $R^4$ is methyl, and $R^1$ of the above formula (I) is phenyl, $C_{1-9}$ heteroaryl, $C_{2-10}$ alkynyl or $A^1$—ON=C(Me)—, wherein the $C_{2-10}$ alkynyl and $C_{1-9}$ heteroaryl may be substituted with the same or different substituents which are one or more substituents selected from the following Group A; and the phenyl may be substitued with the same or different substituents which are one or more substituents selected from the group consisting of the following Group A and Group B:

Group A halogen, $C_{1-10}$ alkyl, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, phenoxymethyl, $C_{1-9}$ heteroaryl, ($C_{1-9}$ heteroaryl) methyloxy, ($C_{1-9}$ heteroaryl)oxymethyl, $C_{1-9}$ heteroaryloxy (wherein each of the phenyl, phenoxy, benzyloxy, phenoxymethyl, $C_{1-9}$ heteroaryl, ($C_{1-9}$ heteroaryl)methyloxy, ($C_{1-9}$ heteroaryl)oxymethyl, and $C_{1-9}$ heteroaryloxy may be substituted with one or more substituents selected from the group consisting of halogen, $C_{1-6}$ alkyl, $C_{1-6}$ alkoxy, trifluoromethyl, and cyano), hydroxyl, cyano and nitro;

Group B methylenedioxy and difluoromethylenedioxy (each of the methylenedioxy and difluoromethylenedioxy is attached to the two adjacent carbon atoms of the aryl moiety).

23. The triazolone compound according to claim 14, wherein $R^4$ is methyl, and $R^1$ of the above formula (I) is phenyl, $C_{1-9}$ heteroaryl, $C_{2-10}$ alkynyl or $A^1$—ON=C(Me)—, wherein the $C_{2-10}$ alkynyl and $C_{1-9}$ heteroaryl may be substituted with the same or different substituents which are one or more substituents selected from the following Group A1; and the phenyl may be substitued with the same or different substituents which are one or more substituents selected from the group consisting of the following Group A1 and Group B:

Group A1 halogen, $C_{1-10}$ alkyl, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, pyridine-2-yloxy (wherein each of the phenyl, phenoxy, benzyloxy, and pyridine-2-yloxy may be substituted with one or more substituents selected from the group consisting of halogen, $C_{1-6}$ alkyl, $C_{1-6}$ alkoxy, trifluoromethyl, and cyano), hydroxyl, cyano and nitro;

Group B methylenedioxy and difluoromethylenedioxy (each of the methylenedioxy and difluoromethylenedioxy is attached to the two adjacent carbon atoms of the aryl moiety).

24. An agricultural or horticultural fungicide composition as an active ingredient, a triazolone compound represented by the formula (I)

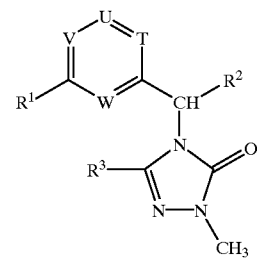

wherein $R^1$ represents $C_{1-10}$ alkyl, $C_{2-10}$ alkenyl, halogen, nitro, cyano, $C_{3-10}$ cycloalkyl, $C_{4-20}$ cycloalkylalkyl, $C_{5-10}$ cycloalkenyl, $C_{6-20}$ arly, $C_{7-20}$ aryalkyl, $C_{1-9}$ heteroaryl, $C_{2-19}$ heteroarylalkyl, $A^1$—$L^1$—, $A^1$—ON=$CA^2$—, $A^1$—ON=C(Me)CH$_2$ON=CA$^2$—, $A^1C(A^2)$=NOCH$_2$—, $A^1SC(A^2)$=N—, $A^1c(=S)$NH—, $A^1SC(=S)$NH—, $A^1SC(SA^2)$=N—, $A^1$—ON=C(CN)—, $A^1$—ON=C(Me)CH$_{2=l}$ON=c(CN)—, or $A^1C(CN)$=NOCH$_2$—(wherein $L^1$ represents oxygen, sulfur, carbonyl, —OCH$_2$—, —SCH$_2$—, —C(=O)O—, —OC(=O)—, —C(=O)OCH$_2$—, —NH—, or $C_{1-6}$ alkylimino; $A^1$ and $A^2$ are the same or different, and each represents hydrogen, $C_{1-10}$ alkyl, $C_{2-10}$ alkenyl, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, or $C_{2-19}$ heteroarylalkyl);

$R^2$ represents hydrogen, or $C_{1-6}$ alkyl;

$R^3$ represents $C_{1-6}$ alkylthio, cyano, halogen, vinyl, ethynyl, cycloprpyl, or $C_{1-6}$ alkyl;

one of T, U and V represents $CR^4$, another one represents CH or Nitrogen, and the remaining one represnets $CR^5$ or nitrogen;

W represents $CR^6$ or nitrogen; (wherein $R^4$, $R^5$ and $R^6$ are the same or different, and each represents hydrogen, halogen, $C_{1-6}$ alkyl, $C_{1-6}$ alkoxy, $C_{1-6}$ haloalkyl, $C_{1-6}$ haloalkoxy, cyano, nitro, $C_{2-6}$ alkoxycarbonyl, $C_{1-6}$ alkylthio, or $C_{1-6}$ haloalkylthio), and wherein, in $R^1$, $A^1$ and $A^2$ of the triazolone compound represented by the formula (I), the $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{1-9}$ heteroaryl and/or $C_{2-19}$ heteroarylalkyl may be substituted with the same or different substituents which are one or more substituents selected from the following Group A; and the $C_{6-10}$ aryl and $C_{7-20}$ arylalkyl may be substituted with the same or different substituents which are one or more substituents selected from the group consisting of the following Group A and Group B:

Group A halogen, $C_{1-10}$ alkyl, $C_{3-20}$ trialkylsilyl, $C_{1-10}$ haloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, phenoxymethyl, $C_{1-9}$ heteroaryl, ($C_{1-9}$ heteroaryl)methyloxy, ($C_{1-9}$ heteroaryl)oxymethyl, $C_{1-9}$ heteroaryloxy (wherein each of the phenyl, phenoxy, benzyloxy, phenoxymethyl, $C_{1-9}$ heteroaryl, ($C_{1-9}$ heteroaryl)methyloxy, ($C_{1-9}$ heteroaryl) oxymethyl, and $C_{1-9}$ heteroaryloxy may be substitued with one or more substituents selected from the group consisting of halogen, $C_{1-6}$ alkyl, $C_{1-6}$ alkoxy, trifluoromethyl, and cyano), hydroxyl, cyano and nitro;

Group B

Methylenedioxy and difluoromethylenedioxy (each of the methylenedioxy and difluoromethylenedioxy is attached to the two adjacent carbon atoms of the aryl moiety).

25. An agricultural or horticultural fungicide composition comprising as an active ingredient, a triazolone derivative represented by the formula (I)

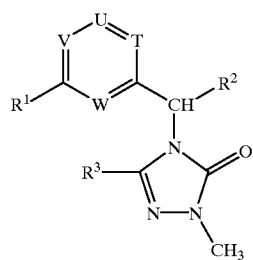

wherein $R^1$ represents $c_{1-10}$ alkyl, $C_{2-10}$ alkenyl, $C_{2-10}$ alkynyl, halogen, nitro, cyano, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, $C_{2-19}$ heteroarylalkyl, $A^1-L^1-$, $A^1-ON=CA^2-$, $A^1-ON=C(Me)Ch_2ON=CA^2-$, $A^1C(A^2)=NOCH_2-$, $A^1SC(A^2)=N-$, $A^1C(=S)NH-$, $A^1SC(=S)NH-$, $A^1SC(SA^2)=N-$, $A^1-ON=C(CN)-$, $A^1-ON=C(Me)CH_2ON=C(Cn)-$, or $A^1C(CN)=NOCH_2-$ (wherein $L^1$ represents oxygen, sulfur, carbonyl, $-OCH_2-$, $-SCH_2-$, $-C(=O)O-$, $-OC(=O)-$, $-C(=O)OCH_2-$, $-NH-$, or $C_{1-6}$ alkylimino; $A^1$ and $A^2$ are the same or different, and each represents hydrogen, $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, or $C_{2-19}$ heteroarylalkyl);

$R^2$ represents hydrogen, or $C_{1-6}$ alkyl;

$R^3$ represents $C_{1-6}$ alkoxy, $C^{1-6}$ alkylthio, cyano, halogen, vinyl, ethynyl, cyclopropyl, or $C_{1-6}$ alkyl;

one of T, U and V represents $CR^4$, another one represents CH or nitrogen, and the remaining one represents $CR^5$ or mitrogen;

W represents $CR^6$ or nitrogen; (wherein $R^4$, $R^5$ and $R^6$ are the same or different, and each represents hydrogen, halogen, $C^{1-6}$ alkyl, $C_{1-6}$ alkoxy, $C_{1-6}$ haloalkyl, $C_{1-6}$ haloalkoxy, cyano, nitro, $C_{2-6}$ alkoxycarbonyl, $C_{1-6}$ alkythio, or $C_{1-6}$ haloalkylthio), and wherein, in $R^1$, $A^1$ and $A^2$ of the triazolone compound represented by the formula (I), the $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{1-9}$ heteroaryl and $C_{2-19}$ heteroarylalkyl may be substitued with the same or different substituents which are one or more substituents selected from the following Group A1; and the $C_{6-10}$ aryl and $C_{7-20}$ arylalkyl may be substituted with the same or different substituents which are one or more substituents selected from the group consisting of the following Group A1 and Group B:

Group A1 halogen, $C_{1-10}$ alkyl, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, pyridine-2-yloxy (wherein each of the phenyl, phenoxy, benzyloxy, and pyridine-2-yloxy may be substituted with one or more substituents selected from the group consisting of halogen, $C_{1-6}$ alkyl, $C_{1-6}$ alkoxy, trifluoromethyl, and cyano), hydroxyl, cyano and nitro;

Group B methylenedioxy and difluoromethylenedioxy (each of the methylenedioxy and difluoromethylenedioxy is attached to the two adjacent carbon atoms of the aryl moiety).

26. An agricultural or horticultural fungicide composition comprising as an active ingredient, a triazolone compound represented by the formula (I)

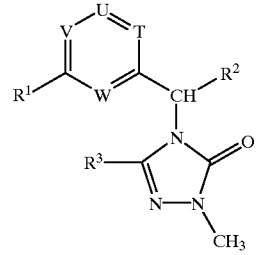

wherein $R^1$ represents $c_{1-10}$ alkyl, $C_{2-10}$ alkenyl, $C_{2-10}$ alkynyl, halogen, nitro, cyano, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, $C_{2-19}$ heteroarylalkyl, $A^1-L^1-$, $A^1-ON=CA^2-$, $A^1-ON=C(Me)Ch_2ON=CA^2-$, $A^1C(A^2)=NOCH_2-$, $A^1SC(A^2)=N-$, $A^1C(=S)NH-$, $A^1SC(=S)NH-$, $A^1SC(SA^2)=N-$, $A^1-ON=C(CN)-$, $A^1-ON=C(Me)CH_2ON=C(Cn)-$, or $A^1C(CN)=NOCH_2-$ (wherein $L^1$ represents oxygen, sulfur, carbonyl, $-OCH_2-$, $-SCH_2-$, $-C(=O)O-$, $-OC(=O)-$, $-C(=O)OCH_2-$, $-NH-$, or $C_{1-6}$ alkylimino; $A^1$ and $A^2$ are the same or different, and each represents hydrogen, $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, or $C_{2-19}$ heteroarylalkyl);

$R^2$ represents hydrogen, or $C_{10-6}$ alkyl;

$R^3$ is $C_{1-6}$ alkoxy, $C_{1-6}$ alkylthio, cyano, halogen, or $C_{1-6}$ alkyl;

one of T, U and V represents $CR^4$, another one represents CH or nitrogen, and the remaining one represents $CR^5$ or mitrogen;

W represents $CR^6$ or nitrogen; (wherein $R^4$, $R^5$ and $R^6$ are the same or different, and each represents hydrogen, halogen, $C_{1-6}$ alkyl, $C_{1-6}$ alkoxy, $C_{1-6}$ haloalkyl, $C_{1-6}$ haloalkoxy, cyano, nitro, $C_{2-6}$ alkoxycarbonyl, $C_{1-6}$ alkylthio, or $C_{1-6}$ haloalkylthio), and wherein, in $R^1$, $A^1$ and $A^2$ of the triazolone compound represented by the formula (I), the $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{1-9}$ heteroaryl and $C_{2-19}$ heteroarylalkyl may be substitued with the same or different substituents which are one or more substituents selected from the following Group A; and the $C_{6-10}$ aryl and $C_{7-20}$ arylalkyl may be substituted with the same or different substituents which are one or more substituents selected from the group consisting of the following Group A and Group B:

Group A halogen, $C_{1-10}$ alkyl, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, phenoxymethyl, $C_{1-9}$ heteroaryl, ($C_{1-9}$ heteroaryl)methyloxy, ($C_{1-9}$ heteroaryloxy (wherein each of the phenyl, phenoxy, benzyloxy, phenoxymethyl, $C_{1-9}$ heteroaryl, ($C_{1-9}$ heteroaryl)methyloxy, ($C_{1-9}$ heteroaryl)oxymethyl, and $C_{1-9}$ heteroaryloxy may be substituted with one or more substituents selected from the group consisting of halogen, $C_{1-6}$ alkyl, $C_{1-6}$ alkoxy, trifluoromethyl, and cyano), hydroxyl, cyano and nitro;

Group B methylenedioxy and difluoromethylenedioxy (each of the methylenedioxy and difluoromethylenedioxy is attached to the two adjacent carbon atoms of the aryl moiety).

27. An agricultural or horticultural fungicide composition comprising as an active ingredient, a triazolone compound represented by the formula (I)

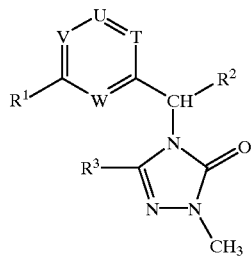

wherein $R^1$ represents $c_{1-10}$ alkyl, $C_{2-10}$ alkenyl, $C_{2-10}$ alkynyl, halogen, nitro, cyano, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, $C_{2-19}$ heteroarylalkyl, $A^1—L^1—$, $A^1—ON=CA^2—$, $A^1—ON=C(Me)Ch_2ON=CA^2—$, $A^1C(A^2)=NOCH_2—$, $A^1SC(A^2)=N—$, $A^1C(=S)NH—$, $A^1SC(=S)NH—$, $A^1SC(SA^2)=N—$, $A^1—ON=C(CN)—$, $A^1—ON=C(Me)CH_2ON=C(Cn)—$, or $A^1C(CN)=NOCH_2—$ (wherein $L^1$ represents oxygen, sulfur, carbonyl, $—OCH_2—$, $—SCH_2—$, $—C(=O)O—$, $—OC(=O)—$, $—C(=O)OCH_2—$, $—NH—$, or $C_{1-6}$ alkylimino; $A^1$ and $A^2$ are the same or different, and each represents hydrogen, $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{6-10}$ aryl, $C_{7-20}$ arylalkyl, $C_{1-9}$ heteroaryl, or $C_{2-19}$ heteroarylalkyl);

$R^2$ represents hydrogen, or $C_{10-6}$ alkyl;

$R^3$ is $C_{1-6}$ alkoxy, $C_{1-6}$ alkylthio, cyano, halogen, or $C_{1-6}$ alkyl;

one of T, U and V represents $CR^4$, another one represents CH or nitrogen, and the remaining one represents $CR^5$ or mitrogen;

W represents $CR^6$ or nitrogen; (wherein $R^4$, $R^5$ and $R^6$ are the same or different, and each represents hydrogen, halogen, $C_{1-6}$ alkyl, $C_{1-6}$ alkoxy, $C_{1-6}$ haloalkyl, $C_{1-6}$ haloalkoxy, cyano, nitro, $C_{2-6}$ alkoxycarbonyl, $C_{1-6}$ alkylthio, or $C_{1-6}$ haloalkylthio), and wherein, in $R^1$, $A^1$ and $A^2$ of the triazolone compound represented by the formula (I), the $C_{1-10}$ alkyl, $C_{2-10}$ alkenyl, $C_{2-10}$ alkynyl, $C_{3-10}$ cycloalkyl, $C_{4-20}$ cycloalkylalkyl, $C_{5-10}$ cycloalkenyl, $C_{6-20}$ cycloalkenylalkyl, $C_{1-9}$ heteroaryl and $C_{2-19}$ heteroarylalkyl may be substitued with the same or different substituents which are one or more substituents selected from the following Group A1; and the $C_{6-10}$ aryl and $C_{7-20}$ arylalkyl may be substituted with the same or different substituents which are one or more substituents selected from the group consisting of the following Group A1 and Group B:

Group A1 halogen, $C_{1-10}$ alkyl, $C_{3-20}$ trialkylsilyl, $C_{1-10}$ haloalkyl, $C_{3-10}$ cycloalkyl, $C_{1-10}$ alkoxy, $C_{1-10}$ haloalkoxy, $C_{1-10}$ alkylthio, $C_{1-10}$ haloalkylthio, $C_{2-10}$ alkoxycarbonyl, phenyl, phenoxy, benzyloxy, pyridine-2-yloxy (wherein each of the phenyl, phenoxy, benzyloxy, and pyridine-2-yloxy may be substituted with one or more substituents selected from the group consisting of halogen, $C_{1-6}$ alkyl, $C_{1-6}$ alkoxy, trifluoromethyl, and cyano), hydroxyl, cyano and nitro;

Group B methylenedioxy and difluoromethylenedioxy (each of the methylenedioxy and difluoromethylenedioxy is attached to the two adjacent carbon atoms of the aryl moiety).

* * * * *